US008481701B2

(12) United States Patent
Jarrige-Le Prado et al.

(10) Patent No.: US 8,481,701 B2
(45) Date of Patent: Jul. 9, 2013

(54) PROCESS AND METHOD FOR DIAGNOSING ALZHEIMER'S DISEASE

(75) Inventors: Anne-Charlotte Jarrige-Le Prado, Paris (FR); Pascale Beurdeley, Fontenay Sous Bois (FR); Diego Pallares, Paris (FR); Fabien Rouet, Rueil Malmaison (FR); Laurent Bracco, La Garenne Colombes (FR)

(73) Assignee: Exonhit Therapeutics SA, Paris (FR)

( * ) Notice: Subject to any disclaimer, the term of this patent is extended or adjusted under 35 U.S.C. 154(b) by 10 days.

(21) Appl. No.: 12/935,098

(22) PCT Filed: Mar. 30, 2009

(86) PCT No.: PCT/FR2009/050530
§ 371 (c)(1),
(2), (4) Date: Dec. 20, 2010

(87) PCT Pub. No.: WO2009/144424
PCT Pub. Date: Dec. 3, 2009

(65) Prior Publication Data
US 2011/0086776 A1    Apr. 14, 2011

Related U.S. Application Data

(60) Provisional application No. 61/044,097, filed on Apr. 11, 2008.

(30) Foreign Application Priority Data

Mar. 28, 2008   (FR) ..................................... 08 52042

(51) Int. Cl.
*C07H 21/02*  (2006.01)
*C07H 21/04*  (2006.01)
*C12Q 1/68*  (2006.01)

(52) U.S. Cl.
USPC ........ 536/23.1; 536/24.3; 435/287.1; 435/6.1

(58) Field of Classification Search
None
See application file for complete search history.

(56) References Cited

U.S. PATENT DOCUMENTS

2001/0053519 A1* 12/2001 Fodor et al. ....................... 435/6
2007/0082350 A1   4/2007 Landfield et al.

FOREIGN PATENT DOCUMENTS

| FR | 2900936 | 11/2007 |
|---|---|---|
| WO | WO 03/028543 | 4/2003 |
| WO | WO 03/054143 | 7/2003 |
| WO | WO 2004/079014 | 9/2004 |
| WO | WO 2004/112589 | 12/2004 |
| WO | WO 2005/020784 | 3/2005 |
| WO | WO 2005/076939 | 8/2005 |
| WO | WO 2006/002262 | 1/2006 |
| WO | WO 2006/020269 | 2/2006 |
| WO | WO 2006/125830 | 11/2006 |
| WO | WO 2006/138275 | 12/2006 |
| WO | WO 2009/074331 | 6/2009 |

OTHER PUBLICATIONS

Gardina P.J. et al. BMC Genomics (Dec. 2006), pp. 1-18.*
Hoffmann E.P. et al. As The Tumor Analysis Best Practices Working Group, Nature Reviews—Genetics, Mar. 2004, vol. 5, pp. 229-237.*
GenBank Locus: AB000461 'Homo sapiens mRNA, complete cds, clone:RES4-22C.' Apr. 14, 2000, from www.ncbi.nlm.nih.gov, pp. 1-4.*
GenBank Locus: CQ834138 'Sequence 9 from Patent WO2004058805' Jul. 29, 2004, from www.ncbi.nlm.nih.gov, pp. 1-2.*
GenBank Locus: AX780939 'Sequence 3096 from Patent WO03039443' Jul. 14, 2003, from www.ncbi.nlm.nih.gov, pp. 1-2.*
GenBank Locus: AK023239 'Homo sapiens cDNA FLJ13177 fis, clone NT2RP3003870, highly smilar to binding protein (VprBP), mRNA' Sep. 16, 2006, from www.ncbi.nlm.nih.gov, pp. 1-3.*
GenBank Locus: AK074705 'Homo sapiens cDNA FLJ90224 fis, clone NT2RM1000789, highlysimilar to transcription factor 7-like 2, T-cell specific, HMG-box (Tcf712), mRNA for hTCF-4' Sep. 13, 2006, from www.ncbi.nlm.nih.gov, pp. 1-2.*
GenBank Locus: NM_004844 'Homo sapiens SH3-domain binding protein 5 (BTK-associated) (SH3BP5), transcript variant 1, mRNA.' Jun. 15, 2006, from www.ncbi.nlm.nih.gov, pp. 1-5.*
Beurdeley P, et al "P1-343: Discovery of blood gene expression biomarkers in Alzheimer's disease using the human genome-wide splice array" *Alzheimer's & Dementia: The Journal of the Alzheimer's Associate.* vol. 4, No. 4 (Jul. 1, 2008) p. T319.
Maes et al. "Transcriptional profiling of Alzheimer blood mononuclear cells by microarray" *Neurobiology of Aging.* vol. 28, No. 12. (Oct. 12, 2007) pp. 1795-1809.
Ray Sandip et al. "Classification and prediction of clinical Alzheimer's diagnosis based on plasma signaling proteins" *Nature Medicine.* vol. 13, No. 11 (Nov. 2007) pp. 1359-1362 (Abstract only).
Wilmot, et al "Translational gene mapping of cognitive decline" *Neurobiology of Aging.* vol. 29, No. 4. (Mar. 3, 2008) pp. 524-541.
Maddalena, et al. "Cerebrospinal Fluid Profile of Amyloid β Peptides in Patients with Alzheimer's Disease Determined by Protein Biochip Technology" *Neuro-degenerative Diseases.* (2004) pp. 231-235 DOI: 10.1159/000080991.
Wang, et al. "Preliminary studies on Alzheimer's disease using cDNA microarrays" *Mechanisms of Ageing and Development.* vol. 124. (2003) pp. 115-124.
Ho, et al. "Altered expression of a-type by not b-type synapsin isoform in the brain of patients at high risk for Alzheimer's disease assessed by DNI microarray technique" *Neuroscience Letters.* vol. 298. (2001) pp. 191-194.

\* cited by examiner

*Primary Examiner* — Stephen Kapushoc
(74) *Attorney, Agent, or Firm* — Occhiuti Rohlicek & Tsao LLP

(57) ABSTRACT

The present invention concerns methods and compositions usable for diagnosing Alzheimer's disease in mammals, in particular humans. It particularly describes serum markers for Alzheimer's disease and their use in diagnostic methods. It also concerns tools and/or kits usable for implementing these methods (reagents, probes, primers, antibodies, chips, cells, etc.), their preparation and their use. The invention is usable to detect the presence or progression of Alzheimer's disease in mammals, including in the early phase, as well as for predicting the efficacy of an Alzheimer's disease treatment.

4 Claims, 6 Drawing Sheets

5A

5B

6A

6B

6C

PROCESS AND METHOD FOR DIAGNOSING ALZHEIMER'S DISEASE

CROSS-REFERENCE TO RELATED APPLICATIONS

Figure 1:
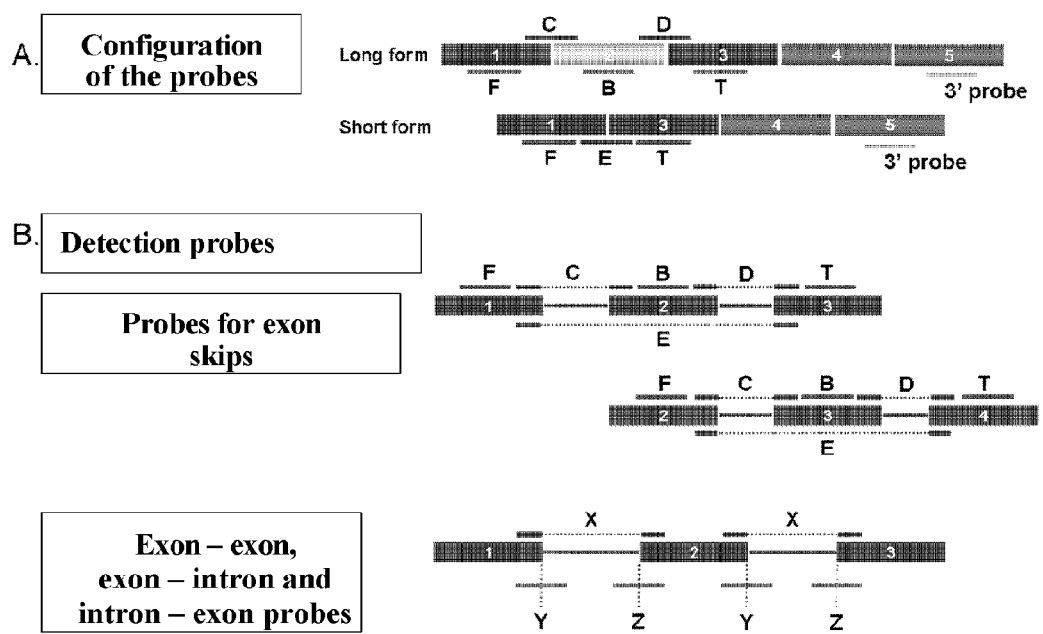

This application is the National Stage of International Application No. PCT/FR2009/050530, filed on Mar. 30, 2009, which claims the priority of French Application No. 0852042, filed on Mar. 28, 2008, and U.S. Provisional Application No. 61/044,097, filed on Apr. 11, 2008, the contents of the foregoing applications is incorporated herein by reference in their entirety.

Two identical copies of a compact disc have been submitted in this application. Both copies contain the following files: 55602-004US1 Table 1.txt (created May 22, 2012; 509,952 bytes), 55602-004US1 Table 2.txt (created May 22, 2012; 251,904 bytes), and 55602-004US1 Sequence Listing.txt (created May 4, 2012; 9,277,440 bytes). Files 55602-004US1 Table 1.txt and 55602-004US1 Table 2.txt correspond to Tables 1 and 2 mentioned below, respectively. File 55602-004US1 Sequence Listing.txt contains a sequence listing. The entire contents of these files are hereby incorporated by reference in their entirety.

The present invention relates to methods and compositions suitable for detecting Alzheimer's disease in mammals, humans in particular. It particularly describes serum markers for Alzheimer's disease and their use in diagnostic methods. It also concerns tools and/or kits suitable for implementing these methods (reagents, probes, primers, antibodies, chips, cells, etc.), their preparation and their use. The invention can be used to detect the presence or progression of Alzheimer's disease in mammals, including in the early phase.

Alzheimer's disease is the primary cause of dementia and the most common neurodegenerative disease. This progressive disease is characterized by memory loss and by deterioration in language skills, orientation and judgment. The nature of the symptoms, often confused with aging-related physiological problems, their severity and their age of onset vary among individuals. This makes it difficult to establish a diagnosis in the early stages of the disease.

Examination of the brains of patients suffering from this disease shows a loss of neurons in the hippocampus, an important memory center, and in the cerebral cortex, involved in reasoning, language and memory. Cholinergic neurons are particularly affected by this depletion.

Another major anomaly observed in the brains of patients suffering from Alzheimer's disease is the accumulation of intracellular and extracellular protein aggregates. Intracellular neurofibrillary tau protein aggregates appear to be well correlated with the severity of the dementia. Senile plaques formed by intra- and extracellular aggregation of amyloid beta peptide characterize regions of neuron and glial cell alterations.

However, it is noteworthy that these areas of aggregation do not correspond to the sites of synapse depletion characteristic of the decline in cognitive function.

Genetic studies conducted on familial forms have shown that 4 genes are associated with the development of the disease: APP (Amyloid Precursor Protein; precursor of amyloid beta peptide), presenilins 1 and 2 (PS1 and PS2) and apolipoprotein E (ApoE). Although mutations or polymorphisms in each of these genes lead to an increased production of amyloid beta protein, the mechanisms that govern the synaptic and neuronal losses remain poorly understood. In this regard, several hypotheses and mechanisms appear to coexist, involving different phenomena:

1. Purely cerebral phenomena involving neurons and glial cells:
    oxidative stress, which can especially be induced by amyloid beta peptide and modulated by cholesterol metabolism;
    changes in calcium flux and excitotoxicity.
2. Inflammation and immune reactions;
3. A change in sex hormones;
4. Hypothyroidism and defects in the regulation of insulin signals.

Consequently, Alzheimer's disease will be characterized by a change in various integration systems regulating homeostasis, and damage to certain neurons leading to both an inflammatory reaction involving the immune system and changes in endocrine regulation. These, in return, have an impact on the activity and viability of other neurons and on immune functions; these cascade reactions emphasize the role not only of neurodegeneration but also hormonal regulation and the immune response in the progression of Alzheimer's disease.

Currently there is no robust and specific signature for Alzheimer's disease, especially from a blood sample, that allows diagnosing this disease, in particular the different stages of disease progression. The availability of an effective diagnostic test, particularly for early diagnosis, would allow patients to be treated from the beginning of the disease and thus to benefit from a treatment that is more effective and more appropriate, in particular by acetylcholinesterase inhibitors such as galantamine, donepezil and rivastigmine, under optimal conditions.

The present invention responds to this need. The invention particularly describes the identification of serum markers for Alzheimer's disease, allowing the development of effective and predictive diagnostics for the presence, degree of severity/advancement or risk of developing this disease. The invention describes the identification of molecular signatures specifically or preferentially expressed in the blood of patients with Alzheimer's disease, resulting particularly from the complex expression of certain genes linked to alternative splicing. The invention particularly describes the identification of sequences 1-5578, which are present in the RNA of blood cells in human subjects, and which are characteristic, alone or in combination, of Alzheimer's disease. The invention therefore offers, for the first time, tools and methods for diagnosing, predicting and/or monitoring the progression of Alzheimer's disease, based on measuring the expression of one or more genes in the subjects' blood. The presence of deregulation in the expression of such genes allows establishing the risk of or predisposition to Alzheimer's disease, or confirming the presence of this disease in a subject.

One object of the invention thus relates to a method for detecting (in vitro or ex vivo) the presence or risk of developing Alzheimer's disease in a mammal, comprising determining the presence, in a biological sample from said mammal, preferably in a blood (derivative) sample, of an alteration in one or more genes or RNAs comprising a sequence chosen from among SEQ ID Nos.: 1 to 5578, the presence of such an alteration being indicative of the presence or risk of developing Alzheimer's disease in said mammal.

Another object of the invention is a method for detecting (in vitro or ex vivo) the capacity for developing Alzheimer's disease in a mammal with mild cognitive impairment or at asymptomatic stages of Alzheimer's disease, especially of the hippocampal or amnesic type, comprising determining the presence, in a biological sample from said mammal, preferably in a blood (derivative) sample, of an alteration in one or more genes or RNAs comprising a sequence chosen from among SEQ ID Nos.: 1 to 5578, the presence of such an alteration being indicative of the risk of developing Alzheimer's disease in said mammal.

Another object of the invention concerns a method for evaluating or monitoring the response to a treatment for Alzheimer's disease, comprising a step of measuring the expression of one or, preferably, several genes or RNAs comprising a sequence chosen from among SEQ ID Nos.: 1 to 5578 before and/or during the treatment, and a comparison of the expression thus measured to the one measured at an earlier stage of the treatment or at the treatment.

Another object of the invention concerns an improvement to the methods for treating Alzheimer's disease, the improvement comprising measuring the expression of one or, preferably, several genes or RNAs comprising a sequence chosen from among SEQ ID Nos.: 1 to 5578 in a subject before and/or during the treatment. Measuring expression allows adjusting the treatment as a function of disease progression. The treatment is typically a treatment by acetylcholinesterase inhibitors such as galantamine, donepezil and rivastigmine.

Another object of the invention concerns the use of an acetylcholinesterase inhibitor, such as galantamine, donepezil and rivastigmine, for the preparation of a drug to treat Alzheimer's disease in a patient with deregulation of the expression of (at least) one gene such as defined previously.

Alteration in a gene or RNA means, in the sense of the invention, (i) any change in expression, i.e., in particular, a deregulation in the expression (e.g., transcription or translation) level, a deregulation in splicing, leading, for example, to the appearance of particular splice forms or a change in the (relative) quantity or ratio between different splice forms, as well as (ii) any change in the structure of the protein produced (appearance or disappearance of truncated, elongated or mutated forms, etc.).

As it will be described in the following text, the present application describes the identification of splicing deregulations in certain genes in the blood of patients with Alzheimer's disease. Any molecule or technique permitting to measure the expression of these genes in the blood can be implemented in the scope of the present invention, such as nucleotide primers, nucleotide probes or specific antibodies, which can be in suspension or in the immobilized form, as it will be described in detail in the following text.

Thus, another object of the present application concerns a product comprising a support on which are immobilized nucleic acids containing a sequence complementary and/or specific for one or, preferably, several genes or RNAs such as defined previously. Preferably, the product comprises distinct nucleic acids comprising a sequence complementary and/or specific for at least 5, 10, 20, 30, 40, 50, 60 or more genes or RNAs such as previously defined.

Another object of the present application concerns a product comprising a support on which is immobilized at least one ligand for a polypeptide coded by a gene or RNA such as defined above. Preferably, the product comprises at least 5, 10, 20, 30, 40, 50, 60 or more ligands of different polypeptides chosen from among the polypeptides mentioned above.

Another object of the present invention concerns a kit comprising a compartment or container comprising at least one, preferably several, nucleic acids comprising a sequence complementary and/or specific for one or more genes or RNAs such as defined previously and/or one, preferably several, ligands for one or more polypeptides such as defined previously. Preferably, the product comprises at least 5, 10, 20, 30, 40, 50, 60 or more different nucleic acids and/or ligands chosen from among the nucleic acids and ligands mentioned above. The kit can also comprise reagents for a hybridization or immunological reaction, as well as, if applicable, controls and/or instructions.

Another object of the invention concerns the use of a product or kit such as defined above for the detection of Alzheimer's disease in a mammalian subject, preferably a human subject.

Another object of the invention concerns the use of a product or kit such as defined above for the determination of the risk of developing Alzheimer's disease in a mammalian subject, preferably a human subject, in particular in a subject with mild cognitive impairment or at asymptomatic stages of Alzheimer's, in particular of the hippocampal or amnesic type.

Another object of the invention concerns the use of a product or kit such as defined above to discriminate subjects with Alzheimer's disease from subjects with mild cognitive impairment.

Another object of the invention concerns the use of a product or kit such as defined above to determine the response to a treatment for Alzheimer's disease or for the selection of subjects likely to effectively respond to a treatment.

Another object of the invention concerns a method for detecting or screening for Alzheimer's disease, comprising determining the presence of one or more target molecules chosen from among:
   a) nucleic acids containing at least one pair of sequences defined in Table 2 or a fragment thereof having at least 15, preferably at least 16, 17, 18, 19, 20, 25 or 30 consecutive bases,
   b) nucleic acids having a sequence complementary to a sequence according to a),
   c) functional analogs of nucleic acids according to a) or b), or
   d) polypeptides coded by nucleic acids according to a) to c).

Another object of the invention resides in an isolated nucleic acid comprising a sequence chosen from among SEQ ID Nos: 1 to 5578 or a fragment thereof having at least 15, 16, 17, 18, 19 or 20 consecutive bases, or a sequence complementary thereto. Preferably, the nucleic acid of the invention does not comprise the complete sequence of a natural gene or RNA. Preferably, it includes no more than 500 bases, preferably no more than 400 or 300 bases. The nucleic acid of the invention is typically synthetic, i.e., produced by non-natural pathways (recombinant, in vitro, chemical synthesis, etc.).

Another object of the invention is a polypeptide encoded by a nucleic acid such as defined above.

Serum Markers for Alzheimer's Disease

The present invention relies on the detection and characterization of serum biological events characteristic of Alzheimer's disease in a human patient. These events represent biomarkers, whose detection in a patient, preferably in combination, allows determining, even at an early stage, the risk of developing such a disease, the presence of such a disease, or the stage of progression of this disease. Moreover, the markers according to the invention are also usable to measure the response to a treatment and/or to select candidate drugs. The combinations of markers of the invention can distinguish Alzheimer's disease from other neurodegenerative diseases.

The biological events identified typically correspond to changes in the regulation of gene expression. It can be a matter of partial or total inhibition of the expression of genes or RNA, or certain forms of genes or RNA, an increase in the expression of genes or certain forms of genes or RNA, the appearance or disappearance of gene splice forms, etc.

The invention therefore relies on the detection in a sample of one or more target molecules advantageously chosen from among:

a) nucleic acids containing a sequence chosen from among SEQ ID NOs: 1-5578, or a distinctive fragment thereof having at least 15, preferably at least 16, 17, 18, 19, 20, 25 or 30 consecutive bases.

b) nucleic acids having a sequence complementary to a sequence according to a), c) functional analogs of nucleic acids according to a) or b), or d) polypeptides coded by nucleic acids according to a) to c).

The term "functional analog" preferably designates a polymorphic variant of SEQ ID NO: 1-5578 present in the human population. In the majority of cases, these polymorphisms are represented by point variations at the base level, although other polymorphic configurations also exist. These analogs may be identified by any technique known to the person skilled in the art, particularly in consideration of the sequences provided in the application and the names of the corresponding genes. The term analog also includes sequences originating from another mammalian species. In fact, the genes corresponding to SEQ ID NO: 1-5578 are human genes, and these sequences constitute effective and appropriate markers for the detection of Alzheimer's disease in human patients. However, for applying the methods of the invention to other mammalian species, it is generally preferable to use functional analogs of these sequences, characterized in the species in question.

In one particular embodiment, the method comprises determining the presence (or the absence or a variation in the expression level) of at least one nucleic acid according to a) to c).

In one particular embodiment, the method is used to detect Alzheimer's disease in a human subject and comprises determining the presence (or the absence or a variation in the expression level) of at least one nucleic acid according to a) to c).

In one particular variant, the method comprises the combined determination of the presence of absence or (relative) quantity of at least 5, 10, 15, 20, 30, 40, 50, 60, 70 or more target molecules such as defined above. "Combined" determination means that a hybridization profile (or a signature) involving several markers is determined. Combined determination is typically done simultaneously, i.e., by an overall measurement of an expression profile. However, combined determination can also be done by parallel or sequential measurements of several markers, leading to identifying a profile. The invention allows establishing and determining a hybridization profile (or a signature) on a collection of markers, in order to evaluate the presence or risk of developing Alzheimer's disease in a mammal The hybridization profile is typically made by using a combination of several markers chosen from among the targets indicated above, for example containing all these targets.

In one particular embodiment, the method of the invention comprises determining the presence (or the absence or the (relative) quantity), in a biological sample from the mammal, of at least 5 distinct target molecules chosen from among those defined above, preferably at least 10.

In preferred embodiments, the method of the invention comprises the combined determination of the presence (or the absence or the (relative) quantity), in a biological sample from the mammal, of particular subsets of target molecules chosen from among those defined above. Such subsets, described in the examples, are particularly suited to the detection, especially in the early phase, of the presence of Alzheimer's disease in patients from a whole blood sample.

Thus, in one particular embodiment, the method of the invention comprises the combined determination of the presence (or the absence or the (relative) quantity), in a biological sample from the mammal, of the nucleic acids of an entire panel of targets (or signatures) comprising markers such as defined in a) to d) above, preferably of all the molecules of one of panels 1 to 60 defined in the present application.

Thus, in one particular embodiment, the method of the invention comprises the combined determination of the presence (or the absence or the (relative) quantity), in a biological sample from the mammal, of all the nucleic acids of one of Panels 1 to 60 comprising the sequences shown in Table 1, columns G to BN, respectively, or a distinctive fragment thereof having at least 15, preferably at least 16, 17, 18, 19, 20, 25 or 30 consecutive bases, or having a sequence complementary thereto and/or functional analogs thereof originating from other species, and/or polypeptides encoded by these nucleic acids. The examples provided in the present application show that this marker panel allows predictively detecting the presence, the risk of developing, or the stage of progression of Alzheimer's disease. In one particular embodiment, the method also comprises the detection of one or more other target molecules such as previously defined.

In a specific embodiment, the method of the invention comprises determining the presence (or the absence or the (relative) quantity), in a mammalian biological sample, of nucleic acids respectively comprising the sequences shown in SEQ ID NOs: 1-5578, or a distinctive fragment thereof having at least 15, preferably at least 16, 17, 18, 19, 20, 25 or 30 consecutive bases, or nucleic acids having a sequence complementary thereto.

Another particular object of the invention resides in a method for detecting the presence or risk of developing Alzheimer's disease in a mammal, comprising contacting, under conditions allowing hybridization between complementary sequences, nucleic acids from a blood sample of the mammal and a set of probes specific for the following target molecules:

a) nucleic acids comprising the sequences shown in any one of PANELS1 to 60 such as defined above, or a distinctive fragment thereof having at least 15, preferably at least 16, 17, 18, 19, 20, 25 or 30 consecutive bases, and/or b) nucleic acids having a sequence complementary to sequences according to a), and/or c) functional analogs of nucleic acids according to a) or b) coming from another species, in order to obtain a hybridization profile, the hybridization profile being characteristic of the presence or risk of developing Alzheimer's disease in said mammal.

Another particular object of the invention resides in a method for detecting the risk of developing Alzheimer's disease in a mammal presenting mild cognitive impairment, or in an asymptomatic mammal, or to discriminate patients with Alzheimer's from patients with mild cognitive impairment, comprising contacting, under conditions allowing hybridization between complementary sequences, nucleic acids from a blood sample from the mammalian and a probe set, the probe set comprising at least one probe comprising all or part of each of the nucleic acid sequences of one of the following panels, or their complementary sequence:

set 1: 6PS
set 2: 27PS in order to obtain a hybridization profile, the hybridization profile being characteristic of the presence or risk of developing Alzheimer's disease in this mammal.

Another object of the invention resides in the use of a probe set, the probe set comprising at least one probe comprising all or part of each of the nucleic acid sequences of one of the following panels, or their complementary sequence:
set 1: 6PS
set 2: 27PS
to detect the presence or the risk of developing Alzheimer's disease in a subject with mild cognitive impairment, or in an asymptomatic subject, or to discriminate subjects with Alzheimer's from subjects with mild cognitive impairment.

Another particular object of the invention is a method for detecting the presence or risk of developing Alzheimer's disease in a mammal, comprising contacting, under conditions allowing hybridization between complementary sequences, nucleic acids from a blood sample from the mammalian and a probe set, the probe set comprising at least one probe comprising all or part of each of the nucleic sequences of the following panel, or their complementary sequence:
set 3: 18PS
in order to obtain a hybridization profile, the hybridization profile being characteristic of the presence or risk of developing Alzheimer's disease in said mammal.

Another object of the invention is the use of a probe set, the probe set comprising at least one probe comprising all or part of each of the nucleic acid sequences of one of the following panels, or their complementary sequence:
set 3: 18PS
for detecting the presence or the risk of developing Alzheimer's disease in a subject.

Another object of the invention is a method for detecting the presence or the risk of developing Alzheimer's disease in a mammal, or for discriminating patients with Alzheimer's disease from subjects with mild cognitive impairment or control subjects, the method comprising detecting, from a blood sample of said mammal, a variation in the levels of nucleic acids complementary of a probe set, the probe set comprising at least one probe comprising all or part of each of the nucleic sequences of one of the following panels, or their complementary sequence:
set 1: 6PS
set 2: 27PS
set 3: 18PS
set 4: 33 PS
a variation being characteristic of the presence or risk of developing Alzheimer's disease in said mammal.

The invention also allows defining additional panels, containing at least some markers such as defined previously, which may possibly be combined with other markers. Such panels may be obtained by testing for the presence or absence of these markers in patient samples, in order to define other predictive combinations, if applicable, specific for particular pathologies.

Methods for Detecting an Alteration in a Gene

As previously indicated, an alteration in a gene or RNA means, in the sense of the invention, (i) any change in expression, i.e., in particular, a deregulation in the level of expression (e.g., transcription or translation), a deregulation in splicing, leading to, for example, the appearance of particular splice forms or a change in the (relative) quantity or ratio between the different splice forms, as well as (ii) any change in the structure of the protein produced (appearance or disappearance of truncated, elongated or mutated forms, etc.).

Various techniques allowing the detection of a nucleic acid species in a sample can be used in the present invention, such as, for example, Northern blot, selective hybridization, the use of supports coated with oligonucleotide probes, amplification of the nucleic acid by RT-PCR, quantitative PCR or ligation-PCR, etc. These methods can comprise the use of a nucleic acid probe (for example an oligonucleotide) that can selectively or specifically detect the target nucleic acid in the sample. Amplification can be done according to various methods known in themselves to the person skilled in the art, such as PCR, LCR, transcription-mediated amplification (TMA), strand-displacement amplification (SDA), NASBA, the use of allele-specific oligonucleotides (ASO), allele-specific amplification, Southern blot, single-strand conformational analysis (SSCA), in-situ hybridization (e.g., FISH), migration on a gel, heteroduplex analysis, etc. If necessary, the quantity of nucleic acid detected can be compared to a reference value, for example a median or mean value observed in patients who do not have Alzheimer's disease, or to a value measured in parallel in a control sample. Thus, it is possible to demonstrate a variation in the level of expression.

According to one preferred embodiment, the method comprises detecting the presence or absence or (relative) quantity of a nucleic acid according to a) to c) by selective hybridization or selective amplification.

Selective hybridization is typically done by using nucleic probes, preferably immobilized on a support, such as a solid or semi-solid support with at least one surface, flat or not, for immobilizing nucleic acid probes. Such supports are, for example, a slide, bead, membrane, filter, column, plate, etc. They can be made of any compatible material, such as, notably, glass, silica, plastic, fiber, metal, polymer, etc. The nucleic acid probes can be any nucleic acid (DNA, RNA, PNA, etc.), preferably single strand, comprising a sequence specific for a target molecule such as defined in a) to c) above. The probes typically contain 5 to 400 bases, preferably 8 to 200, more preferentially less than 100, and still more preferentially, less than 75, 60, 50, 40 or even 30 bases. The probes can be synthetic oligonucleotides, produced based on sequences SEQ ID NO: 1-5578 (target sequences) of the invention, according to conventional synthesis techniques. Such oligonucleotides typically have 10 to 50 bases, preferably 20 to 40 bases, for example, approximately 25 bases. In one particularly advantageous embodiment, so as to improve the signal detected, several different oligonucleotides (or probes) defined from a same target sequence are used to detect the same target molecule (transcript from the amplification of patient RNA) during hybridization. It can be oligonucleotides specific for different regions of the same target sequence, or centered differently on the same region. Advantageously probe sets containing 1-3 probes are used, which can be overlapping or not, completely or partially, and which are specific for the same target molecule. Probe pairs can also be used, one member of which is perfectly matched to the target sequence, and the other having a mismatch, thereby estimating background noise. The probes can be designed to hybridize to an exon or intron region, or an exon-exon, exon-intron or intron-intron junction region. Thus, the probes allow detecting and distinguishing different splice forms of a gene.

In one preferred embodiment, probes are used whose sequence comprises all or part of a nucleic acid sequence chosen from among SEQ ID NOs: 1-5578 or a complementary sequence thereof. In a preferred embodiment, nucleic acid probes are used with a length comprised between 15 and 50 bases, more preferentially between 15 and 40 bases, and whose sequence is identical to a fragment of a sequence chosen from among SEQ ID NO: 1-5578 or a complementary sequence thereof.

In one particularly preferred embodiment, probe sets are used, i.e., sets of 1-3 probes each containing a part, overlapping or not, of the same nucleic acid sequence chosen from among SEQ ID NOs: 1-5578.

The probes can be synthesized beforehand then deposited on the support, or synthesized directly in situ, on the support, according to methods known per se to the person skilled in the art. The probes can also be fabricated by genetic techniques, for example by amplification, recombination, ligation, etc.

The probes thus defined represent another object of the present application, as well as their use (essentially in vitro) for the detection of Alzheimer's disease in a subject.

Hybridization can be done under conventional conditions, known to the person skilled in the art and adjustable by this person (Sambrook, Fritsch, Maniatis (1989) Molecular Cloning, Cold Spring Harbor Laboratory Press). In particular, hybridization can be done under high, medium or low stringency conditions, according to the level of sensitivity sought, the quantity of material available, etc. For example, appropriate hybridization conditions include a temperature comprised between 55 and 63° C. for 2 to 18 hours. Other hybridization conditions, suitable for high density supports, are, for example, a hybridization temperature between 45 and 55° C. After hybridization, various washings can be done to eliminate the non-hybridized molecules, typically in SSC buffers containing SDS, such as a buffer containing 0.1 to 10×SSC and 0.5-0.01% SDS. Other washing buffers containing SSPE, MES, NaCl or EDTA can also be used.

In a typical embodiment, nucleic acids (or chips or supports) are pre-hybridized in a hybridization buffer (Rapid Hybrid Buffer, Amersham) typically containing 100 μg/mL DNA from salmon sperm at 65° C. for 30 min. The nucleic acids of the sample are then contacted with the probes (typically applied onto the support or chip) at 65° C. for 2 to 18 hours. Preferably, the nucleic acids of the sample are labeled beforehand, by any known label (radioactive, enzymatic, fluorescent, luminescent, etc.). The supports are then washed in a 5×SSC, 0.1% SDS buffer at 65° C. for 30 min, then in a 0.2×SSC, 0.1% SDS buffer. The hybridization profile is analyzed by conventional techniques, such as, for example, by measuring the labeling on the support by means of a suitable instrument (for example InstantImager, Packard Instruments). The hybridization conditions can naturally be adjusted by the person skilled in the art, for example by modifying the hybridization temperature and/or the saline concentration of the buffer as well as by adding auxiliary substances such as formamide or single-strand DNA.

A particular object of the invention is thus a method for detecting the presence or the risk of developing Alzheimer's disease in a mammal, or for evaluating the response to a treatment for Alzheimer's disease, comprising contacting, under conditions allowing hybridization between complementary sequences, nucleic acids from a blood sample from the mammal and a set of probes specific for the target molecules as identified above, to obtain a hybridization profile, the hybridization profile being characteristic of the presence or risk of developing Alzheimer's disease in this mammal, or the efficacy of treatment.

A particular object of the invention thus resides in a method for detecting the presence or risk of developing Alzheimer's disease in a mammal, comprising contacting, under conditions allowing hybridization between complementary sequences, nucleic acids from a blood sample from the mammal and a set of probes specific for at least the following target molecules:
a) nucleic acids comprising the sequences shown in panels 1 to 60 defined previously, or a distinctive fragment thereof having at least 15, preferably at least 16, 17, 18, 19, 20, 25 or 30 consecutive bases, and/or
b) nucleic acids having a sequence complementary to a sequence according to a), and/or
c) functional analogs of nucleic acids according to a) or b) originating from another species, in order to obtain a hybridization profile, the hybridization profile being characteristic of the presence or risk of developing Alzheimer's disease in this mammal.

In particular embodiments, the processes of the invention also use other target molecules and/or other probes, particularly the target molecule subset mentioned in the present application.

Thus, another particular object of the invention is a method for detecting the presence or risk of developing Alzheimer's disease in a mammal, comprising contacting, under conditions allowing hybridization between complementary sequences, nucleic acids from a blood sample from the mammal and a set of probes specific for at least two different molecules chosen from among the following targets:
a) nucleic acids containing a sequence chosen from among SEQ ID NOs: 1-5578, or a distinctive fragment thereof having at least 15, preferably at least 16, 17, 18, 19, 20, 25 or 30 consecutive bases and/or
b) nucleic acids having a sequence complementary to a sequence according to a), and/or
c) functional analogs of nucleic acids according to a) or b) coming from another species, in order to obtain a hybridization profile, the hybridization profile being characteristic of the presence or risk of developing Alzheimer's disease in this mammal.

Another particular object of the invention resides in a method for detecting the presence or risk of developing Alzheimer's disease in a mammal, comprising contacting, under conditions allowing hybridization between complementary sequences, nucleic acids from a blood sample from the mammal and a probe set, the probe set comprising at least one probe comprising all or part of each of the nucleic sequences of one of the following panels, or their complementary sequence:
set 1: 6PS
set 2: 27PS
set 3: 18PS
set 4: 33 PS in order to obtain a hybridization profile, the hybridization profile being characteristic of the presence or risk of developing Alzheimer's disease in this mammal.

As explained in more detail in the experimental part (see example 11), set 1 thus comprises at least the following 6 probes:
a probe comprising all or part of the sequence SEQ ID NO: 2363 or its complementary sequence;
a probe comprising all or part of the sequence SEQ ID NO: 2364 or its complementary sequence;
a probe comprising all or part of the sequence SEQ ID NO: 5307 or its complementary sequence;
a probe comprising all or part of the sequence SEQ ID NO: 5426 or its complementary sequence;
a probe comprising all or part of the sequence SEQ ID NO: 4218 or its complementary sequence;
a probe comprising all or part of the sequence SEQ ID NO: 5063 or its complementary sequence.

As indicated previously, the term "part" advantageously designates a region from 15 to 50 consecutive nucleotides.

In one particular embodiment, set 1 comprises:
from 1 to 3 probes, overlapping or not, each comprising all or part of sequence SEQ ID NO: 2363 or its complementary sequence;
from 1 to 3 probes, overlapping or not, each comprising all or part of sequence SEQ ID NO: 2364 or its complementary sequence;

from 1 to 3 probes, overlapping or not, each comprising all or part of sequence SEQ ID NO: 5307 or its complementary sequence;

from 1 to 3 probes, overlapping or not, each comprising all or part of sequence SEQ ID NO: 5426 or its complementary sequence;

from 1 to 3 probes, overlapping or not, each comprising all or part of sequence SEQ ID NO: 4218 or its complementary sequence; and from 1 to 3 probes, overlapping or not, each comprising all or part of sequence SEQ ID NO: 5063 or its complementary sequence.

It is understood that set 1 can contain, in addition to the 6 probes or groups of probes (probe sets) cited, other probes or probe sets, containing, for example, a sequence chosen from among SEQ ID NO: 1-5578 and/or from among other sequences.

Sets 2-4 can be defined like set 1 above. The base probes constituting these sets are given in Example 11.

Another particular object of the invention resides in a method to detect the risk of developing Alzheimer's disease in a mammal presenting mild cognitive impairment, or an asymptomatic one, or to discriminate patients with Alzheimer's from patients with mild cognitive impairment, comprising contacting, under conditions allowing hybridization between complementary sequences, nucleic acids from a blood sample from the mammal and a probe set, the probe set containing several probes comprising at least one probe comprising all or part of each of the nucleic acid sequences of one of the following panels, or their complementary sequence:

set 1: 6PS
set 2: 27PS in order to obtain a hybridization profile, the hybridization profile being characteristic of the presence or risk of developing Alzheimer's disease in this mammal.

Another object of the invention resides in the use of a set of (groups of) probes, the set comprising several (groups of) probes, including at least one probe (or a group of probes) comprising all or part of each of the nucleic acid sequences of one of the following panels, or their complementary sequence:

set 1: 6PS
set 2: 27PS to detect the presence or the risk of developing Alzheimer's disease in a subject with mild cognitive impairment, or an asymptomatic one, or to discriminate subjects with Alzheimer's from subjects with mild cognitive impairment.

The possibility of distinguishing, in patients with mild cognitive impairment (MCI) or asymptomatic patients, those who have Alzheimer's or are likely to develop Alzheimer's is particularly important because it allows quickly initiating the most suitable treatment. Thirty to forty percent of subjects with MCI will progress to AD. The possibility of identifying these subjects from the MCI stage allows initiating effective treatment protocols for AD without waiting for the disease to progress.

Another particular object of the invention is a method for detecting the risk of developing Alzheimer's disease in a mammal, comprising contacting, under conditions allowing hybridization between complementary sequences, nucleic acids from a blood sample from the mammal and a probe set, the probe set comprising at least one probe comprising all or part of each of the nucleic acid sequences of the following panel, or their complementary sequence:

set 3: 18PS in order to obtain a hybridization profile, the hybridization profile being characteristic of the presence or risk of developing Alzheimer's disease in this mammal.

Another object of the invention is the use of a set of (groups of) probes, comprising at least one probe (or group of probes) comprising all or part of each of the nucleic acid sequences of the following panel, or their complementary sequence:

set 3: 18PS for detecting the presence or the risk of developing Alzheimer's disease in a subject.

Another object of the invention is a method for detecting the presence or the risk of developing Alzheimer's disease in a mammal, or for discriminating patients with Alzheimer's from subjects with mild cognitive disorders or control subjects, comprising detecting, from a mammalian blood sample, a variation in the levels of complementary nucleic acids of a probe set, the probe set containing at least one probe comprising all or part of each of the nucleic sequences of one of the following panels, or their complementary sequence:

set 1: 6PS
set 2: 27PS
set 3: 18PS
set 4: 33 PS a variation being characteristic of the presence or risk of developing Alzheimer's disease in this mammal.

The hybridization profile can be compared to one or more reference profiles, notably a reference profile characteristic of healthy subjects and/or subjects with Alzheimer's disease, the comparison allowing determining the probability or risk that the patient tested has of getting Alzheimer's disease. Typically, the comparison is done by means of computer programs known in themselves to the person skilled in the art.

Selective amplification is preferably done by using a primer or pair of primers for amplifying all or part of the target nucleic acids in the sample, when it is present. The primer can be specific for a target sequence such as defined previously according to SEQ ID NO: 1-5578, or a region flanking the target sequence in a nucleic acid of the sample. The primer typically contains a single-strand nucleic acid, of a length advantageously comprised between 5 and 50 bases, preferably between 5 and 30. Such a probe constitutes another object of the present application, as well as its use (essentially in vitro) for the detection of Alzheimer's disease in a subject. The primers can be designed to hybridize to an exon or intron region, or an exon-exon, exon-intron or intron-intron junction region. Thus, the primers allow detecting and distinguishing the different splice forms of a gene.

In this regard, another object of the invention is the use of a nucleotide primer or a set of nucleotide primers amplifying all or part of one or, or preferably several genes or RNAs containing a target sequence according to SEQ ID NO: 1-5578, for detecting the presence or the risk of developing Alzheimer's disease in a mammal, or to evaluate the response to an Alzheimer's disease treatment in a mammal, particularly in a human being.

Another particular object of the invention is a method for detecting the presence or risk of developing Alzheimer's disease in a mammal, comprising contacting, under conditions allowing amplification, nucleic acids from a blood sample from the mammal and a set of primers specific for at least two different molecules chosen from among the following targets:

a) nucleic acids comprising a sequence chosen from among SEQ ID NOs: 1-5578, or a distinctive fragment thereof having at least 15, preferably at least 16, 17, 18, 19, 20, 25 or 30 consecutive bases and/or b) nucleic acids having a sequence complementary to a sequence according to a), and/or c) functional analogs of nucleic acids according to a) or b) originating from another species, in order to obtain an amplification profile, the amplification profile being characteristic of the presence or risk of developing Alzheimer's disease in this mammal.

Detection of an Alteration in a Polypeptide

In another embodiment, the method comprises determining the presence or (relative) quantity of a polypeptide coded by a gene such as previously defined. The detection or assay of a polypeptide in a sample can be done by any known technique, such as, notably, by means of a specific ligand, for example an antibody or an antibody fragment or derivative. Preferably, the ligand is an antibody specific for the polypeptide, or a fragment of such an antibody (for example a Fab, Fab', CDR, etc.), or a derivative of such an antibody (for example, a single-chain antibody, ScFv). The ligand is typically immobilized on a support, such as a slide, ball, column, plate, etc. The presence or the quantity of the target polypeptide in the sample can be detected by detecting a complex between the target and the ligand, for example by using a labeled ligand, by using a second labeled visualization ligand, etc. Well known and usable immunological techniques are ELISA, RIA, etc. If necessary, the quantity of polypeptide detected can be compared to a reference value, for example a median or mean value observed in patients who do not have Alzheimer's disease, or to a value measured in parallel in a control sample. Thus, it is possible to demonstrate a variation of the expression level.

Antibodies specific for the target polypeptides can be produced by conventional techniques, notably by immunizing a non-human animal with an immunogen containing the polypeptide (or an immunogenic fragment thereof), and recovering (polyclonal) antibodies or producing cells (to produce monoclonals). Techniques for producing poly- or monoclonal antibodies, ScFv fragments, and human or humanized antibodies are described, for example in Harlow et al., Antibodies: A Laboratory Manual, CSH Press, 1988; Ward et al., Nature 341 (1989) 544; Bird et al., Science 242 (1988) 423; WO94/02602; U.S. Pat. Nos. 5,223,409; 5,877,293; WO93/01288. The immunogen can be fabricated by synthesis or by expression, in an appropriate host, of a target nucleic acid such as defined above. Such an antibody, monoclonal or polyclonal, as well as its derivatives having the same antigenic specificity, also constitute a object of the present application, as well as their use for detecting Alzheimer's disease.

Changes in the expression and/or the structure of proteins can also be detected by means of techniques known in themselves to the person skilled in the art and involving mass spectroscopy, more generally grouped under the name proteomic analysis, in order to detect specific signatures from the blood of patients with Alzheimer's disease.

Implementation of the Process

The method of the invention is applicable to any tested mammalian biological sample, in particular any sample containing nucleic acids or polypeptides. Advantageously, we can mention a blood, plasma, platelet, saliva, urine, stool, etc. sample, or more generally, any tissue, organ or, advantageously, biological fluid containing nucleic acids or polypeptides.

In one preferred and particularly advantageous embodiment, the sample is a sample derived from blood, for example a blood, serum or plasma sample. The invention identifies blood markers for Alzheimer's disease, and thus allows detecting this disease without tissue biopsy, requiring only blood samples.

The sample can be obtained by any technique known per se, for example, by taking samples, by non-invasive techniques, from sample collections or banks, etc. The sample can also be pretreated to facilitate the accessibility of the target molecules, for example by lysis (mechanical, chemical, enzymatic, etc.), purification, centrifugation, separation, etc. The sample can also be labeled, to facilitate the determination of the presence of target molecules (fluorescent, radioactive, luminescent, chemical, enzymatic, etc. labeling). The nucleic acids of the sample can also be separated, treated, enriched, purified, retrotranscribed, amplified, and fragmented. In one particular embodiment, the nucleic acids of the sample are RNAs, notably the mRNAs of the sample. In another particular embodiment, the nucleic acids are the product of RNA amplification, notably mRNAs, or cDNAs prepared from RNA, notably the mRNAs of the sample.

In one preferred embodiment, the biological sample is a whole blood sample, i.e., it has not undergone a separation step, which may be diluted.

The invention can be applied to any mammal, preferably to humans. The method of the invention is particularly useful for the detection of Alzheimer's disease, notably the presence, risk of development, or degree of severity/advancement of Alzheimer's disease in the human being. Thus, the data provided in the examples show that the invention detects the presence of Alzheimer's disease with a sensitivity greater than 95% and a specificity greater than 95%.

One particular object of the present invention concerns a method for detecting the presence, the progression, or the risk of developing Alzheimer's disease in a human subject, comprising the combined determination of the presence (or absence or (relative) quantity), in a biological sample from a human subject, of target molecules chosen from among:

a) nucleic acids containing a sequence chosen from among SEQ ID Nos: 1-5578, or a distinctive fragment thereof having at least 15, preferably at least 16, 17, 18, 19, 20, 25 or 30 consecutive bases, b) nucleic acids having a sequence complementary to a sequence according to a), and c) polypeptides coded by nucleic acids according to a) or b).

Preferably, the method comprises the combined determination of the presence, absence or quantity of 5, 10, 20, 30, 40, 50 or 60 target molecules such as defined above.

Another particular object of the present application concerns a method for detecting the presence, the progression, or the risk of developing Alzheimer's disease in a human subject, comprising contacting a biological sample from the subject containing nucleic acids with a product containing a support on which are immobilized nucleic acids containing a sequence complementary and/or specific for one or, preferably, several target molecules chosen from among (i) nucleic acids containing a sequence chosen from among SEQ ID NO: 1-5578, or a fragment thereof having at least 15, preferably at least 16, 17, 18, 19, 20, 25 or 30 consecutive bases and (ii) nucleic acids having a sequence complementary to a sequence according to (i), and the profile indicating the presence, the degree of severity/advancement or the risk of developing Alzheimer's disease in said human subject. Preferably, the product contains distinct nucleic acids comprising a sequence complementary and/or specific for at least 5, 10, 20, 30, 40, 50, 60 or more genes or RNAs such as discussed above.

Another object of the present application concerns a product comprising a support on which are immobilized nucleic acids containing a sequence complementary and/or specific for one or, preferably, several target molecules chosen from among (i) nucleic acids containing a sequence chosen from among SEQ ID NO: 1-5578, or a fragment thereof having at least 15, preferably at least 16, 17, 18, 19, 20, 25 or 30 consecutive bases and (ii) nucleic acids having a sequence complementary to a sequence according to (i). Preferably, the product contains distinct nucleic acids comprising a complementary and/or specific sequence for at least 5, 10, 20, 30, 40, 50, 60 or more genes or RNAs such as previously defined.

Another object of the present application concerns a product containing a support on which is immobilized at least one, preferably several, nucleic acids containing a sequence chosen from among SEQ ID NO: 1-5578 or a functional analog thereof. Preferably, the product contains at least 5, 10, 20, 30, 40, 50, 60 or more different nucleic acids chosen from among the nucleic acids mentioned above.

Another object of the present application concerns a product comprising a support on which is immobilized a probe set, the probe set containing several probes, at least one of which comprises all or part of each of the nucleic acid sequences of one of the following panels, or their complementary sequence:
  set 1: 6PS,
  set 2: 27PS
  set 3: 18PS, or
  set 4: 33PS.

Another object of the present application concerns a product comprising a support on which is immobilized at least one ligand for a polypeptide coded by a target nucleic acid such as defined above, i.e., a nucleic acid containing a sequence chosen from among SEQ ID NO: 1-5578, or a distinctive fragment thereof, having at least 15, preferably at least 16, 17, 18, 19, 20, 25 or 30 consecutive bases, a nucleic acid having a sequence complementary thereto or a functional analog thereof. Preferably, the product comprises at least 5, 10, 20, 30, 40, 50, 60 or more ligands of different polypeptides chosen from among the polypeptides mentioned above.

The support can be any solid or semi-solid support having at least one surface, flat or not (i.e., in 2 or 3 dimensions), allowing immobilizing nucleic acids or polypeptides. Such supports are, for example, a slide, bead, membrane, filter, column, plate, etc. They can be made of any compatible material, such as, notably, glass, silica, plastic, fiber, metal, polymer, polystyrene, Teflon, etc. The reagents can be immobilized on the support surface by known techniques, or in the case of nucleic acids, synthesized directly in situ on the support. Immobilization techniques include passive adsorption (Inouye et al., J. Clin. Microbiol. 28 (1990) 1469) and covalent bonding. Some techniques are described, for example, in WO90/03382 and WO99/46403. The reagents immobilized on the support can be arranged according to a pre-established plan, in order to facilitate the detection and identification of the complexes formed, and according to a variable and adaptable density.

In one embodiment, the product of the invention contains several synthetic oligonucleotides, of a length comprised between 5 and 100 bases, specific for one or more genes or RNAs such as previously defined.

The products of the invention typically contain control molecules for calibrating and/or standardizing the results.

Another object of the present application concerns a product containing a support on which are immobilized nucleic acids comprising all or part of sequences chosen from among SEQ ID NO: 5579-21559. These sequences represent specific probes for SEQ ID NO: 1-5578. Such a product can advantageously incorporate nucleic acids chosen for their nondiscriminating nature for the population of patients with Alzheimer's disease, such as nucleic acids serving as standardization controls for the product. These nucleic acids can correspond to all or part of sequences chosen from among SEQ ID NO: 21560-51087.

Another object of the present application concerns a kit containing a compartment or container comprising at least one, preferably several, nucleic acids comprising a complementary and/or specific sequence for one or more genes or RNAs such as defined previously and/or one, or preferably several, ligands for one or more polypeptides such as defined previously. Preferably, the product contains at least 5, 10, 20, 30, 40, 50, 60 or more different nucleic acids and/or ligands chosen from among the nucleic acids and ligands mentioned above. In one particular embodiment, the product contains each of the nucleic acids of sequence SEQ ID NO: 1-5578 or a ligand for each of the target polypeptides such as defined above. In another particular embodiment, the product contains each of the nucleic acids of sequence SEQ ID NO: 5579-51087. The kit can also include reagents for a hybridization or immunological reaction, as well as, if applicable, controls and/or instructions.

Another object of the invention concerns the use of a product or kit such as defined above for the detection of Alzheimer's disease in a mammalian subject, preferably a human subject.

Another object of the invention concerns a nucleic acid having a sequence chosen from among SEQ ID NO: 1-5578, or a distinctive fragment thereof, containing at least 15, preferably at least 16, 17, 18, 19, 20, 25 or 30 consecutive bases, or a nucleic acid having a sequence complementary thereto or a functional analog thereof. The invention also concerns a cloning or expression vector containing these nucleic acids, as well as any recombinant cell containing such a vector or nucleic acid.

Another object of the invention concerns the use of a nucleic acid containing a sequence chosen from among SEQ ID NO: 1-5578, or a distinctive fragment thereof, containing at least 15, preferably at least 16, 17, 18, 19, 20, 25 or 30 consecutive bases, or a nucleic acid having a complementary sequence thereof or a functional analog thereof, for the detection (essentially in vitro) of Alzheimer's disease in a mammalian subject.

According to one particular embodiment of the invention, a blood sample is taken from the mammal to be tested. The blood sample may be treated so as to make the nucleic acids more accessible, and these nucleic acids are labeled. The nucleic acids are then applied onto a product such as defined above and the hybridization profile is determined, permitting diagnosing whether Alzheimer's disease is present in the subject or not. The method of the invention is simple, practiced ex vivo, and permits early detection of Alzheimer's disease from a blood sample.

It is understood that any equivalent technique can be used in the scope of the present application to determine the presence of a target molecule.

Other aspects and advantages of the present invention will appear upon reading the examples that follow, which should be considered as illustrative and non-limiting.

FIGURE LEGEND

FIG. 1. Configuration of the probes present on the GWSA microarray. A) B, F, and T exon probes and the C, D and E junction probes optimally cover the splicing events. B) Probes that can completely cover a single exon skip are also present with the same configuration. Likewise, exon-exon (X), exon-intron (Z) and intron-exon (Y) junction probes are also present.

Figure 2:
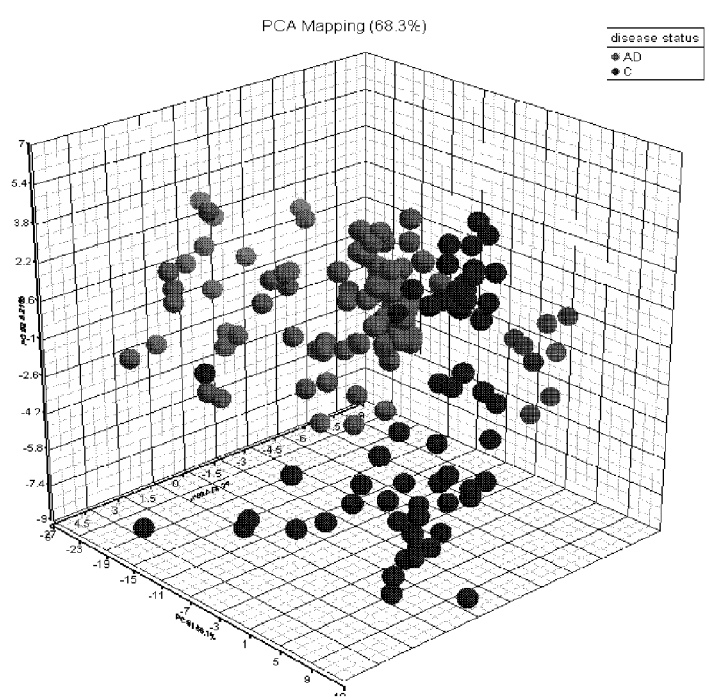

FIG. 2. Principal Component Analysis of AD patients and controls with the SVM signature of panel 50.

Figure 3:
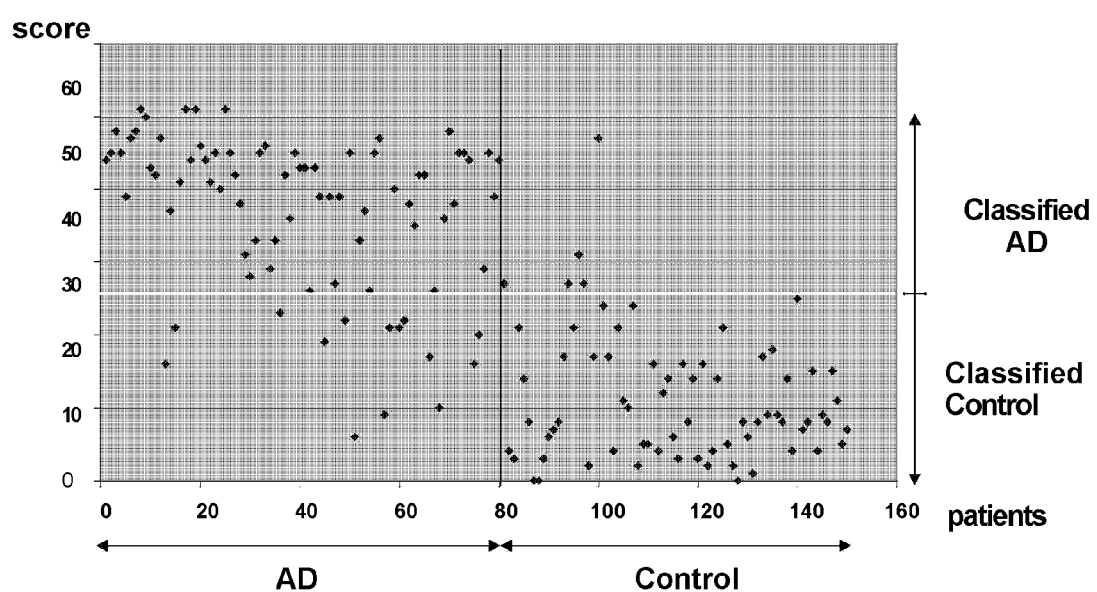

FIG. 3. Classification scores obtained from 51 probe set pairs from PTPRC, SORL1 and PSEN1 genes. AD Patients: No. 1 to 80. Control individuals: No. 81 to 150. The maximal score is 51. The horizontal white line shows the value 25.5. Any patient whose score is above this value is classified as AD. Any patient whose score is below this value is classified as control.

Figure 4:
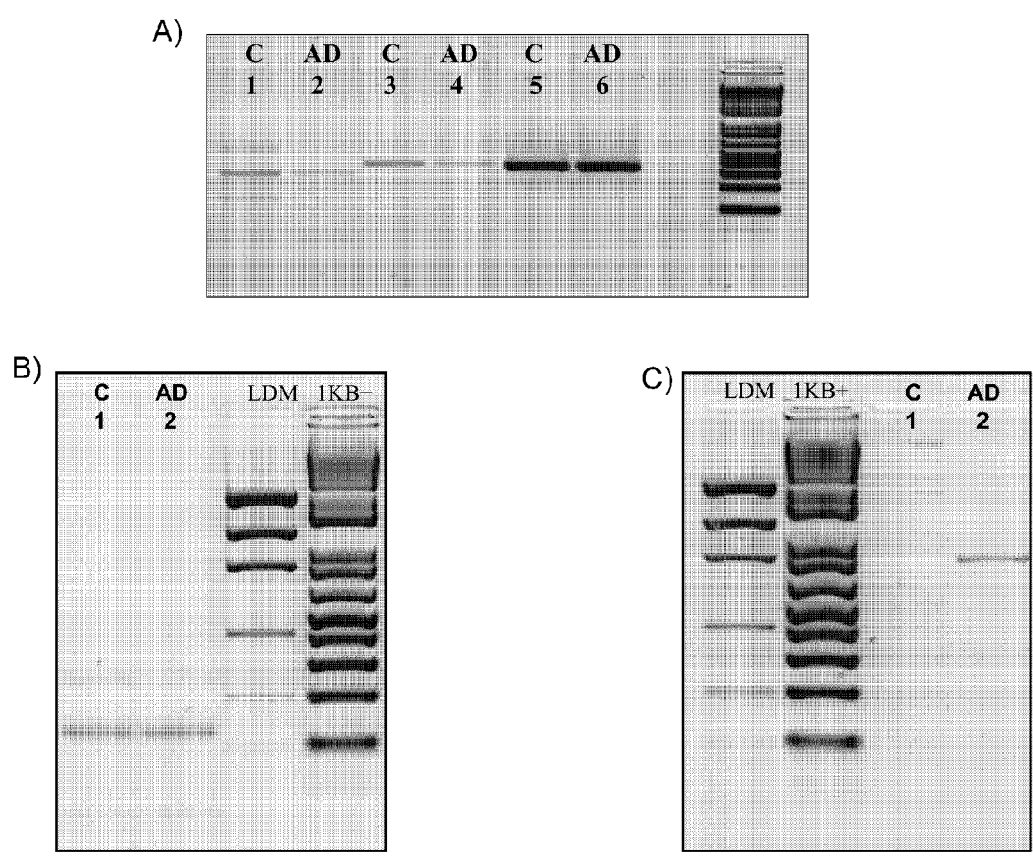

FIG. 4. RT-PCR tests. A) PTPRC gene. 1-2: Primers in exon 2 and intron 5; 3-4: Primers in exon 4 and intron 5; 5-6: Tubulin primers (positive control). B) SORL1 gene. 1-2: Primers in intron 41 and exon 42. C) PSEN1 gene. 1-2: Primers in alternative exon represented by EST AK122722.1, located between exons 3 and 4 and in exon 4.

Figure 5:
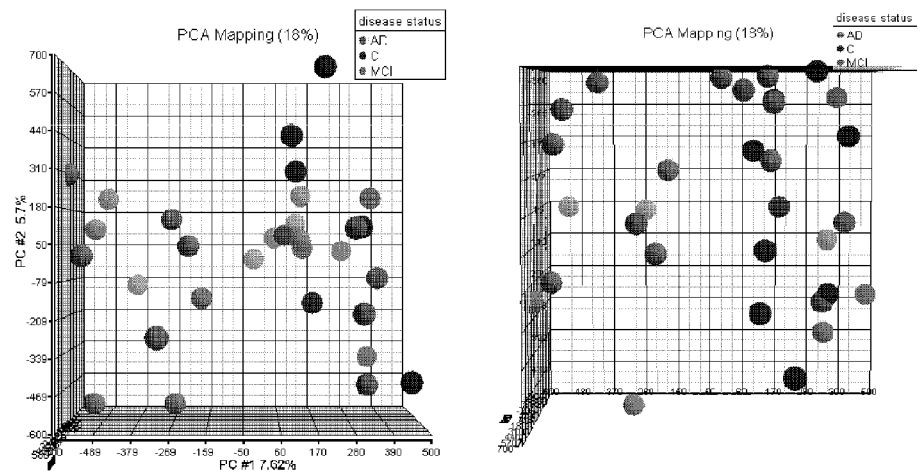
Figure 5:
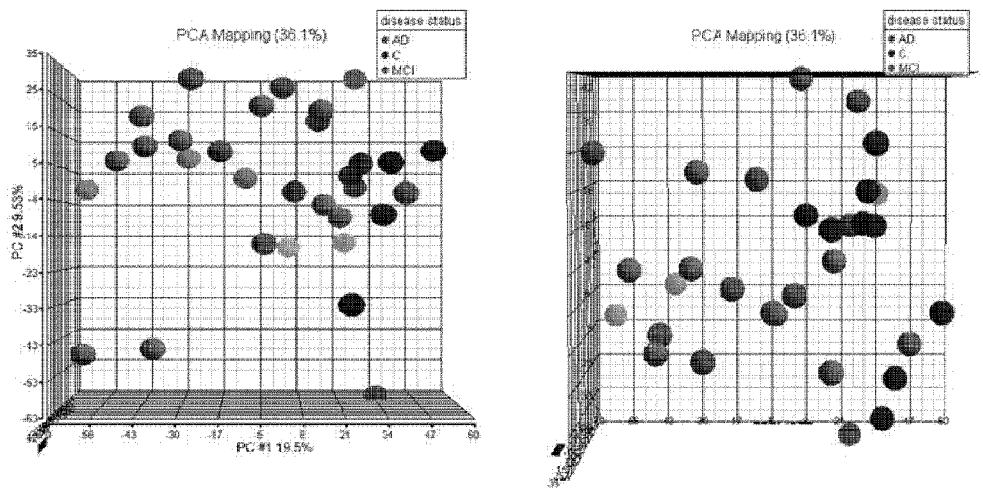

FIG. 5. Principal Component Analysis of AD, MCI and C patients from all the groups of probes present on the GWSA array (FIG. 5A) or a sub-selection made up of 5562 groups of probes among the 5578 (FIG. 5B).

Figure 6:
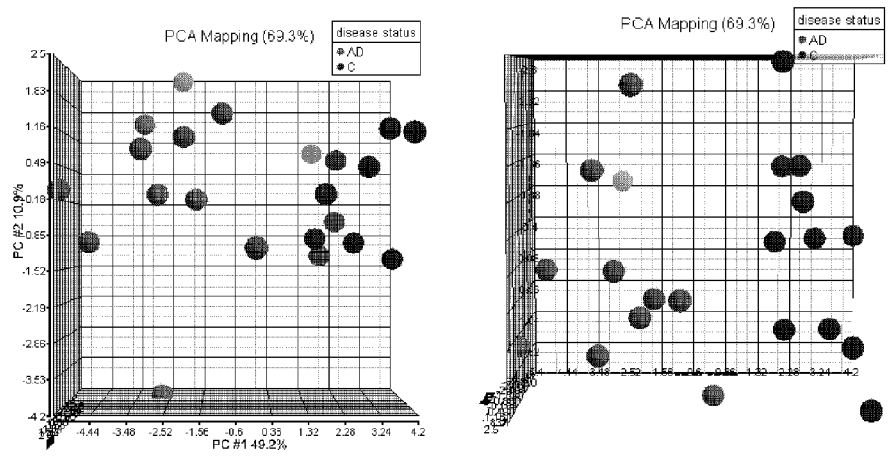
Figure 6:
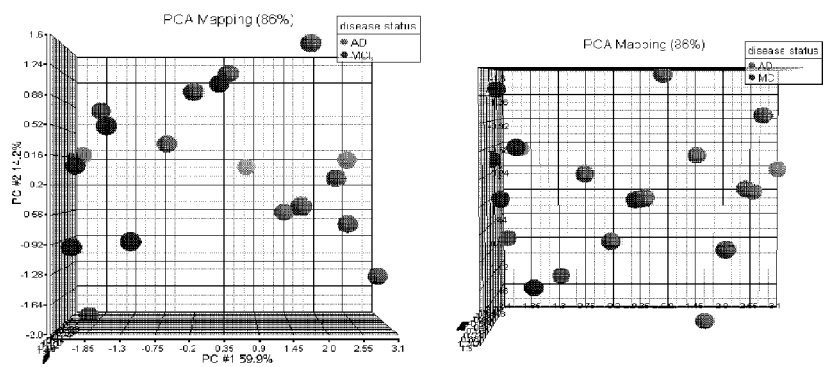
Figure 6:
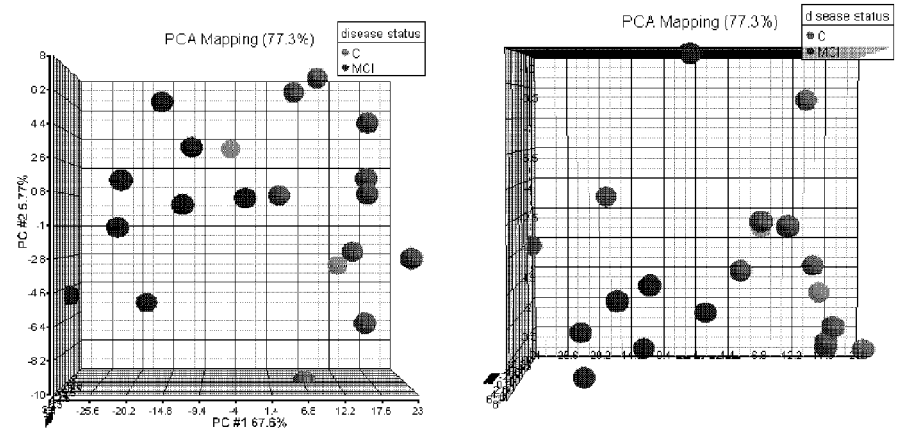

FIG. 6. Visualization of the patient distribution by Principal Component Analysis of MCI, AD or C patients from specifically selected sub-sets of groups of probes (robe sets, PS). FIG. 6A, discrimination between AD and C patients from a set of 18 probes; FIG. 6B, discrimination between MCI and AD patients from a set of 6 probes; FIG. 6C, discrimination between AD and C patients from a set of 373 probes.

TABLE LEGEND

Table 1. Table associated with 5578 target sequences (SEQ ID NO: 1-5578) and the different panels or subgroups. Column A: GWSA references for the target sequences. Column B: SEQ ID NO. Column C: Gene ID Number (Genbank). Columns D to F: Target sequences present (1) in pairs of groups TSP 1300 SS, TSP NN and TSP N. Columns G to BD. Panels 1 to 50. Columns BE to BG. Better target sequences from ANOVA analyses. Column BH. Targets associated with new isoforms of RT-PRC, SORL1 and PSEN1. Columns B1 to BN: Panels 55 to 60.

Table 2. Table associated with the best pairs of probe sets. Column A: GWSA references for the pairs. Column B: GWSA references for the first probe set in each pair. Column C: GWSA references of the second probe set in each pair. Column D: SEQ ID NO of the first probe set. Column E: SEQ ID NO of the second probe set. Column F: SEQ ID NO of both probe sets present in the pair (separated by "_" Column G: Score of TSP 1300 SS pairs. Column H: Score of TSP NN pairs. Column I: Score of TSP N pairs.

EXAMPLE 1

Identification of Serum Markers for Alzheimer's Disease 1.1. Characteristics of the Biological Samples The examples presented below were initially made from 150 blood samples (5 mL of whole blood, taken in two Pax-Gene tubes). These samples accounted for 80 patients diagnosed with Alzheimer's disease according to the DSM IV criteria. These patients corresponded to a mean age of 72.9 years (standard deviation: 5.5 years). These patients had a MMSE (Mini-Mental State Examination) below 20 (means score 13.7; standard deviation 6.7) and a GDS (Global Deterioration Scale) greater than or equal to 4. Furthermore, 70 subjects of comparable age to the AD patients, declared free of dementia after a clinical examination were also recruited (mean age 68.2 years with a standard deviation of 6.3 years; mean MMSE of 29.8 with a standard deviation of 0.4).

1.2. Extraction of Total RNA from the Blood Sample

The blood samples were collected directly in PAXGene™ Blood RNA tubes (PreAnalytix, Hombrechtikon, Switzerland). After the step of taking the blood and in order to obtain total cell lysis, the tubes were left at ambient temperature for 4 h and then kept at −20° C. until extraction of the biological material More precisely, in this protocol, the total RNA were extracted by means of PAXGene Blood RNA® kits (PreAnalytix) in accordance with the manufacturer's recommendations. Briefly, the tubes were centrifuged (15 min, 3000 g) in order to obtain a nucleic acid pellet. This pellet was washed and held in a buffer containing the proteinase K necessary for digesting the proteins (10 min at 55° C.). A new centrifugation (5 min, 19,000 g) was done to eliminate the cellular debris and ethanol was added in order to optimize the conditions for nucleic acid bonding. The total RNA were specifically bound on PAXgene RNA spin columns and, before their elution, the contaminant DNA were digested by means of an RNAse free DNAse set (Qiagen, Hilden, Germany). The quality and quantity of the total RNA extracted were evaluated by electrophoretograms by means of a Bioanalyser 2100 from Agilent by using the 600 NanoChip RNA kit (Agilent Technologies, Santa Clara, Calif.). Only the samples fulfilling the quality criteria were used for the final analyses.

1.3. The GWSA (Genome Wide SpliceArray) Microarray

The detection and quantification of the exhaustive expression of transcripts by microarray requires the use of a particular probe configuration. Every reference messenger RNA/splice variant pair can be modeled as long isoform/short isoform (FIG. 1A). Thus, a splice variant associated with an exon skip will be the short isoform with regard to the reference variant. A splice variant containing a new exon or retaining an intron will be the long isoform with regard to the reference variant. The other alternative splicing events (use of cryptic 5' or 3' splice sites) can also be modeled in the same way.

The probe set necessary for measuring the expression of splice variants is also indicated in FIG. 1A. This set is made up of three traditional "exon" probes F, T and B and three exon-exon or exon-intron junction probes C, D and E. Probes F and T measure the expression of both isoforms, probes B, C and D the expression of the long isoform and probe E the expression of the short isoform.

In order to design all these probes, it is necessary to identify the splicing events corresponding to human genes, then the "target" regions from which the probes will be designed. The target sequences corresponding to junction probes C, D and E are defined by a length of 30 nucleotides, 15 nucleotides from either side of the junction. It is thus possible to cover any junction by 25 nucleotide probes, for example: 11/14, 12/13, 13/12 (the/sign representing the junction zone).

The GWSA chip is a microarray that can provide very complete coverage of human genome expression by taking into account the existence of splice variants. 20,649 human genes were selected then analyzed to identify the associated known and potential splicing events. More than 90% of these genes could be associated with such events. Probes such as described above have been designed from a few of the 140,000 identified splicing events. Furthermore, the use of probes specific for splicing events corresponding to single exon skips also allows predicting the existence of such events (FIG. 1B). Moreover, the incorporation of junction probes covering each exon-exon, exon-intron and intron-exon region of each gene also allows characterizing the splicing events affecting the 5' and 3' ends of the exons (FIG. 1B). Three different probes have been designed per target sequence and combined in a "Probe Set". The expression values of the individual probes are consolidated into a Probe Set value. Sometimes, the Probe Set only contains 2 or even 1 probe if the target sequence restrictions are too constraining. The GWSA is a microarray built on the GeneChip® d'Affymetrix platform with a resolution of 5 microns. The GWSA underwent a quality control according to MAQC standards (Microarray Quality Control; Shi et al., Nat Biotechnol. 2006; 24(9): 1151-61).

1.4. RNA Amplification

Fifty ng of total RNA served as a matrix for the synthesis of targets by means of the WTOvation™ Pico RNA Amplification System kit (NuGen, San Carlos, Calif.). The FL-Ovation™ cDNA Biotin Module (NuGen, San Carlos, Calif.) was then used for the fragmentation of 5 μg of amplified cDNA as well as for the biotin labeling. The various steps were conducted by following the manufacturer's instructions. Each amplification/fragmentation/labeling series contained as many samples from AD patients as controls.

The quality and quantity of the total complementary DNA extracted were evaluated by electropherogram by means of a Bioanalyser 2100 from Agilent by using the 600 NanoChip RNA kit (Agilent Technologies, Santa Clara, Calif.).

1.5. Hybridization on the GWSA Array

Five μg of amplified and biotin-labeled cDNA are used per hybridization. The standard methods recommended by Affymetrix (Affymetrix, Santa Clara, Calif.) were applied for hybridization of the targets on the GWSA microarray. The DNA chips were then washed and the specific hybridization was visualized by following Affymetrix' recommendations. The hybridization signals were detected by means of a GeneChipR3000 7G scanner.

1.6. Data Extraction and Normalization

.CEL files obtained after scanning the slides were then imported into Partek Genomic Suites™ (Partek Incorporated, St Louis, Mich.) for quantile normalization of the arrays, background noise adjustment as a function of the GC composition of the oligonucleotide probes, background noise correction by RMA and consolidation of the expression values measured for each oligonucleotide in the probe set.

The data were then filtered with regard to the expression values of the probe sets; the expression level threshold was set at 3.8 (log 2 scale) based on the distribution frequency of the expression values on all the arrays.

1.7. Data Analysis for Signature Selection and Probe Normalization 1.7.1 Selection of signatures from the absolute expression of the probes.

A first group of 100 individuals (53 AD and 47 controls) was created among the 150 patients of the cohort for learning signature discriminant(s) by supervised clustering analyses using binary classification algorithms such as Support Vector Machine (SVM), K-Nearest Neighbor (KNN) and Linear Discriminant Analysis (LDA) and cross validation with partitions of 10 (Partek Genomic Suites™). Non-parametric tests (1-way and 2-way ANOVA) were conducted to analyze the expression values obtained per probe set and serve as a filtering tool for selecting the variables that will integrate the signature. A first signature of 170 markers was then characterized and evaluated in a group of independent test patients (see 8.1). Subsequently, 4 other learning groups were created to average a possible effect of the specific choice of a first learning group. Thus, 5 groups of 100 patients (53 AD and 47 controls) was created among the 150 patients of the cohort for learning signature discriminant(s) by supervised clustering analysis using binary classification algorithms such as Support Vector Machine (SVM), K-Nearest Neighbor (KNN) and Linear Discriminant Analysis (LDA) and cross validation with scores of 10 (Partek Genomic Suites™). Non-parametric tests (1-way and 2-way ANOVA) were conducted to analyze the expression values obtained per probe set and serve as a filtering tool for selecting the variables that will integrate the signature. The optimal classification model per learning group is then applied to the corresponding test group made up of 50 patients (27 AD and 23 controls) to identify the performances of the signature, i.e., specificity (% of correct classification of control patients) and sensitivity (% of correct classification of AD patients).

3770 models were tested in each learning group; the performances of each model were evaluated on all the learning groups. The models were then classified with regard to the mean of the performances over the 5 groups. The signatures presenting the highest performance means were selected to discriminate between patients with Alzheimer's disease and control patients without dementia.

1.7.2 Selection of Signatures from the Relative Expression of Probes Pairs.

This type of analysis, called TSP, consists of selecting probe sets in pairs whose relative expression is reversed between the two groups that are compared, AD and control (Geman et al., 2004 Stat Appl Genet Mol Biol 3: Article 19). The use of k pairs of probe sets is a variant called k-TSP (Tan et al., 2005 Bioinformatics 21: 3896-3904). For each gene, a list of all the probe set pairs is created. The expression levels of each probe set in a pair are compared per sample/microarray. The probability for the first probe set to have an expression level greater than the second is calculated for each of the AD and control groups. The difference of these two probabilities defines a score. The Top-Scoring Pair (TSP) or the k-Top Scoring-Pairs correspond to the best or to the k-best scores. A permutation analysis is then done 1000 times by defining two groups randomly from the same 150 individuals. The maximum score obtained by a pair among these 1000 permutations can then be compared to the best scores obtained from real AD and control pairs, making it possible to judge the statistical relevance of such scores.

1.7.3 Selection of the Normalization Probes

The normalization probe sets fulfill the following conditions:
  there is no statistically significant difference between AD and controls
  their variance is low before and after normalization
  the distribution of their intensities is comparable to the entire array after normalization The probe sets statistically significant for a difference between AD patients and control patients with a False Discovery Rate of 0.01 were eliminated from the normalized and non-normalized files containing the probe set expression values corresponding to the 150 patients filtered with a threshold value of 3.8 (log 2).

The variance was then calculated for each probe set from normalized and non-normalized files. The probe sets common to both files and having the lowest variance values were chosen.

These probe sets were classified by intensity according to the distribution of intensities measured on the normalized and filtered file. Probe sets were then selected in each intensity class with regard to decreasing p-values from the ANOVA statistical test.

EXAMPLE 2

Identification of Expression Profiles for Diagnosing Alzheimer's Disease from Blood Samples 2.1. Identification of an Expression Profile for Discriminating Control Patients with No Dementia (CND) from Patients with Alzheimer's Disease (AD).

The expression of the entire human transcriptome, representing approximately 21,000 genes, has been analyzed and compared between AD and CND patients by means of the GWSA microarray. All the analyses discussed in sections 7.1 and 7.2 has allowed identifying a collection of 5578 target sequences, pertinent according to the invention (see Table 1, SEQ ID Nos: 1-5578).

These sequences are partially composed of three groups of probe sets coming from ANOVA analyses of one or two parameters (1-way or 2-way).

More precisely, it is group or panel 51 (Table 1) represented by SEQ ID NO: 16; 18; 19; 21; 22; 38; 39; 40; 41; 42; 43; 44; 45; 46; 47; 48; 62; 67; 73; 79; 80; 83; 84; 86; 88; 89; 94; 108; 109; 110; 113; 119; 125; 126; 127; 128; 143; 150; 156; 157; 164; 165; 175; 178; 179; 180; 182; 187; 190; 191; 213; 260; 261; 262; 263; 271; 272; 275; 281; 284; 294; 295; 308; 310; 311; 312; 313; 314; 321; 322; 323; 327; 337; 341; 343; 347; 348; 350; 351; 353; 355; 356; 357; 362; 366; 370; 372; 376; 377; 378; 379; 388; 394; 396; 399; 400; 402; 404; 405; 406; 408; 409; 410; 413; 416; 421; 423; 425; 426; 441; 442; 443; 444; 445; 446; 448; 449; 450; 451; 452; 453; 454; 455; 456; 457; 458; 462; 465; 466; 467; 468; 469; 470; 471; 472; 473; 474; 475; 501; 502; 503; 513; 514; 515; 519; 520; 523; 524; 528; 532; 533; 535; 537; 540; 541; 543; 547; 556; 565; 566; 567; 568; 572; 581; 582; 583; 590; 592; 595; 600; 602; 603; 606; 607; 608; 609; 613; 618; 620; 634; 635; 636; 637; 641; 646; 647; 654; 655; 656; 657; 659; 660; 663; 667; 669; 676; 684; 686; 687; 688; 695; 696; 704; 705; 706; 707; 709; 710; 713; 720; 731; 732; 737; 739; 742; 754; 760; 769; 775; 776; 778; 782; 783; 784; 785; 786; 787; 790; 796; 808; 809; 810; 811; 826; 833; 836; 839; 852; 857; 867; 868; 891; 912; 913; 914; 915; 916; 922; 923; 924; 925; 927; 928; 930; 931; 932; 933; 934; 935; 936; 940; 948; 950; 951; 952; 956; 957; 976; 977; 978; 979; 980; 982; 983; 984; 985; 986; 988; 1014; 1015; 1016; 1017; 1019; 1020; 1029; 1030; 1031; 1037; 1040; 1041; 1042; 1046; 1049; 1075; 1076; 1077; 1078; 1079; 1080; 1095; 1096; 1100; 1101; 1106; 1108; 1109; 1110; 1112; 1113; 1114; 1115; 1116; 1121; 1140; 1145; 1148; 1149; 1152; 1154; 1156; 1158; 1163; 1164; 1165; 1167; 1169; 1171; 1172; 1173; 1175; 1178; 1179; 1186; 1187; 1191; 1207; 1215; 1230; 1239; 1241; 1260; 1277; 1278; 1286; 1294; 1304; 1309; 1332; 1333; 1354; 1355; 1356; 1357; 1358; 1359; 1361; 1366; 1395; 1396; 1408; 1415; 1416; 1420; 1422; 1428; 1439; 1445; 1472; 1473; 1474; 1484; 1487; 1489; 1490; 1493; 1498; 1509; 1510; 1512; 1513; 1515; 1516; 1517; 1518; 1520; 1521; 1525; 1526; 1527; 1528; 1529; 1530; 1532; 1533; 1535; 1560; 1562; 1563; 1566; 1575; 1576; 1577; 1578; 1579; 1580; 1581; 1582; 1583; 1584; 1589; 1597; 1598; 1599; 1600; 1619; 1621; 1623; 1627; 1634; 1635; 1639; 1640; 1649; 1651; 1652; 1653; 1669; 1670; 1671; 1672; 1673; 1675; 1680; 1689; 1694; 1696; 1697; 1709; 1710; 1713; 1717; 1721; 1722; 1725; 1729; 1732; 1734; 1741; 1742; 1743; 1744; 1747; 1748; 1749; 1753; 1756; 1762; 1763; 1764; 1765; 1770; 1771; 1772; 1773; 1774; 1775; 1776; 1779; 1780; 1781; 1785; 1787; 1788; 1790; 1791; 1792; 1793; 1794; 1800; 1801; 1802; 1805; 1824; 1825; 1826; 1827; 1828; 1829; 1830; 1831; 1833; 1834; 1837; 1839; 1840; 1844; 1845; 1847; 1851; 1855; 1856; 1857; 1858; 1861; 1862; 1910; 1913; 1914; 1915; 1916; 1917; 1918; 1919; 1935; 1938; 1942; 1946; 1947; 1948; 1950; 1952; 1953; 1956; 1961; 1966; 1969; 1971; 1972; 1976; 1977; 1978; 1983; 1984; 1995; 1996; 1999; 2000; 2002; 2012; 2020; 2021; 2025; 2041; 2045; 2047; 2050; 2051; 2060; 2063; 2064; 2087; 2088; 2090; 2093; 2097; 2098; 2099; 2102; 2109; 2113; 2127; 2128; 2129; 2130; 2132; 2135; 2136; 2143; 2144; 2159; 2160; 2161; 2164; 2166; 2177; 2178; 2182; 2204; 2214; 2215; 2216; 2217; 2235; 2241; 2242; 2243; 2267; 2268; 2270; 2271; 2272; 2278; 2279; 2283; 2305; 2306; 2311; 2312; 2313; 2314; 2315; 2316; 2317; 2318; 2319; 2321; 2322; 2323; 2324; 2325; 2326; 2327; 2328; 2331; 2332; 2336; 2341; 2343; 2344; 2346; 2347; 2348; 2361; 2362; 2368; 2371; 2372; 2373; 2375; 2376; 2377; 2379; 2380; 2381; 2382; 2383; 2384; 2389; 2391; 2392; 2395; 2396; 2397; 2399; 2405; 2406; 2407; 2408; 2409; 2410; 2411; 2412; 2413; 2414; 2415; 2417; 2418; 2441; 2443; 2444; 2445; 2446; 2447; 2451; 2456; 2458; 2460; 2465; 2469; 2472; 2486; 2493; 2494; 2520; 2521; 2524; 2526; 2527; 2528; 2529; 2530; 2531; 2532; 2533; 2534; 2536; 2538; 2539; 2543; 2556; 2563; 2577; 2578; 2579; 2582; 2583; 2584; 2586; 2587; 2588; 2589; 2590; 2591; 2592; 2600; 2601; 2603; 2606; 2612; 2613; 2616; 2617; 2618; 2636; 2648; 2658; 2660; 2676; 2679; 2680; 2684; 2691; 2692; 2694; 2695; 2696; 2697; 2698; 2699; 2700; 2701; 2702; 2703; 2725; 2727; 2728; 2740; 2741; 2742; 2743; 2762; 2763; 2765; 2770; 2771; 2772; 2773; 2775; 2776; 2783; 2791; 2793; 2795; 2796; 2800; 2803; 2804; 2809; 2810; 2828; 2843; 2844; 2850; 2851; 2852; 2853; 2860; 2862; 2863; 2865; 2867; 2871; 2872; 2874; 2879; 2886; 2890; 2892; 2893; 2894; 2895; 2897; 2898; 2899; 2902; 2904; 2905; 2906; 2907; 2909; 2910; 2914; 2915; 2916; 2917; 2919; 2920; 2922; 2924; 2925; 2930; 2933; 2934; 2935; 2936; 2937; 2938; 2939; 2940; 2941; 2943; 2944; 2945; 2946; 2947; 2950; 2951; 2953; 2954; 2983; 2991; 2997; 3018; 3028; 3035; 3036; 3037; 3041; 3042; 3043; 3055; 3056; 3057; 3061; 3065; 3073; 3074; 3075; 3076; 3085; 3086; 3089; 3102; 3105; 3108; 3109; 3110; 3111; 3118; 3150; 3161; 3164; 3165; 3166; 3167; 3175; 3188; 3191; 3194; 3195; 3196; 3205; 3207; 3215; 3219; 3221; 3223; 3224; 3225; 3226; 3233; 3234; 3235; 3252; 3260; 3270; 3273; 3277; 3280; 3285; 3286; 3297; 3298; 3301; 3302; 3303; 3307; 3308; 3310; 3311; 3312; 3314; 3315; 3322; 3323; 3324; 3326; 3330; 3335; 3341; 3344; 3345; 3346; 3349; 3350; 3358; 3360; 3361; 3362; 3366; 3373; 3377; 3378; 3379; 3380; 3384; 3406; 3409; 3410; 3411; 3412; 3413; 3420; 3421; 3427; 3428; 3434; 3442; 3443; 3452; 3461; 3474; 3480; 3483; 3487; 3489; 3490; 3491; 3495; 3500; 3505; 3507; 3509; 3517; 3521; 3523; 3524; 3532; 3534; 3536; 3539; 3541; 3542; 3553; 3558; 3559; 3562; 3563; 3564; 3572; 3574; 3576; 3577; 3578; 3579; 3581; 3582; 3583; 3586; 3587; 3588; 3595; 3596; 3597; 3598; 3599; 3600; 3601; 3602; 3607; 3608; 3609; 3610; 3615; 3627; 3628; 3629; 3632; 3639; 3646; 3649; 3650; 3657; 3671; 3673; 3696; 3705; 3707; 3708; 3709; 3732; 3733; 3743; 3748; 3751; 3752; 3753; 3758; 3761; 3762; 3772; 3773; 3775; 3776; 3777; 3778; 3783; 3789; 3790; 3793; 3796; 3799; 3806; 3808; 3819; 3820; 3849; 3853; 3855; 3856; 3857; 3859; 3862; 3863; 3864; 3871; 3884; 3889; 3890; 3912; 3913; 3915; 3919; 3920; 3921; 3929; 3931; 3932; 3934; 3937; 3938; 3939; 3940; 3943; 3944; 3950; 3951; 3952; 3953; 3955; 3956; 3958; 3961; 3962; 3963; 3964; 3965; 3969; 3973; 3974; 3977; 3990; 3991; 3992; 3995; 4001; 4004; 4005; 4006; 4009; 4010; 4011; 4012; 4014; 4015; 4051; 4053; 4054; 4063; 4064; 4070; 4078; 4091; 4092; 4093; 4095; 4096; 4097; 4111; 4115; 4119; 4121; 4154; 4158; 4170; 4171; 4175; 4193; 4198; 4200; 4201; 4202; 4206; 4207; 4208; 4209; 4219; 4221; 4222; 4227; 4228; 4229; 4230; 4232; 4234; 4255; 4260; 4266; 4280; 4282; 4292; 4293; 4296; 4297; 4298; 4299; 4300; 4306; 4307; 4308; 4309; 4312; 4316; 4327; 4330; 4331; 4336; 4337; 4340; 4341; 4342; 4343; 4344; 4345; 4346; 4347; 4348; 4349; 4350; 4351; 4352; 4357; 4358; 4364; 4365; 4378; 4379; 4380; 4386; 4398; 4399; 4400; 4426; 4430; 4431; 4432; 4435; 4438;

4469; 4472; 4475; 4476; 4482; 4488; 4492; 4499; 4505; 4506; 4532; 4547; 4548; 4549; 4550; 4551; 4554; 4555; 4556; 4558; 4559; 4582; 4592; 4593; 4594; 4595; 4603; 4607; 4609; 4611; 4612; 4613; 4617; 4618; 4619; 4621; 4623; 4624; 4629; 4656; 4661; 4662; 4663; 4666; 4671; 4672; 4674; 4675; 4676; 4677; 4678; 4679; 4684; 4693; 4694; 4695; 4698; 4710; 4713; 4718; 4732; 4733; 4734; 4735; 4738; 4744; 4749; 4765; 4768; 4769; 4771; 4779; 4780; 4781; 4782; 4783; 4789; 4790; 4798; 4799; 4805; 4808; 4809; 4810; 4812; 4813; 4816; 4823; 4824; 4826; 4827; 4828; 4831; 4833; 4851; 4856; 4859; 4860; 4861; 4862; 4865; 4867; 4868; 4869; 4873; 4874; 4876; 4883; 4884; 4896; 4905; 4908; 4909; 4910; 4917; 4920; 4921; 4922; 4923; 4924; 4926; 4927; 4928; 4929; 4932; 4933; 4934; 4935; 4938; 4943; 4944; 4946; 4948; 4949; 4951; 4952; 4953; 4954; 4955; 4957; 4958; 4960; 4962; 4964; 4966; 4967; 4970; 4973; 4980; 4985; 4987; 4998; 5000; 5001; 5004; 5011; 5012; 5015; 5016; 5017; 5018; 5020; 5022; 5024; 5025; 5026; 5029; 5030; 5031; 5037; 5038; 5039; 5041; 5042; 5043; 5044; 5045; 5046; 5047; 5048; 5052; 5053; 5055; 5057; 5058; 5061; 5067; 5069; 5080; 5084; 5096; 5098; 5099; 5100; 5101; 5104; 5109; 5111; 5112; 5116; 5122; 5133; 5134; 5135; 5136; 5137; 5138; 5139; 5140; 5144; 5145; 5146; 5154; 5155; 5157; 5158; 5159; 5160; 5163; 5165; 5166; 5167; 5174; 5175; 5180; 5182; 5186; 5188; 5190; 5191; 5195; 5196; 5197; 5198; 5199; 5200; 5202; 5203; 5204; 5206; 5209; 5210; 5211; 5212; 5221; 5231; 5238; 5239; 5244; 5245; 5246; 5247; 5254; 5257; 5265; 5269; 5271; 5288; 5290; 5317; 5325; 5329; 5335; 5336; 5337; 5353; 5365; 5370; 5372; 5374; 5376; 5380; 5383; 5384; 5396; 5407; 5408; 5409; 5410; 5411; 5412; 5413; 5414; 5415; 5425; 5428; 5439; 5440; 5441; 5443; 5465; 5466; 5469; 5494; 5495; 5499; 5500; 5518; 5520; 5521; 5522; 5523; 5524; 5525; 5528; 5530; 5531; 5532; 5533; 5534; 5535; 5537; 5538; 5539; 5540; 5553; 5555; 5564; 5569; 5575; 5576; 5577

All these probe sets have a p-value (AD vs. control) less than $3.19\ e^{-08}$

It is also the second or group or panel 52 represented by SEQ ID NO: 1; 6; 8; 28; 59; 60; 61; 83; 90; 91; 121; 133; 181; 182; 224; 311; 314; 321; 323; 331; 339; 340; 342; 343; 354; 356; 397; 417; 418; 420; 429; 446; 449; 453; 455; 473; 522; 538; 596; 598; 600; 601; 604; 611; 613; 636; 638; 661; 690; 696; 720; 724; 738; 742; 762; 788; 845; 852; 926; 939; 990; 1050; 1146; 1150; 1151; 1152; 1153; 1154; 1160; 1185; 1203; 1206; 1214; 1215; 1237; 1239; 1242; 1322; 1326; 1357; 1394; 1397; 1398; 1413; 1414; 1422; 1489; 1490; 1501; 1511; 1531; 1539; 1552; 1559; 1588; 1592; 1609; 1637; 1641; 1650; 1658; 1671; 1675; 1683; 1692; 1694; 1695; 1699; 1702; 1711; 1723; 1729; 1730; 1731; 1740; 1741; 1742; 1743; 1744; 1747; 1749; 1756; 1789; 1800; 1806; 1831; 1832; 1833; 1834; 1836; 1837; 1850; 1853; 1859; 1939; 1951; 1964; 1972; 1985; 1994; 1995; 1999; 2022; 2023; 2024; 2038; 2060; 2061; 2062; 2068; 2073; 2078; 2081; 2086; 2090; 2091; 2111; 2116; 2117; 2118; 2119; 2120; 2121; 2122; 2123; 2124; 2125; 2126; 2127; 2128; 2129; 2130; 2132; 2133; 2143; 2144; 2146; 2147; 2148; 2169; 2187; 2190; 2191; 2192; 2195; 2196; 2209; 2284; 2351; 2352; 2353; 2358; 2360; 2365; 2366; 2367; 2369; 2370; 2371; 2372; 2374; 2375; 2378; 2380; 2382; 2394; 2399; 2402; 2411; 2412; 2435; 2454; 2458; 2459; 2461; 2462; 2465; 2469; 2472; 2488; 2489; 2490; 2518; 2528; 2529; 2532; 2533; 2534; 2536; 2538; 2542; 2543; 2544; 2545; 2546; 2548; 2556; 2557; 2558; 2559; 2561; 2563; 2564; 2575; 2585; 2590; 2642; 2649; 2652; 2659; 2679; 2684; 2692; 2695; 2703; 2708; 2709; 2710; 2714; 2724; 2725; 2727; 2729; 2732; 2740; 2745; 2790; 2811; 2813; 2865; 2887; 2888; 2900; 2902; 2908; 2921; 2928; 2941; 2942; 2943; 2944; 2975; 2976; 2983; 3001; 3014; 3018; 3023; 3043; 3045; 3057; 3092; 3104; 3171; 3172; 3173; 3192; 3206; 3211; 3216; 3221; 3243; 3271; 3286; 3301; 3304; 3312; 3325; 3333; 3356; 3365; 3384; 3387; 3388; 3389; 3427; 3429; 3483; 3487; 3491; 3500; 3520; 3526; 3533; 3554; 3559; 3574; 3580; 3600; 3673; 3685; 3686; 3688; 3690; 3692; 3706; 3741; 3751; 3763; 3782; 3805; 3806; 3807; 3808; 3809; 3810; 3811; 3812; 3813; 3819; 3820; 3821; 3822; 3823; 3857; 3859; 3862; 3867; 3904; 3906; 3909; 3920; 3930; 3936; 3940; 3950; 3958; 3961; 3985; 4012; 4013; 4015; 4019; 4076; 4091; 4093; 4094; 4096; 4124; 4130; 4200; 4265; 4295; 4297; 4343; 4345; 4350; 4351; 4352; 4398; 4428; 4434; 4442; 4468; 4471; 4476; 4478; 4479; 4493; 4494; 4497; 4498; 4501; 4510; 4515; 4525; 4546; 4583; 4584; 4591; 4592; 4598; 4603; 4659; 4676; 4706; 4710; 4733; 4737; 4744; 4780; 4793; 4797; 4799; 4804; 4806; 4807; 4860; 4879; 4885; 4887; 4888; 4889; 4890; 4891; 4892; 4895; 4896; 4897; 4898; 4899; 4905; 4907; 4918; 4944; 4955; 4968; 4969; 4975; 4976; 4977; 4978; 4979; 4982; 4999; 5000; 5028; 5031; 5059; 5080; 5125; 5144; 5156; 5170; 5188; 5195; 5196; 5198; 5206; 5221; 5237; 5238; 5245; 5246; 5247; 5249; 5254; 5257; 5285; 5289; 5305; 5320; 5333; 5363; 5371; 5379; 5380; 5383; 5398; 5416; 5421; 5450; 5498; 5501; 5529; 5534; 5535; 5538; 5555; 5562

All these probe sets have a p-value (AD vs. control) less than $1.17\ e^{-12}$

It is also a third or group or panel 53 represented by SEQ ID NO: 15; 17; 20; 25; 26; 50; 51; 52; 58; 66; 75; 87; 98; 99; 101; 103; 105; 114; 115; 116; 117; 118; 120; 166; 167; 171; 173; 216; 278; 285; 300; 325; 338; 354; 365; 371; 397; 398; 403; 407; 424; 459; 473; 476; 482; 506; 509; 510; 511; 516; 517; 518; 521; 527; 536; 539; 569; 570; 571; 591; 593; 597; 598; 599; 614; 617; 619; 629; 661; 664; 666; 668; 677; 689; 690; 692; 693; 694; 711; 721; 722; 726; 751; 768; 777; 788; 789; 791; 842; 869; 872; 893; 894; 895; 896; 905; 921; 1032; 1033; 1043; 1044; 1045; 1070; 1147; 1155; 1157; 1159; 1161; 1162; 1168; 1170; 1174; 1185; 1218; 1220; 1225; 1226; 1229; 1237; 1238; 1239; 1240; 1242; 1253; 1254; 1258; 1259; 1268; 1270; 1346; 1348; 1349; 1362; 1364; 1365; 1401; 1417; 1421; 1432; 1440; 1491; 1494; 1495; 1496; 1522; 1524; 1561; 1588; 1616; 1617; 1618; 1622; 1630; 1632; 1654; 1667; 1668; 1674; 1691; 1692; 1700; 1701; 1718; 1744; 1767; 1784; 1786; 1798; 1807; 1808; 1809; 1810; 1811; 1812; 1813; 1814; 1815; 1816; 1834; 1838; 1841; 1843; 1853; 1859; 1912; 1920; 1951; 1986; 2001; 2008; 2009; 2010; 2011; 2023; 2042; 2085; 2096; 2106; 2107; 2108; 2110; 2111; 2112; 2114; 2115; 2128; 2134; 2137; 2139; 2140; 2141; 2143; 2144; 2148; 2158; 2165; 2167; 2168; 2203; 2207; 2218; 2226; 2246; 2247; 2248; 2249; 2250; 2251; 2252; 2253; 2254; 2255; 2256; 2258; 2260; 2261; 2263; 2264; 2265; 2266; 2269; 2280; 2281; 2307; 2310; 2320; 2329; 2340; 2345; 2350; 2393; 2401; 2411; 2421; 2436; 2442; 2450; 2462; 2517; 2543; 2555; 2560; 2594; 2599; 2602; 2619; 2620; 2621; 2622; 2632; 2633; 2638; 2695; 2714; 2727; 2788; 2789; 2816; 2817; 2818; 2822; 2823; 2824; 2825; 2827; 2831; 2838; 2869; 2870; 2887; 2888; 2889; 2896; 2900; 2903; 2932; 2943; 2979; 2982; 2985; 2994; 3005; 3053; 3066; 3087; 3106; 3107; 3153; 3156; 3157; 3158; 3159; 3160; 3180; 3185; 3186; 3200; 3211; 3217; 3218; 3222; 3266; 3268; 3278; 3279; 3281; 3304; 3305; 3309; 3313; 3317; 3338; 3374; 3375; 3381; 3430; 3462; 3502; 3506; 3508; 3518; 3519; 3520; 3522; 3525; 3527; 3530; 3531; 3535; 3540; 3567; 3573; 3623; 3624; 3625;

3626; 3670; 3672; 3685; 3713; 3734; 3759; 3771; 3782; 3786; 3804; 3814; 3815; 3816; 3824; 3826; 3828; 3829; 3830; 3842; 3843; 3844; 3847; 3848; 3851; 3870; 3872; 3895; 3896; 3897; 3898; 3954; 3960; 3966; 3967; 3968; 3972; 3975; 3976; 3978; 3987; 3993; 4008; 4094; 4096; 4112; 4125; 4164; 4172; 4184; 4185; 4192; 4223; 4233; 4269; 4281; 4359; 4370; 4371; 4375; 4381; 4388; 4398; 4419; 4425; 4427; 4428; 4429; 4433; 4470; 4481; 4483; 4493; 4495; 4502; 4507; 4509; 4553; 4575; 4581; 4610; 4622; 4658; 4660; 4664; 4665; 4688; 4692; 4711; 4712; 4714; 4716; 4722; 4791; 4792; 4857; 4865; 4872; 4959; 4961; 4965; 4974; 4981; 4988; 5019; 5021; 5023; 5027; 5049; 5060; 5065; 5066; 5087; 5107; 5108; 5110; 5119; 5123; 5141; 5164; 5173; 5176; 5181; 5183; 5184; 5185; 5187; 5189; 5198; 5206; 5238; 5241; 5270; 5272; 5273; 5338; 5350; 5391; 5417; 5429; 5434; 5435; 5513; 5529; 5578

All these probe sets have a p-value (AD vs. control) less than $6.70\ e^{-15}$

The inventors then studied the simultaneous expression of probe sets associated with sub-sets of these 5578 sequences to obtain relevant expression profiles for Alzheimer's disease. A randomized learning group of 100 individuals (53 AD and 47 NDC) and an SVM classification algorithm allowed identifying a signature composed of 170 Probe Sets corresponding to panel 50 (Table 1) and to SEQ ID NO:
20; 25; 26; 51; 52; 58; 87; 98; 100; 101; 102; 103; 104; 105; 115; 166; 173; 174; 216; 278; 354; 374; 382; 397; 398; 407; 511; 518; 569; 570; 571; 614; 629; 664; 666; 668; 693; 711; 721; 725; 751; 757; 842; 869; 895; 987; 989; 1033; 1161; 1218; 1229; 1237; 1238; 1240; 1242; 1258; 1259; 1270; 1287; 1346; 1347; 1348; 1362; 1408; 1522; 1590; 1654; 1668; 1694; 1701; 1767; 1786; 1798; 1808; 1809; 1811; 1812; 1813; 1815; 1843; 1859; 1920; 1986; 2008; 2009; 2010; 2011; 2023; 2085; 2110; 2111; 2115; 2218; 2226; 2247; 2256; 2263; 2269; 2281; 2350; 2393; 2411; 2436; 2620; 2788; 2789; 2900; 2943; 2978; 2979; 2993; 2994; 3050; 3103; 3158; 3217; 3266; 3282; 3375; 3508; 3524; 3527; 3531; 3538; 3540; 3552; 3625; 3685; 3713; 3782; 3841; 3898; 3957; 3960; 3966; 3975; 3993; 4007; 4093; 4094; 4096; 4194; 4223; 4370; 4381; 4429; 4433; 4470; 4481; 4483; 4493; 4553; 4560; 4688; 4714; 4716; 4722; 5049; 5107; 5108; 5181; 5183; 5184; 5185; 5198; 5206; 5254; 5391; 5468; 5549

The performances of this signature were evaluated on a TEST collection of individuals who did not participate in defining this signature. This TEST group included 27 AD and 23 NDC. The performances obtained are: a sensitivity of 100% and a specificity of 96%, i.e., 27 AD out of 27 were properly classified as AD by the signature of panel 50 and 22 NDC out of 23 were properly classified as NDC by the signature of panel 50. A principal component analysis allows visualizing the separation of the AD group from the control group (FIG. 2). The 170 markers for this signature correspond to 133 genes. Thirty-one of the 170 probe sets are specifically associated with splice events, mainly new exons and exon skips. RT-PCR experiments confirmed the presence of certain of these transcripts generated by alternative splicing.

The directory of some of the 133 genes provides a precise molecular base, not predictable with certain phenomena described in Alzheimer's disease: activation of macrophages, TGF-beta signaling pathway, oxidative stress, innate immunity, inflammation, cytoskeleton reorganization, involvement of lipid rafts, particularly through cholesterol and sphingolipid signaling pathways, and involvement of the ubiquitin-proteasome system.

2.2. Characterization of Subpanels of Panel 50 and Associated Performances

The inventors also studied the simultaneous expression of sub-sets of 100, 50 and 25 probe sets from the 170 probe sets associated with panel 50.

2.2.1. Characterization of a Panel of 100 Markers (PANEL 49)

The inventors have demonstrated a combination of 100 markers, based on the sequences SEQ ID Nos: 20; 25; 26; 51; 52; 58; 87; 98; 100; 101; 102; 103; 104; 105; 115; 166; 173; 174; 216; 278; 354; 374; 382; 397; 398; 407; 511; 518; 569; 570; 571; 614; 629; 664; 666; 668; 693; 711; 721; 725; 751; 757; 842; 869; 895; 987; 989; 1033; 1161; 1218; 1229; 1237; 1238; 1240; 1242; 1258; 1259; 1270; 1287; 1346; 1347; 1348; 1362; 1408; 1522; 1590; 1654; 1668; 1694; 1701; 1767; 1786; 1798; 1808; 1809; 1811; 1812; 1813; 1815; 1843; 1859; 1920; 1986; 2008; 2009; 2010; 2011; 2023; 2085; 2110; 2111; 2115; 2218; 2226; 2247; 2256; 2263; 2269; 2281; 2350 (see Table 1).

This combination produced a sensitivity of 81% and a specificity of 91% on the TEST group.

2.2.2. Characterization of a Panel of 50 Markers (PANEL 48)

The inventors have demonstrated a combination of 50 markers, based on the sequences SEQ ID Nos: 20; 25; 26; 51; 52; 58; 87; 98; 100; 101; 102; 103; 104; 105; 115; 166; 173; 174; 216; 278; 354; 374; 382; 397; 398; 407; 511; 518; 569; 570; 571; 614; 629; 664; 666; 668; 693; 711; 721; 725; 751; 757; 842; 869; 895; 987; 989; 1033; 1161; 1218 (see Table 1).

This combination produced a sensitivity of 70% and a specificity of 87% on the TEST group.

2.2.3. Characterization of a Panel of 25 Markers (PANEL 47)

The inventors have demonstrated a combination of 25 markers, based on the sequences SEQ ID Nos: 20; 25; 26; 51; 52; 58; 87; 98; 100; 101; 102; 103; 104; 105; 115; 166; 173; 174; 216; 278; 354; 374; 382; 397; 398 (see Table 1).

This combination produced a sensitivity of 89% and a specificity of 61% on the TEST group.

These elements indicate that these sub-signatures retain a diagnostic power that is nevertheless inferior to the parent signature of 170 markers of panel 50.

The inventors then characterized different marker panels from 5 different learning/test groups that will now be described in sections 8.3 to 8.54.

2.3. Identification of a Predictive Panel of 160 Markers (PANEL 1)

The inventors have demonstrated a combination of 160 markers, linked to a KNN algorithm, based on the sequences SEQ ID Nos: 1; 28; 73; 321; 323; 350; 397; 417; 418; 612; 720; 852; 990; 991; 1152; 1154; 1169; 1212; 1237; 1239; 1242; 1326; 1489; 1490; 1641; 1683; 1694; 1711; 1723; 1731; 1741; 1744; 1747; 1749; 1800; 1831; 1833; 1834; 1837; 1951; 1952; 1953; 1984; 1995; 2023; 2038; 2117; 2126; 2127; 2128; 2129; 2130; 2133; 2144; 2284; 2305; 2365; 2372; 2378; 2380; 2382; 2399; 2411; 2458; 2459; 2462; 2528; 2529; 2532; 2533; 2534; 2538; 2542; 2543; 2556; 2563; 2564; 2652; 2679; 2703; 2708; 2709; 2725; 2727; 2732; 2740; 2887; 2888; 2900; 2941; 2943; 2944; 3043; 3057; 3092; 3286; 3384; 3387; 3596; 3600; 3690; 3782; 3810; 3811; 3822; 3857; 3904; 3920; 3940; 3958; 4076; 4093; 4094; 4096; 4130; 4295; 4297; 4345; 4351; 4428; 4434; 4442; 4468; 4493; 4510; 4515; 4546; 4596; 4603; 4706; 4736; 4744; 4804; 4860; 4885; 4888; 4889; 4890; 4891; 4892; 4897; 4898; 4899; 4918; 4955; 4975; 4976; 4978; 4982; 5067; 5080; 5144; 5198; 5221; 5238; 5380; 5383; 5450; 5532; 5555 (see Table 1).

This combination permits correctly classifying 93.3% of the samples.

2.4. Identification of a Predictive Panel of 280 Markers (PANEL 2)

The inventors have demonstrated a combination of 280 markers, linked to a KNN algorithm, based on the sequences SEQ ID Nos: 1; 6; 8; 28; 73; 80; 84; 90; 224; 314; 321; 323; 331; 343; 345; 349; 350; 352; 397; 417; 418; 429; 513; 538; 542; 600; 612; 629; 720; 723; 724; 738; 742; 788; 852; 978; 990; 991; 1107; 1152; 1154; 1169; 1212; 1237; 1239; 1242; 1260; 1295; 1326; 1489; 1490; 1511; 1641; 1683; 1694; 1711; 1714; 1723; 1731; 1732; 1741; 1744; 1747; 1749; 1789; 1800; 1806; 1831; 1833; 1834; 1836; 1837; 1859; 1861; 1950; 1951; 1952; 1953; 1984; 1985; 1994; 1995; 2022; 2023; 2038; 2090; 2091; 2117; 2126; 2127; 2128; 2129; 2130; 2132; 2133; 2143; 2144; 2192; 2209; 2284; 2305; 2365; 2372; 2374; 2375; 2378; 2380; 2382; 2390; 2399; 2406; 2411; 2458; 2459; 2462; 2469; 2528; 2529; 2532; 2533; 2534; 2538; 2542; 2543; 2556; 2562; 2563; 2564; 2575; 2652; 2679; 2703; 2708; 2709; 2725; 2727; 2732; 2740; 2743; 2812; 2879; 2887; 2888; 2900; 2941; 2942; 2943; 2944; 2975; 3001; 3018; 3043; 3056; 3057; 3061; 3070; 3092; 3173; 3221; 3242; 3265; 3286; 3384; 3387; 3388; 3429; 3487; 3500; 3520; 3574; 3576; 3596; 3600; 3673; 3688; 3690; 3732; 3751; 3767; 3782; 3807; 3809; 3810; 3811; 3819; 3820; 3822; 3857; 3862; 3904; 3920; 3936; 3940; 3950; 3958; 3985; 4017; 4019; 4051; 4076; 4093; 4094; 4096; 4130; 4295; 4297; 4345; 4350; 4351; 4399; 4428; 4434; 4442; 4468; 4493; 4497; 4510; 4515; 4523; 4546; 4592; 4596; 4603; 4607; 4676; 4706; 4736; 4744; 4804; 4807; 4860; 4885; 4886; 4887; 4888; 4889; 4890; 4891; 4892; 4895; 4897; 4898; 4899; 4918; 4955; 4975; 4976; 4978; 4979; 4982; 5000; 5017; 5031; 5067; 5080; 5109; 5125; 5144; 5147; 5188; 5196; 5198; 5221; 5238; 5247; 5249; 5305; 5333; 5373; 5380; 5383; 5416; 5450; 5501; 5519; 5521; 5529; 5532; 5534; 5555 (see Table 1).

This combination permits correctly classifying 93.0% of the samples.

2.5. Identification of a Predictive Panel of 260 Markers (PANEL 3)

The inventors have demonstrated a combination of 260 markers, linked to a KNN algorithm, based on the sequences SEQ ID Nos: 1; 6; 8; 28; 73; 80; 84; 90; 224; 314; 321; 323; 331; 343; 345; 349; 350; 352; 397; 417; 418; 429; 513; 538; 542; 600; 612; 629; 720; 723; 738; 742; 788; 852; 978; 990; 991; 1152; 1154; 1169; 1212; 1237; 1239; 1242; 1295; 1326; 1489; 1490; 1511; 1641; 1683; 1694; 1711; 1714; 1723; 1731; 1732; 1741; 1744; 1747; 1749; 1789; 1800; 1806; 1831; 1833; 1834; 1836; 1837; 1859; 1861; 1950; 1951; 1952; 1953; 1984; 1985; 1994; 1995; 2023; 2038; 2090; 2091; 2117; 2126; 2127; 2128; 2129; 2130; 2132; 2133; 2143; 2144; 2209; 2284; 2305; 2365; 2372; 2374; 2375; 2378; 2380; 2382; 2390; 2399; 2406; 2411; 2458; 2459; 2462; 2469; 2528; 2529; 2532; 2533; 2534; 2538; 2542; 2543; 2556; 2562; 2563; 2564; 2575; 2652; 2679; 2703; 2708; 2709; 2725; 2727; 2732; 2740; 2743; 2812; 2879; 2887; 2888; 2900; 2941; 2942; 2943; 2944; 2975; 3001; 3018; 3043; 3057; 3061; 3070; 3092; 3173; 3221; 3242; 3265; 3286; 3384; 3387; 3388; 3429; 3500; 3520; 3574; 3596; 3600; 3673; 3690; 3732; 3751; 3767; 3782; 3807; 3809; 3810; 3811; 3819; 3820; 3822; 3857; 3862; 3904; 3920; 3936; 3940; 3958; 3985; 4017; 4019; 4051; 4076; 4093; 4094; 4096; 4130; 4295; 4297; 4345; 4350; 4351; 4399; 4428; 4434; 4442; 4468; 4493; 4497; 4510; 4515; 4523; 4546; 4596; 4603; 4706; 4736; 4744; 4804; 4807; 4860; 4885; 4887; 4888; 4889; 4890; 4891; 4892; 4897; 4898; 4899; 4918; 4955; 4975; 4976; 4978; 4982; 5017; 5031; 5067; 5080; 5109; 5125; 5144; 5147; 5188; 5196; 5198; 5221; 5238; 5249; 5305; 5373; 5380; 5383; 5416; 5450; 5501; 5519; 5529; 5532; 5534; 5555 (see Table 1).

This combination permits correctly classifying 93.0% of the samples.

2.6. Identification of a Predictive Panel of 170 Markers (PANEL 4)

The inventors have demonstrated a combination of 170 markers, linked to a KNN algorithm, based on the sequences SEQ ID Nos: 1; 28; 73; 321; 323; 350; 397; 417; 418; 612; 720; 788; 852; 990; 991; 1152; 1154; 1169; 1212; 1237; 1239; 1242; 1326; 1489; 1490; 1641; 1683; 1694; 1711; 1723; 1731; 1741; 1744; 1747; 1749; 1789; 1800; 1831; 1833; 1834; 1837; 1950; 1951; 1952; 1953; 1984; 1994; 1995; 2023; 2038; 2117; 2126; 2127; 2128; 2129; 2130; 2133; 2144; 2284; 2305; 2365; 2372; 2375; 2378; 2380; 2382; 2399; 2406; 2411; 2458; 2459; 2462; 2528; 2529; 2532; 2533; 2534; 2538; 2542; 2543; 2556; 2563; 2564; 2652; 2679; 2703; 2708; 2709; 2725; 2727; 2732; 2740; 2887; 2888; 2900; 2941; 2942; 2943; 2944; 3043; 3057; 3092; 3286; 3384; 3387; 3596; 3600; 3690; 3782; 3807; 3810; 3811; 3822; 3857; 3862; 3904; 3920; 3940; 3958; 4019; 4076; 4093; 4094; 4096; 4130; 4295; 4297; 4345; 4351; 4428; 4434; 4442; 4468; 4493; 4510; 4515; 4546; 4596; 4603; 4706; 4736; 4744; 4804; 4860; 4885; 4888; 4889; 4890; 4891; 4892; 4897; 4898; 4899; 4918; 4955; 4975; 4976; 4978; 4982; 5067; 5080; 5144; 5198; 5221; 5238; 5380; 5383; 5450; 5532; 5555 (see Table 1).

This combination permits correctly classifying 93.0% of the samples.

2.7. Identification of a Predictive Panel of 200 Markers (PANEL 5)

The inventors have demonstrated a combination of 200 markers, linked to a KNN algorithm, based on the sequences SEQ ID Nos: 1; 6; 8; 28; 73; 90; 321; 323; 343; 350; 352; 397; 417; 418; 513; 538; 542; 600; 612; 720; 738; 788; 852; 990; 991; 1152; 1154; 1169; 1212; 1237; 1239; 1242; 1326; 1489; 1490; 1511; 1641; 1683; 1694; 1711; 1723; 1731; 1741; 1744; 1747; 1749; 1789; 1800; 1831; 1833; 1834; 1837; 1859; 1950; 1951; 1952; 1953; 1984; 1994; 1995; 2023; 2038; 2117; 2126; 2127; 2128; 2129; 2130; 2132; 2133; 2143; 2144; 2209; 2284; 2305; 2365; 2372; 2374; 2375; 2378; 2380; 2382; 2390; 2399; 2406; 2411; 2458; 2459; 2462; 2469; 2528; 2529; 2532; 2533; 2534; 2538; 2542; 2543; 2556; 2563; 2564; 2652; 2679; 2703; 2708; 2709; 2725; 2727; 2732; 2740; 2887; 2888; 2900; 2941; 2942; 2943; 2944; 3001; 3043; 3057; 3092; 3286; 3384; 3387; 3388; 3429; 3574; 3596; 3600; 3673; 3690; 3767; 3782; 3807; 3810; 3811; 3822; 3857; 3862; 3904; 3920; 3936; 3940; 3958; 3985; 4019; 4076; 4093; 4094; 4096; 4130; 4295; 4297; 4345; 4350; 4351; 4428; 4434; 4442; 4468; 4493; 4497; 4510; 4515; 4546; 4596; 4603; 4706; 4736; 4744; 4804; 4860; 4885; 4888; 4889; 4890; 4891; 4892; 4897; 4898; 4899; 4918; 4955; 4975; 4976; 4978; 4982; 5017; 5067; 5080; 5144; 5198; 5221; 5238; 5380; 5383; 5450; 5529; 5532; 5555 (see Table 1).

This combination permits correctly classifying 92.8% of the samples.

2.8. Identification of a Predictive Panel of 140 Markers (PANEL 6)

The inventors have demonstrated a combination of 140 markers, linked to a KNN algorithm, based on the sequences SEQ ID Nos: 1; 28; 73; 321; 323; 350; 417; 418; 720; 852; 990; 1152; 1154; 1169; 1212; 1237; 1239; 1242; 1326; 1489; 1490; 1683; 1694; 1711; 1723; 1731; 1741; 1744; 1749; 1800; 1833; 1834; 1837; 1951; 1952; 1953; 1984; 1995;

2023; 2038; 2117; 2126; 2127; 2128; 2129; 2130; 2133; 2144; 2284; 2305; 2365; 2372; 2378; 2380; 2382; 2399; 2411; 2459; 2462; 2528; 2529; 2532; 2533; 2542; 2543; 2556; 2563; 2564; 2652; 2679; 2703; 2709; 2725; 2727; 2732; 2740; 2887; 2888; 2900; 2941; 2943; 2944; 3043; 3057; 3286; 3387; 3596; 3600; 3690; 3782; 3810; 3811; 3822; 3857; 3904; 3920; 3940; 3958; 4076; 4093; 4094; 4096; 4130; 4295; 4345; 4351; 4428; 4434; 4442; 4468; 4493; 4510; 4546; 4603; 4744; 4804; 4860; 4885; 4888; 4889; 4890; 4891; 4892; 4897; 4898; 4899; 4918; 4955; 4975; 4976; 4978; 4982; 5144; 5198; 5221; 5238; 5380; 5383; 5450; 5532 (see Table 1).

This combination permits correctly classifying 92.8% of the samples.

2.9. Identification of a Predictive Panel of 110 Markers (PANEL 7)

The inventors have demonstrated a combination of 110 markers, linked to a KNN algorithm, based on the sequences SEQ ID Nos: 1; 28; 73; 321; 323; 418; 852; 1152; 1154; 1237; 1242; 1326; 1683; 1694; 1731; 1741; 1744; 1749; 1833; 1834; 1951; 1984; 1995; 2023; 2038; 2126; 2127; 2128; 2129; 2130; 2133; 2144; 2284; 2305; 2365; 2372; 2378; 2380; 2382; 2411; 2459; 2462; 2528; 2529; 2532; 2533; 2542; 2543; 2556; 2563; 2679; 2703; 2725; 2727; 2732; 2740; 2887; 2888; 2900; 2941; 2943; 2944; 3043; 3057; 3286; 3387; 3596; 3600; 3782; 3822; 3857; 3904; 3920; 3940; 3958; 4093; 4094; 4096; 4130; 4295; 4345; 4351; 4428; 4442; 4468; 4493; 4510; 4603; 4744; 4804; 4860; 4885; 4888; 4889; 4890; 4891; 4897; 4898; 4899; 4918; 4975; 4976; 4978; 4982; 5144; 5198; 5221; 5238; 5380; 5383 (see Table 1).

This combination permits correctly classifying 92.8% of the samples.

2.10. Identification of a Predictive Panel of 190 Markers (PANEL 8)

The inventors have demonstrated a combination of 190 markers, linked to a KNN algorithm, based on the sequences SEQ ID Nos: 1; 6; 28; 73; 321; 323; 343; 350; 352; 397; 417; 418; 513; 538; 542; 612; 720; 788; 852; 990; 991; 1152; 1154; 1169; 1212; 1237; 1239; 1242; 1326; 1489; 1490; 1641; 1683; 1694; 1711; 1723; 1731; 1741; 1744; 1747; 1749; 1789; 1800; 1831; 1833; 1834; 1837; 1859; 1950; 1951; 1952; 1953; 1984; 1994; 1995; 2023; 2038; 2117; 2126; 2127; 2128; 2129; 2130; 2132; 2133; 2143; 2144; 2209; 2284; 2305; 2365; 2372; 2375; 2378; 2380; 2382; 2390; 2399; 2406; 2411; 2458; 2459; 2462; 2469; 2528; 2529; 2532; 2533; 2534; 2538; 2542; 2543; 2556; 2563; 2564; 2652; 2679; 2703; 2708; 2709; 2725; 2727; 2732; 2740; 2887; 2888; 2900; 2941; 2942; 2943; 2944; 3043; 3057; 3092; 3286; 3384; 3387; 3574; 3596; 3600; 3673; 3690; 3767; 3782; 3807; 3810; 3811; 3822; 3857; 3862; 3904; 3920; 3936; 3940; 3958; 4019; 4076; 4093; 4094; 4096; 4130; 4295; 4297; 4345; 4350; 4351; 4428; 4434; 4442; 4468; 4493; 4497; 4510; 4515; 4546; 4596; 4603; 4706; 4736; 4744; 4804; 4860; 4885; 4888; 4889; 4890; 4891; 4892; 4897; 4898; 4899; 4918; 4955; 4975; 4976; 4978; 4982; 5017; 5067; 5080; 5144; 5198; 5221; 5238; 5380; 5383; 5450; 5529; 5532; 5555 (see Table 1).

This combination permits correctly classifying 92.8% of the samples.

2.11. Identification of a Predictive Panel of 240 Markers (PANEL 9)

The inventors have demonstrated a combination of 240 markers, linked to a KNN algorithm, based on the sequences SEQ ID Nos: 1; 6; 8; 28; 73; 80; 90; 224; 314; 321; 323; 331; 343; 345; 349; 350; 352; 397; 417; 418; 429; 513; 538; 542; 600; 612; 720; 723; 738; 742; 788; 852; 978; 990; 991; 1152; 1154; 1169; 1212; 1237; 1239; 1242; 1295; 1326; 1489; 1490; 1511; 1641; 1683; 1694; 1711; 1723; 1731; 1741; 1744; 1747; 1749; 1789; 1800; 1806; 1831; 1833; 1834; 1837; 1859; 1861; 1950; 1951; 1952; 1953; 1984; 1994; 1995; 2023; 2038; 2090; 2091; 2117; 2126; 2127; 2128; 2129; 2130; 2132; 2133; 2143; 2144; 2209; 2284; 2305; 2365; 2372; 2374; 2375; 2378; 2380; 2382; 2390; 2399; 2406; 2411; 2458; 2459; 2462; 2469; 2528; 2529; 2532; 2533; 2534; 2538; 2542; 2543; 2556; 2563; 2564; 2652; 2679; 2703; 2708; 2709; 2725; 2727; 2732; 2740; 2743; 2812; 2879; 2887; 2888; 2900; 2941; 2942; 2943; 2944; 2975; 3001; 3043; 3057; 3061; 3070; 3092; 3173; 3242; 3286; 3384; 3387; 3388; 3429; 3520; 3574; 3596; 3600; 3673; 3690; 3751; 3767; 3782; 3807; 3809; 3810; 3811; 3820; 3822; 3857; 3862; 3904; 3920; 3936; 3940; 3958; 3985; 4019; 4051; 4076; 4093; 4094; 4096; 4130; 4295; 4297; 4345; 4350; 4351; 4399; 4428; 4434; 4442; 4468; 4493; 4497; 4510; 4515; 4523; 4546; 4596; 4603; 4706; 4736; 4744; 4804; 4860; 4885; 4887; 4888; 4889; 4890; 4891; 4892; 4897; 4898; 4899; 4918; 4955; 4975; 4976; 4978; 4982; 5017; 5031; 5067; 5080; 5109; 5125; 5144; 5147; 5196; 5198; 5221; 5238; 5373; 5380; 5383; 5416; 5450; 5501; 5529; 5532; 5534; 5555 (see Table 1).

This combination permits correctly classifying 92.8% of the samples.

2.12. Identification of a Predictive Panel of 200 Markers (PANEL 10)

The inventors have demonstrated a combination of 200 markers, linked to a KNN algorithm, based on the sequences SEQ ID Nos: 1; 6; 8; 28; 73; 90; 321; 323; 343; 350; 352; 397; 417; 418; 513; 538; 542; 600; 612; 720; 738; 788; 852; 990; 991; 1152; 1154; 1169; 1212; 1237; 1239; 1242; 1326; 1489; 1490; 1511; 1641; 1683; 1694; 1711; 1723; 1731; 1741; 1744; 1747; 1749; 1789; 1800; 1831; 1833; 1834; 1837; 1859; 1950; 1951; 1952; 1953; 1984; 1994; 1995; 2023; 2038; 2117; 2126; 2127; 2128; 2129; 2130; 2132; 2133; 2143; 2144; 2209; 2284; 2305; 2365; 2372; 2374; 2375; 2378; 2380; 2382; 2390; 2399; 2406; 2411; 2458; 2459; 2462; 2469; 2528; 2529; 2532; 2533; 2534; 2538; 2542; 2543; 2556; 2563; 2564; 2652; 2679; 2703; 2708; 2709; 2725; 2727; 2732; 2740; 2887; 2888; 2900; 2941; 2942; 2943; 2944; 3001; 3043; 3057; 3092; 3286; 3384; 3387; 3388; 3429; 3574; 3596; 3600; 3673; 3690; 3767; 3782; 3807; 3810; 3811; 3822; 3857; 3862; 3904; 3920; 3936; 3940; 3958; 3985; 4019; 4076; 4093; 4094; 4096; 4130; 4295; 4297; 4345; 4350; 4351; 4428; 4434; 4442; 4468; 4493; 4497; 4510; 4515; 4546; 4596; 4603; 4706; 4736; 4744; 4804; 4860; 4885; 4888; 4889; 4890; 4891; 4892; 4897; 4898; 4899; 4918; 4955; 4975; 4976; 4978; 4982; 5017; 5067; 5080; 5144; 5198; 5221; 5238; 5380; 5383; 5450; 5529; 5532; 5555 (see Table 1).

This combination permits correctly classifying 92.5% of the samples.

2.13. Identification of a Predictive Panel of 190 Markers (PANEL 11)

The inventors have demonstrated a combination of 190 markers, linked to a KNN algorithm, based on the sequences SEQ ID Nos: 1; 6; 28; 73; 321; 323; 343; 350; 352; 397; 417; 418; 513; 538; 542; 612; 720; 788; 852; 990; 991; 1152; 1154; 1169; 1212; 1237; 1239; 1242; 1326; 1489; 1490; 1641; 1683; 1694; 1711; 1723; 1731; 1741; 1744; 1747; 1749; 1789; 1800; 1831; 1833; 1834; 1837; 1859; 1950; 1951; 1952; 1953; 1984; 1994; 1995; 2023; 2038; 2117; 2126; 2127; 2128; 2129; 2130; 2132; 2133; 2143; 2144; 2209; 2284; 2305; 2365; 2372; 2375; 2378; 2380; 2382; 2390; 2399; 2406; 2411; 2458; 2459; 2462; 2469; 2528; 2529; 2532; 2533; 2534; 2538; 2542; 2543; 2556; 2563; 2564;

2652; 2679; 2703; 2708; 2709; 2725; 2727; 2732; 2740; 2887; 2888; 2900; 2941; 2942; 2943; 2944; 3043; 3057; 3092; 3286; 3384; 3387; 3574; 3596; 3600; 3673; 3690; 3767; 3782; 3807; 3810; 3811; 3822; 3857; 3862; 3904; 3920; 3936; 3940; 3958; 4019; 4076; 4093; 4094; 4096; 4130; 4295; 4297; 4345; 4350; 4351; 4428; 4434; 4442; 4468; 4493; 4497; 4510; 4515; 4546; 4596; 4603; 4706; 4736; 4744; 4804; 4860; 4885; 4888; 4889; 4890; 4891; 4892; 4897; 4898; 4899; 4918; 4955; 4975; 4976; 4978; 4982; 5017; 5067; 5080; 5144; 5198; 5221; 5238; 5380; 5383; 5450; 5529; 5532; 5555 (see Table 1).

This combination permits correctly classifying 92.5% of the samples.

2.14. Identification of a Predictive Panel of 210 Markers (PANEL 12)

The inventors have demonstrated a combination of 210 markers, linked to a KNN algorithm, based on the sequences SEQ ID Nos: 1; 6; 8; 28; 73; 90; 321; 323; 343; 345; 350; 352; 397; 417; 418; 513; 538; 542; 600; 612; 720; 738; 788; 852; 990; 991; 1152; 1154; 1169; 1212; 1237; 1239; 1242; 1326; 1489; 1490; 1511; 1641; 1683; 1694; 1711; 1723; 1731; 1741; 1744; 1747; 1749; 1789; 1800; 1806; 1831; 1833; 1834; 1837; 1859; 1950; 1951; 1952; 1953; 1984; 1994; 1995; 2023; 2038; 2117; 2126; 2127; 2128; 2129; 2130; 2132; 2133; 2143; 2144; 2209; 2284; 2305; 2365; 2372; 2374; 2375; 2378; 2380; 2382; 2390; 2399; 2406; 2411; 2458; 2459; 2462; 2469; 2528; 2529; 2532; 2533; 2534; 2538; 2542; 2543; 2556; 2563; 2564; 2652; 2679; 2703; 2708; 2709; 2725; 2727; 2732; 2740; 2743; 2887; 2888; 2900; 2941; 2942; 2943; 2944; 3001; 3043; 3057; 3092; 3173; 3286; 3384; 3387; 3388; 3429; 3574; 3596; 3600; 3673; 3690; 3767; 3782; 3807; 3810; 3811; 3820; 3822; 3857; 3862; 3904; 3920; 3936; 3940; 3958; 3985; 4019; 4076; 4093; 4094; 4096; 4130; 4295; 4297; 4345; 4350; 4351; 4399; 4428; 4434; 4442; 4468; 4493; 4497; 4510; 4515; 4546; 4596; 4603; 4706; 4736; 4744; 4804; 4860; 4885; 4887; 4888; 4889; 4890; 4891; 4892; 4897; 4898; 4899; 4918; 4955; 4975; 4976; 4978; 4982; 5017; 5067; 5080; 5144; 5147; 5198; 5221; 5238; 5373; 5380; 5383; 5416; 5450; 5529; 5532; 5555 (see Table 1).

This combination permits correctly classifying 92.5% of the samples.

2.15. Identification of a Predictive Panel of 260 Markers (PANEL 13)

The inventors have demonstrated a combination of 260 markers, linked to a KNN algorithm, based on the sequences SEQ ID Nos: 1; 6; 8; 28; 73; 80; 84; 90; 224; 314; 321; 323; 331; 343; 345; 349; 350; 352; 397; 417; 418; 429; 513; 538; 542; 600; 612; 629; 720; 723; 738; 742; 788; 852; 978; 990; 991; 1152; 1154; 1169; 1212; 1237; 1239; 1242; 1295; 1326; 1489; 1490; 1511; 1641; 1683; 1694; 1711; 1714; 1723; 1731; 1732; 1741; 1744; 1747; 1749; 1789; 1800; 1806; 1831; 1833; 1834; 1836; 1837; 1859; 1861; 1950; 1951; 1952; 1953; 1984; 1985; 1994; 1995; 2023; 2038; 2090; 2091; 2117; 2126; 2127; 2128; 2129; 2130; 2132; 2133; 2143; 2144; 2209; 2284; 2305; 2365; 2372; 2374; 2375; 2378; 2380; 2382; 2390; 2399; 2406; 2411; 2458; 2459; 2462; 2469; 2528; 2529; 2532; 2533; 2534; 2538; 2542; 2543; 2556; 2562; 2563; 2564; 2575; 2652; 2679; 2703; 2708; 2709; 2725; 2727; 2732; 2740; 2743; 2812; 2879; 2887; 2888; 2900; 2941; 2942; 2943; 2944; 2975; 3001; 3018; 3043; 3057; 3061; 3070; 3092; 3173; 3221; 3242; 3265; 3286; 3384; 3387; 3388; 3429; 3500; 3520; 3574; 3596; 3600; 3673; 3690; 3732; 3751; 3767; 3782; 3807; 3809; 3810; 3811; 3819; 3820; 3822; 3857; 3862; 3904; 3920; 3936; 3940; 3958; 3985; 4017; 4019; 4051; 4076; 4093; 4094; 4096; 4130; 4295; 4297; 4345; 4350; 4351; 4399; 4428; 4434; 4442; 4468; 4493; 4497; 4510; 4515; 4523; 4546; 4596; 4603; 4706; 4736; 4744; 4804; 4807; 4860; 4885; 4887; 4888; 4889; 4890; 4891; 4892; 4897; 4898; 4899; 4918; 4955; 4975; 4976; 4978; 4982; 5017; 5031; 5067; 5080; 5109; 5125; 5144; 5147; 5188; 5196; 5198; 5221; 5238; 5249; 5305; 5373; 5380; 5383; 5416; 5450; 5501; 5519; 5529; 5532; 5534; 5555 (see Table 1).

This combination permits correctly classifying 92.5% of the samples.

2.16. Identification of a Predictive Panel of 180 Markers (PANEL 14)

The inventors have demonstrated a combination of 180 markers, linked to a KNN algorithm, based on the sequences SEQ ID Nos: 1; 28; 73; 321; 323; 350; 352; 397; 417; 418; 513; 538; 612; 720; 788; 852; 990; 991; 1152; 1154; 1169; 1212; 1237; 1239; 1242; 1326; 1489; 1490; 1641; 1683; 1694; 1711; 1723; 1731; 1741; 1744; 1747; 1749; 1789; 1800; 1831; 1833; 1834; 1837; 1859; 1950; 1951; 1952; 1953; 1984; 1994; 1995; 2023; 2038; 2117; 2126; 2127; 2128; 2129; 2130; 2133; 2143; 2144; 2284; 2305; 2365; 2372; 2375; 2378; 2380; 2382; 2390; 2399; 2406; 2411; 2458; 2459; 2462; 2528; 2529; 2532; 2533; 2534; 2538; 2542; 2543; 2556; 2563; 2564; 2652; 2679; 2703; 2708; 2709; 2725; 2727; 2732; 2740; 2887; 2888; 2900; 2941; 2942; 2943; 2944; 3043; 3057; 3092; 3286; 3384; 3387; 3574; 3596; 3600; 3673; 3690; 3782; 3807; 3810; 3811; 3822; 3857; 3862; 3904; 3920; 3936; 3940; 3958; 4019; 4076; 4093; 4094; 4096; 4130; 4295; 4297; 4345; 4351; 4428; 4434; 4442; 4468; 4493; 4497; 4510; 4515; 4546; 4596; 4603; 4706; 4736; 4744; 4804; 4860; 4885; 4888; 4889; 4890; 4891; 4892; 4897; 4898; 4899; 4918; 4955; 4975; 4976; 4978; 4982; 5067; 5080; 5144; 5198; 5221; 5238; 5380; 5383; 5450; 5532; 5555 (see Table 1).

This combination permits correctly classifying 92.5% of the samples.

2.17. Identification of a Predictive Panel of 190 Markers (PANEL 15)

The inventors have demonstrated a combination of 190 markers, linked to a KNN algorithm, based on the sequences SEQ ID Nos: 1; 6; 28; 73; 321; 323; 343; 350; 352; 397; 417; 418; 513; 538; 542; 612; 720; 788; 852; 990; 991; 1152; 1154; 1169; 1212; 1237; 1239; 1242; 1326; 1489; 1490; 1641; 1683; 1694; 1711; 1723; 1731; 1741; 1744; 1747; 1749; 1789; 1800; 1831; 1833; 1834; 1837; 1859; 1950; 1951; 1952; 1953; 1984; 1994; 1995; 2023; 2038; 2117; 2126; 2127; 2128; 2129; 2130; 2132; 2133; 2143; 2144; 2209; 2284; 2305; 2365; 2372; 2375; 2378; 2380; 2382; 2390; 2399; 2406; 2411; 2458; 2459; 2462; 2469; 2528; 2529; 2532; 2533; 2534; 2538; 2542; 2543; 2556; 2563; 2564; 2652; 2679; 2703; 2708; 2709; 2725; 2727; 2732; 2740; 2887; 2888; 2900; 2941; 2942; 2943; 2944; 3043; 3057; 3092; 3286; 3384; 3387; 3574; 3596; 3600; 3673; 3690; 3767; 3782; 3807; 3810; 3811; 3822; 3857; 3862; 3904; 3920; 3936; 3940; 3958; 4019; 4076; 4093; 4094; 4096; 4130; 4295; 4297; 4345; 4350; 4351; 4428; 4434; 4442; 4468; 4493; 4497; 4510; 4515; 4546; 4596; 4603; 4706; 4736; 4744; 4804; 4860; 4885; 4888; 4889; 4890; 4891; 4892; 4897; 4898; 4899; 4918; 4955; 4975; 4976; 4978; 4982; 5017; 5067; 5080; 5144; 5198; 5221; 5238; 5380; 5383; 5450; 5529; 5532; 5555 (see Table 1).

This combination permits correctly classifying 92.5% of the samples.

2.18. Identification of a Predictive Panel of 250 Markers (PANEL 16)

The inventors have demonstrated a combination of 250 markers, linked to a KNN algorithm, based on the sequences SEQ ID Nos: 1; 6; 8; 28; 73; 80; 90; 224; 314; 321; 323; 331;

343; 345; 349; 350; 352; 397; 417; 418; 429; 513; 538; 542; 600; 612; 629; 720; 723; 738; 742; 788; 852; 978; 990; 991; 1152; 1154; 1169; 1212; 1237; 1239; 1242; 1295; 1326; 1489; 1490; 1511; 1641; 1683; 1694; 1711; 1723; 1731; 1732; 1741; 1744; 1747; 1749; 1789; 1800; 1806; 1831; 1833; 1834; 1837; 1859; 1861; 1950; 1951; 1952; 1953; 1984; 1985; 1994; 1995; 2023; 2038; 2090; 2091; 2117; 2126; 2127; 2128; 2129; 2130; 2132; 2133; 2143; 2144; 2209; 2284; 2305; 2365; 2372; 2374; 2375; 2378; 2380; 2382; 2390; 2399; 2406; 2411; 2458; 2459; 2462; 2469; 2528; 2529; 2532; 2533; 2534; 2538; 2542; 2543; 2556; 2563; 2564; 2575; 2652; 2679; 2703; 2708; 2709; 2725; 2727; 2732; 2740; 2743; 2812; 2879; 2887; 2888; 2900; 2941; 2942; 2943; 2944; 2975; 3001; 3018; 3043; 3057; 3061; 3070; 3092; 3173; 3221; 3242; 3286; 3384; 3387; 3388; 3429; 3520; 3574; 3596; 3600; 3673; 3690; 3751; 3767; 3782; 3807; 3809; 3810; 3811; 3819; 3820; 3822; 3857; 3862; 3904; 3920; 3936; 3940; 3958; 3985; 4017; 4019; 4051; 4076; 4093; 4094; 4096; 4130; 4295; 4297; 4345; 4350; 4351; 4399; 4428; 4434; 4442; 4468; 4493; 4497; 4510; 4515; 4523; 4546; 4596; 4603; 4706; 4736; 4744; 4804; 4807; 4860; 4885; 4887; 4888; 4889; 4890; 4891; 4892; 4897; 4898; 4899; 4918; 4955; 4975; 4976; 4978; 4982; 5017; 5031; 5067; 5080; 5109; 5125; 5144; 5147; 5188; 5196; 5198; 5221; 5238; 5373; 5380; 5383; 5416; 5450; 5501; 5529; 5532; 5534; 5555 (see Table 1).

This combination permits correctly classifying 92.5% of the samples.

2.19. Identification of a Predictive Panel of 250 Markers (PANEL 17)

The inventors have demonstrated a combination of 250 markers, linked to a KNN algorithm, based on the sequences SEQ ID Nos: 1; 6; 8; 28; 73; 80; 90; 224; 314; 321; 323; 331; 343; 345; 349; 350; 352; 397; 417; 418; 429; 513; 538; 542; 600; 612; 629; 720; 723; 738; 742; 788; 852; 978; 990; 991; 1152; 1154; 1169; 1212; 1237; 1239; 1242; 1295; 1326; 1489; 1490; 1511; 1641; 1683; 1694; 1711; 1723; 1731; 1732; 1741; 1744; 1747; 1749; 1789; 1800; 1806; 1831; 1833; 1834; 1837; 1859; 1861; 1950; 1951; 1952; 1953; 1984; 1985; 1994; 1995; 2023; 2038; 2090; 2091; 2117; 2126; 2127; 2128; 2129; 2130; 2132; 2133; 2143; 2144; 2209; 2284; 2305; 2365; 2372; 2374; 2375; 2378; 2380; 2382; 2390; 2399; 2406; 2411; 2458; 2459; 2462; 2469; 2528; 2529; 2532; 2533; 2534; 2538; 2542; 2543; 2556; 2563; 2564; 2575; 2652; 2679; 2703; 2708; 2709; 2725; 2727; 2732; 2740; 2743; 2812; 2879; 2887; 2888; 2900; 2941; 2942; 2943; 2944; 2975; 3001; 3018; 3043; 3057; 3061; 3070; 3092; 3173; 3221; 3242; 3286; 3384; 3387; 3388; 3429; 3520; 3574; 3596; 3600; 3673; 3690; 3751; 3767; 3782; 3807; 3809; 3810; 3811; 3819; 3820; 3822; 3857; 3862; 3904; 3920; 3936; 3940; 3958; 3985; 4017; 4019; 4051; 4076; 4093; 4094; 4096; 4130; 4295; 4297; 4345; 4350; 4351; 4399; 4428; 4434; 4442; 4468; 4493; 4497; 4510; 4515; 4523; 4546; 4596; 4603; 4706; 4736; 4744; 4804; 4807; 4860; 4885; 4887; 4888; 4889; 4890; 4891; 4892; 4897; 4898; 4899; 4918; 4955; 4975; 4976; 4978; 4982; 5017; 5031; 5067; 5080; 5109; 5125; 5144; 5147; 5188; 5196; 5198; 5221; 5238; 5373; 5380; 5383; 5416; 5450; 5501; 5529; 5532; 5534; 5555 (see Table 1).

This combination permits correctly classifying 92.5% of the samples.

2.20. Identification of a Predictive Panel of 110 Markers (PANEL 18)

The inventors have demonstrated a combination of 110 markers, linked to a KNN algorithm, based on the sequences SEQ ID Nos: 1; 28; 73; 321; 323; 418; 852; 1152; 1154; 1237; 1242; 1326; 1683; 1694; 1731; 1741; 1744; 1749; 1833; 1834; 1951; 1984; 1995; 2023; 2038; 2126; 2127; 2128; 2129; 2130; 2133; 2144; 2284; 2305; 2365; 2372; 2378; 2380; 2382; 2411; 2459; 2462; 2528; 2529; 2532; 2533; 2542; 2543; 2556; 2563; 2679; 2703; 2725; 2727; 2732; 2740; 2887; 2888; 2900; 2941; 2943; 2944; 3043; 3057; 3286; 3387; 3596; 3600; 3782; 3822; 3857; 3904; 3920; 3940; 3958; 4093; 4094; 4096; 4130; 4295; 4345; 4351; 4428; 4442; 4468; 4493; 4510; 4603; 4744; 4804; 4860; 4885; 4888; 4889; 4890; 4891; 4897; 4898; 4899; 4918; 4975; 4976; 4978; 4982; 5144; 5198; 5221; 5238; 5380; 5383 (see Table 1).

This combination permits correctly classifying 92.5% of the samples.

2.21. Identification of a Predictive Panel of 220 Markers (PANEL 19)

The inventors have demonstrated a combination of 220 markers, linked to a KNN algorithm, based on the sequences SEQ ID Nos: 1; 6; 8; 28; 73; 80; 90; 321; 323; 343; 345; 350; 352; 397; 417; 418; 513; 538; 542; 600; 612; 720; 738; 788; 852; 978; 990; 991; 1152; 1154; 1169; 1212; 1237; 1239; 1242; 1295; 1326; 1489; 1490; 1511; 1641; 1683; 1694; 1711; 1723; 1731; 1741; 1744; 1747; 1749; 1789; 1800; 1806; 1831; 1833; 1834; 1837; 1859; 1950; 1951; 1952; 1953; 1984; 1994; 1995; 2023; 2038; 2090; 2091; 2117; 2126; 2127; 2128; 2129; 2130; 2132; 2133; 2143; 2144; 2209; 2284; 2305; 2365; 2372; 2374; 2375; 2378; 2380; 2382; 2390; 2399; 2406; 2411; 2458; 2459; 2462; 2469; 2528; 2529; 2532; 2533; 2534; 2538; 2542; 2543; 2556; 2563; 2564; 2652; 2679; 2703; 2708; 2709; 2725; 2727; 2732; 2740; 2743; 2812; 2887; 2888; 2900; 2941; 2942; 2943; 2944; 3001; 3043; 3057; 3061; 3092; 3173; 3242; 3286; 3384; 3387; 3388; 3429; 3574; 3596; 3600; 3673; 3690; 3767; 3782; 3807; 3810; 3811; 3820; 3822; 3857; 3862; 3904; 3920; 3936; 3940; 3958; 3985; 4019; 4051; 4076; 4093; 4094; 4096; 4130; 4295; 4297; 4345; 4350; 4351; 4399; 4428; 4434; 4442; 4468; 4493; 4497; 4510; 4515; 4546; 4596; 4603; 4706; 4736; 4744; 4804; 4860; 4885; 4887; 4888; 4889; 4890; 4891; 4892; 4897; 4898; 4899; 4918; 4955; 4975; 4976; 4978; 4982; 5017; 5067; 5080; 5144; 5147; 5198; 5221; 5238; 5373; 5380; 5383; 5416; 5450; 5529; 5532; 5534; 5555 (see Table 1).

This combination permits correctly classifying 92.5% of the samples.

2.22. Identification of a Predictive Panel of 270 Markers (PANEL 20)

The inventors have demonstrated a combination of 270 markers, linked to a KNN algorithm, based on the sequences SEQ ID Nos: 1; 6; 8; 28; 73; 80; 84; 90; 224; 314; 321; 323; 331; 343; 345; 349; 350; 352; 397; 417; 418; 429; 513; 538; 542; 600; 612; 629; 720; 723; 724; 738; 742; 788; 852; 978; 990; 991; 1107; 1152; 1154; 1169; 1212; 1237; 1239; 1242; 1260; 1295; 1326; 1489; 1490; 1511; 1641; 1683; 1694; 1711; 1714; 1723; 1731; 1732; 1741; 1744; 1747; 1749; 1789; 1800; 1806; 1831; 1833; 1834; 1836; 1837; 1859; 1861; 1950; 1951; 1952; 1953; 1984; 1985; 1994; 1995; 2023; 2038; 2090; 2091; 2117; 2126; 2127; 2128; 2129; 2130; 2132; 2133; 2143; 2144; 2209; 2284; 2305; 2365; 2372; 2374; 2375; 2378; 2380; 2382; 2390; 2399; 2406; 2411; 2458; 2459; 2462; 2469; 2528; 2529; 2532; 2533; 2534; 2538; 2542; 2543; 2556; 2562; 2563; 2564; 2575; 2652; 2679; 2703; 2708; 2709; 2725; 2727; 2732; 2740; 2743; 2812; 2879; 2887; 2888; 2900; 2941; 2942; 2943; 2944; 2975; 3001; 3018; 3043; 3056; 3057; 3061; 3070; 3092; 3173; 3221; 3242; 3265; 3286; 3384; 3387; 3388; 3429; 3500; 3520; 3574; 3576; 3596; 3600; 3673; 3690; 3732; 3751; 3767; 3782; 3807; 3809; 3810; 3811; 3819; 3820; 3822; 3857; 3862; 3904; 3920; 3936; 3940; 3950;

3958; 3985; 4017; 4019; 4051; 4076; 4093; 4094; 4096; 4130; 4295; 4297; 4345; 4350; 4351; 4399; 4428; 4434; 4442; 4468; 4493; 4497; 4510; 4515; 4523; 4546; 4592; 4596; 4603; 4706; 4736; 4744; 4804; 4807; 4860; 4885; 4887; 4888; 4889; 4890; 4891; 4892; 4897; 4898; 4899; 4918; 4955; 4975; 4976; 4978; 4979; 4982; 5017; 5031; 5067; 5080; 5109; 5125; 5144; 5147; 5188; 5196; 5198; 5221; 5238; 5249; 5305; 5333; 5373; 5380; 5383; 5416; 5450; 5501; 5519; 5521; 5529; 5532; 5534; 5555 (see Table 1).

This combination permits correctly classifying 92.5% of the samples.

2.23. Identification of a Predictive Panel of 290 Markers (PANEL 21)

The inventors have demonstrated a combination of 290 markers, linked to a KNN algorithm, based on the sequences SEQ ID Nos: 1; 6; 8; 28; 55; 73; 80; 84; 90; 224; 314; 321; 323; 331; 343; 345; 349; 350; 352; 397; 417; 418; 429; 513; 538; 542; 600; 612; 629; 720; 723; 724; 738; 742; 788; 852; 978; 990; 991; 1107; 1152; 1154; 1169; 1212; 1237; 1239; 1242; 1260; 1295; 1326; 1489; 1490; 1511; 1641; 1683; 1694; 1699; 1711; 1714; 1723; 1731; 1732; 1741; 1744; 1747; 1749; 1789; 1800; 1806; 1831; 1833; 1834; 1836; 1837; 1859; 1861; 1950; 1951; 1952; 1953; 1984; 1985; 1994; 1995; 2022; 2023; 2038; 2090; 2091; 2117; 2126; 2127; 2128; 2129; 2130; 2132; 2133; 2143; 2144; 2192; 2209; 2284; 2305; 2365; 2372; 2374; 2375; 2378; 2380; 2382; 2390; 2399; 2406; 2411; 2458; 2459; 2462; 2469; 2528; 2529; 2532; 2533; 2534; 2538; 2542; 2543; 2556; 2562; 2563; 2564; 2575; 2590; 2652; 2679; 2703; 2708; 2709; 2725; 2727; 2732; 2740; 2743; 2812; 2879; 2887; 2888; 2900; 2941; 2942; 2943; 2944; 2975; 3001; 3018; 3043; 3056; 3057; 3061; 3070; 3092; 3172; 3173; 3221; 3242; 3265; 3286; 3384; 3387; 3388; 3429; 3487; 3500; 3520; 3574; 3576; 3596; 3600; 3673; 3688; 3690; 3732; 3751; 3767; 3782; 3807; 3809; 3810; 3811; 3819; 3820; 3822; 3857; 3862; 3904; 3920; 3936; 3940; 3950; 3958; 3985; 3996; 4017; 4019; 4051; 4076; 4093; 4094; 4096; 4130; 4295; 4297; 4343; 4345; 4350; 4351; 4399; 4428; 4434; 4442; 4468; 4493; 4497; 4498; 4510; 4515; 4523; 4546; 4592; 4596; 4603; 4607; 4676; 4706; 4736; 4744; 4804; 4807; 4860; 4885; 4886; 4887; 4888; 4889; 4890; 4891; 4892; 4895; 4897; 4898; 4899; 4918; 4955; 4975; 4976; 4978; 4979; 4982; 4986; 5000; 5017; 5031; 5067; 5080; 5109; 5125; 5144; 5147; 5188; 5196; 5198; 5221; 5237; 5238; 5239; 5247; 5249; 5305; 5333; 5373; 5380; 5383; 5416; 5450; 5501; 5519; 5521; 5529; 5532; 5534; 5555 (see Table 1).

This combination permits correctly classifying 92.5% of the samples.

2.24. Identification of a Predictive Panel of 270 Markers (PANEL 22)

The inventors have demonstrated a combination of 270 markers, linked to an SVM algorithm, based on the sequences SEQ ID Nos: 26; 51; 52; 58; 63; 75; 98; 101; 103; 105; 114; 117; 120; 163; 166; 171; 172; 277; 278; 300; 325; 338; 354; 397; 398; 401; 403; 407; 419; 421; 424; 482; 511; 512; 518; 527; 531; 539; 569; 570; 571; 591; 596; 597; 598; 614; 619; 629; 658; 662; 668; 689; 690; 691; 694; 719; 721; 722; 789; 842; 872; 949; 958; 1032; 1033; 1159; 1162; 1166; 1169; 1174; 1214; 1218; 1220; 1229; 1237; 1238; 1240; 1242; 1253; 1257; 1258; 1259; 1270; 1307; 1308; 1346; 1348; 1398; 1432; 1440; 1494; 1495; 1522; 1523; 1551; 1561; 1588; 1624; 1632; 1654; 1668; 1674; 1701; 1724; 1744; 1767; 1786; 1809; 1811; 1841; 1853; 1859; 1951; 1986; 2001; 2003; 2007; 2009; 2010; 2011; 2106; 2107; 2110; 2111; 2112; 2114; 2115; 2144; 2148; 2158; 2185; 2249; 2250; 2251; 2252; 2253; 2260; 2263; 2269; 2281; 2307; 2310; 2320; 2333; 2349; 2350; 2400; 2421; 2442; 2462; 2519; 2594; 2599; 2604; 2619; 2620; 2621; 2622; 2813; 2835; 2838; 2869; 2873; 2887; 2888; 2889; 2896; 2900; 2979; 3005; 3053; 3088; 3106; 3157; 3160; 3185; 3186; 3190; 3193; 3200; 3213; 3218; 3266; 3278; 3296; 3304; 3340; 3376; 3430; 3506; 3508; 3525; 3527; 3531; 3565; 3566; 3567; 3575; 3625; 3626; 3672; 3685; 3782; 3814; 3816; 3824; 3828; 3842; 3846; 3847; 3848; 3897; 3912; 3933; 3960; 3987; 3993; 4172; 4182; 4183; 4192; 4233; 4257; 4281; 4370; 4381; 4419; 4425; 4428; 4429; 4468; 4480; 4489; 4502; 4507; 4553; 4574; 4575; 4587; 4622; 4660; 4665; 4711; 4721; 4722; 4736; 4857; 4872; 4900; 4961; 5019; 5027; 5049; 5107; 5141; 5161; 5176; 5183; 5184; 5268; 5272; 5273; 5331; 5334; 5343; 5375; 5391; 5417; 5470; 5529 (see Table 1).

This combination permits correctly classifying 96.2% of the samples.

2.25. Identification of a Predictive Panel of 250 Markers (PANEL 23)

The inventors have demonstrated a combination of 250 markers, linked to an SVM algorithm, based on the sequences SEQ ID Nos: 26; 52; 58; 75; 98; 101; 103; 105; 114; 120; 163; 166; 171; 172; 277; 278; 300; 325; 354; 397; 398; 401; 403; 407; 419; 421; 424; 482; 511; 512; 518; 527; 531; 539; 569; 570; 571; 591; 596; 597; 598; 614; 619; 629; 658; 662; 668; 689; 690; 691; 694; 719; 721; 722; 789; 842; 872; 949; 1033; 1159; 1162; 1166; 1169; 1174; 1214; 1218; 1220; 1229; 1237; 1238; 1240; 1242; 1253; 1257; 1258; 1259; 1270; 1307; 1308; 1346; 1348; 1398; 1432; 1440; 1494; 1495; 1522; 1523; 1551; 1561; 1588; 1632; 1654; 1668; 1674; 1701; 1724; 1744; 1786; 1809; 1811; 1841; 1853; 1859; 1951; 1986; 2001; 2007; 2009; 2010; 2011; 2107; 2110; 2111; 2112; 2114; 2115; 2144; 2148; 2158; 2185; 2249; 2250; 2251; 2252; 2253; 2260; 2263; 2269; 2281; 2307; 2310; 2320; 2333; 2349; 2350; 2400; 2421; 2462; 2519; 2594; 2604; 2619; 2620; 2621; 2622; 2813; 2835; 2838; 2869; 2873; 2887; 2888; 2889; 2896; 2900; 2979; 3005; 3053; 3088; 3106; 3157; 3160; 3185; 3186; 3190; 3193; 3200; 3213; 3218; 3266; 3278; 3296; 3304; 3340; 3376; 3430; 3506; 3508; 3525; 3527; 3531; 3565; 3567; 3575; 3625; 3626; 3672; 3685; 3782; 3814; 3824; 3828; 3842; 3846; 3847; 3848; 3897; 3912; 3933; 3960; 3987; 3993; 4172; 4182; 4183; 4192; 4233; 4257; 4281; 4370; 4381; 4419; 4425; 4428; 4429; 4468; 4480; 4489; 4502; 4507; 4553; 4574; 4587; 4622; 4660; 4722; 4736; 4872; 4900; 4961; 5019; 5027; 5049; 5107; 5141; 5176; 5183; 5184; 5268; 5272; 5273; 5331; 5334; 5343; 5375; 5391; 5417; 5470; 5529 (see Table 1).

This combination permits correctly classifying 96.0% of the samples.

2.26. Identification of a Predictive Panel of 260 Markers (PANEL 24)

The inventors have demonstrated a combination of 260 markers, linked to an SVM algorithm, based on the sequences SEQ ID Nos: 26; 52; 58; 63; 75; 98; 101; 103; 105; 114; 117; 120; 163; 166; 171; 172; 277; 278; 300; 325; 338; 354; 397; 398; 401; 403; 407; 419; 421; 424; 482; 511; 512; 518; 527; 531; 539; 569; 570; 571; 591; 596; 597; 598; 614; 619; 629; 658; 662; 668; 689; 690; 691; 694; 719; 721; 722; 789; 842; 872; 949; 1033; 1159; 1162; 1166; 1169; 1174; 1214; 1218; 1220; 1229; 1237; 1238; 1240; 1242; 1253; 1257; 1258; 1259; 1270; 1307; 1308; 1346; 1348; 1398; 1432; 1440; 1494; 1495; 1522; 1523; 1551; 1561; 1588; 1624; 1632; 1654; 1668; 1674; 1701; 1724; 1744; 1786; 1809; 1811; 1841; 1853; 1859; 1951; 1986; 2001; 2003; 2007; 2009; 2010; 2011; 2107; 2110; 2111; 2112; 2114; 2115; 2144;

2148; 2158; 2185; 2249; 2250; 2251; 2252; 2253; 2260; 2263; 2269; 2281; 2307; 2310; 2320; 2333; 2349; 2350; 2400; 2421; 2442; 2462; 2519; 2594; 2604; 2619; 2620; 2621; 2622; 2813; 2835; 2838; 2869; 2873; 2887; 2888; 2889; 2896; 2900; 2979; 3005; 3053; 3088; 3106; 3157; 3160; 3185; 3186; 3190; 3193; 3200; 3213; 3218; 3266; 3278; 3296; 3304; 3340; 3376; 3430; 3506; 3508; 3525; 3527; 3531; 3565; 3566; 3567; 3575; 3625; 3626; 3672; 3685; 3782; 3814; 3816; 3824; 3828; 3842; 3846; 3847; 3848; 3897; 3912; 3933; 3960; 3987; 3993; 4172; 4182; 4183; 4192; 4233; 4257; 4281; 4370; 4381; 4419; 4425; 4428; 4429; 4468; 4480; 4489; 4502; 4507; 4553; 4574; 4575; 4587; 4622; 4660; 4711; 4722; 4736; 4872; 4900; 4961; 5019; 5027; 5049; 5107; 5141; 5176; 5183; 5184; 5268; 5272; 5273; 5331; 5334; 5343; 5375; 5391; 5417; 5470; 5529 (see Table 1).

This combination permits correctly classifying 96.0% of the samples.

2.27. Identification of a Predictive Panel of 230 Markers (PANEL 25)

The inventors have demonstrated a combination of 230 markers, linked to an SVM algorithm, based on the sequences SEQ ID Nos: 26; 52; 58; 75; 98; 101; 103; 105; 114; 120; 163; 166; 171; 172; 277; 278; 300; 325; 354; 397; 398; 403; 407; 419; 421; 424; 482; 511; 512; 518; 527; 531; 539; 569; 570; 571; 591; 596; 597; 598; 614; 619; 629; 658; 662; 689; 690; 691; 694; 719; 721; 872; 949; 1033; 1159; 1162; 1166; 1169; 1174; 1214; 1218; 1229; 1237; 1238; 1240; 1242; 1257; 1258; 1259; 1270; 1307; 1308; 1346; 1348; 1398; 1432; 1440; 1494; 1495; 1522; 1523; 1551; 1561; 1588; 1632; 1654; 1668; 1674; 1724; 1744; 1786; 1809; 1841; 1853; 1859; 1951; 1986; 2001; 2007; 2009; 2010; 2011; 2110; 2111; 2115; 2144; 2148; 2158; 2185; 2249; 2250; 2251; 2253; 2260; 2263; 2269; 2281; 2307; 2310; 2320; 2349; 2350; 2421; 2462; 2519; 2594; 2604; 2619; 2620; 2621; 2622; 2813; 2835; 2838; 2869; 2873; 2887; 2888; 2889; 2896; 2900; 2979; 3005; 3053; 3088; 3106; 3157; 3160; 3185; 3186; 3190; 3193; 3200; 3213; 3218; 3266; 3278; 3296; 3304; 3340; 3376; 3430; 3506; 3508; 3525; 3527; 3531; 3565; 3567; 3575; 3625; 3626; 3672; 3685; 3782; 3814; 3824; 3828; 3842; 3846; 3847; 3848; 3897; 3933; 3960; 3987; 3993; 4172; 4182; 4183; 4192; 4233; 4257; 4281; 4381; 4419; 4425; 4428; 4429; 4468; 4480; 4489; 4502; 4507; 4553; 4574; 4587; 4622; 4660; 4722; 4736; 4872; 4900; 4961; 5019; 5027; 5107; 5141; 5176; 5183; 5184; 5268; 5272; 5331; 5334; 5343; 5375; 5391; 5417; 5529 (see Table 1).

This combination permits correctly classifying 96.0% of the samples.

2.28. Identification of a Predictive Panel of 240 Markers (PANEL 26)

The inventors have demonstrated a combination of 240 markers, linked to an SVM algorithm, based on the sequences SEQ ID Nos: 26; 52; 58; 75; 98; 101; 103; 105; 114; 120; 163; 166; 171; 172; 277; 278; 300; 325; 354; 397; 398; 403; 407; 419; 421; 424; 482; 511; 512; 518; 527; 531; 539; 569; 570; 571; 591; 596; 597; 598; 614; 619; 629; 658; 662; 668; 689; 690; 691; 694; 719; 721; 722; 789; 872; 949; 1033; 1159; 1162; 1166; 1169; 1174; 1214; 1218; 1220; 1229; 1237; 1238; 1240; 1242; 1257; 1258; 1259; 1270; 1307; 1308; 1346; 1348; 1398; 1432; 1440; 1494; 1495; 1522; 1523; 1551; 1561; 1588; 1632; 1654; 1668; 1674; 1724; 1744; 1786; 1809; 1841; 1853; 1859; 1951; 1986; 2001; 2007; 2009; 2010; 2011; 2110; 2111; 2115; 2144; 2148; 2158; 2185; 2249; 2250; 2251; 2252; 2253; 2260; 2263; 2269; 2281; 2307; 2310; 2320; 2333; 2349; 2350; 2421; 2462; 2519; 2594; 2604; 2619; 2620; 2621; 2622; 2813; 2835; 2838; 2869; 2873; 2887; 2888; 2889; 2896; 2900; 2979; 3005; 3053; 3088; 3106; 3157; 3160; 3185; 3186; 3190; 3193; 3200; 3213; 3218; 3266; 3278; 3296; 3304; 3340; 3376; 3430; 3506; 3508; 3525; 3527; 3531; 3565; 3567; 3575; 3625; 3626; 3672; 3685; 3782; 3814; 3824; 3828; 3842; 3846; 3847; 3848; 3897; 3912; 3933; 3960; 3987; 3993; 4172; 4182; 4183; 4192; 4233; 4257; 4281; 4370; 4381; 4419; 4425; 4428; 4429; 4468; 4480; 4489; 4502; 4507; 4553; 4574; 4587; 4622; 4660; 4722; 4736; 4872; 4900; 4961; 5019; 5027; 5049; 5107; 5141; 5176; 5183; 5184; 5268; 5272; 5331; 5334; 5343; 5375; 5391; 5417; 5470; 5529 (see Table 1).

This combination permits correctly classifying 95.8% of the samples.

2.29. Identification of a Predictive Panel of 280 Markers (PANEL 27)

The inventors have demonstrated a combination of 280 markers, linked to an SVM algorithm, based on the sequences SEQ ID Nos: 26; 51; 52; 58; 63; 75; 98; 101; 103; 105; 114; 117; 120; 163; 166; 171; 172; 277; 278; 300; 325; 338; 354; 397; 398; 401; 403; 407; 419; 421; 424; 482; 511; 512; 518; 527; 531; 539; 569; 570; 571; 591; 596; 597; 598; 614; 619; 629; 658; 662; 668; 689; 690; 691; 694; 719; 721; 722; 789; 842; 872; 921; 949; 958; 1032; 1033; 1159; 1162; 1166; 1169; 1174; 1185; 1214; 1218; 1220; 1229; 1237; 1238; 1240; 1242; 1253; 1257; 1258; 1259; 1270; 1307; 1308; 1346; 1348; 1398; 1432; 1440; 1494; 1495; 1522; 1523; 1551; 1561; 1588; 1624; 1632; 1654; 1668; 1674; 1701; 1724; 1744; 1767; 1786; 1809; 1811; 1841; 1853; 1859; 1951; 1986; 2001; 2003; 2007; 2009; 2010; 2011; 2106; 2107; 2110; 2111; 2112; 2114; 2115; 2144; 2148; 2158; 2185; 2249; 2250; 2251; 2252; 2253; 2260; 2263; 2269; 2281; 2307; 2310; 2320; 2333; 2349; 2350; 2400; 2421; 2442; 2462; 2519; 2594; 2599; 2604; 2619; 2620; 2621; 2622; 2813; 2835; 2838; 2869; 2873; 2887; 2888; 2889; 2891; 2896; 2900; 2979; 3005; 3053; 3088; 3106; 3157; 3160; 3185; 3186; 3190; 3193; 3200; 3213; 3218; 3266; 3278; 3296; 3304; 3340; 3376; 3430; 3506; 3508; 3520; 3525; 3527; 3531; 3565; 3566; 3567; 3575; 3624; 3625; 3626; 3672; 3685; 3782; 3814; 3816; 3824; 3826; 3828; 3842; 3843; 3846; 3847; 3848; 3897; 3912; 3933; 3960; 3987; 3993; 4065; 4172; 4182; 4183; 4192; 4233; 4257; 4281; 4370; 4381; 4419; 4425; 4428; 4429; 4468; 4480; 4489; 4502; 4507; 4553; 4574; 4575; 4587; 4622; 4660; 4665; 4700; 4711; 4721; 4722; 4736; 4857; 4872; 4900; 4961; 5019; 5027; 5049; 5107; 5123; 5141; 5161; 5176; 5183; 5184; 5268; 5272; 5273; 5331; 5334; 5343; 5375; 5391; 5417; 5470; 5529 (see Table 1).

This combination permits correctly classifying 95.8% of the samples.

2.30. Identification of a Predictive Panel of 290 Markers (PANEL 28)

The inventors have demonstrated a combination of 290 markers, linked to an SVM algorithm, based on the sequences SEQ ID Nos: 26; 51; 52; 58; 63; 75; 98; 101; 103; 105; 114; 117; 120; 163; 166; 171; 172; 277; 278; 300; 325; 338; 354; 397; 398; 401; 403; 407; 419; 421; 424; 480; 482; 511; 512; 518; 527; 531; 539; 569; 570; 571; 591; 596; 597; 598; 614; 619; 629; 658; 662; 668; 689; 690; 691; 693; 694; 719; 721; 722; 789; 842; 871; 872; 921; 949; 958; 1032; 1033; 1159; 1162; 1166; 1169; 1174; 1185; 1214; 1218; 1220; 1229; 1237; 1238; 1240; 1242; 1253; 1257; 1258; 1259; 1270; 1307; 1308; 1346; 1348; 1398; 1432; 1440; 1494; 1495; 1522; 1523; 1551; 1561; 1588; 1624; 1632; 1654; 1668; 1674; 1701; 1724; 1744; 1767; 1786; 1809; 1811; 1841; 1853; 1859; 1951; 1986; 2001; 2003; 2007; 2009; 2010; 2011; 2085; 2106; 2107; 2110; 2111; 2112; 2114; 2115;

2144; 2148; 2158; 2185; 2249; 2250; 2251; 2252; 2253; 2260; 2263; 2269; 2281; 2307; 2310; 2320; 2333; 2349; 2350; 2400; 2421; 2442; 2462; 2519; 2594; 2596; 2599; 2604; 2619; 2620; 2621; 2622; 2679; 2813; 2835; 2838; 2869; 2873; 2887; 2888; 2889; 2891; 2896; 2900; 2979; 3005; 3053; 3088; 3106; 3157; 3160; 3185; 3186; 3190; 3193; 3200; 3213; 3218; 3266; 3278; 3296; 3304; 3340; 3376; 3430; 3506; 3508; 3520; 3525; 3527; 3531; 3565; 3566; 3567; 3573; 3574; 3575; 3624; 3625; 3626; 3672; 3685; 3782; 3814; 3816; 3824; 3826; 3828; 3842; 3843; 3846; 3847; 3848; 3897; 3912; 3933; 3960; 3987; 3993; 4065; 4172; 4182; 4183; 4192; 4199; 4233; 4257; 4281; 4370; 4381; 4419; 4425; 4428; 4429; 4468; 4480; 4489; 4502; 4507; 4553; 4574; 4575; 4587; 4622; 4660; 4665; 4700; 4711; 4712; 4721; 4722; 4736; 4857; 4872; 4900; 4961; 5019; 5027; 5049; 5107; 5123; 5141; 5161; 5176; 5183; 5184; 5268; 5272; 5273; 5331; 5334; 5343; 5375; 5391; 5417; 5470; 5529 (see Table 1).

This combination permits correctly classifying 95.8% of the samples.

2.31. Identification of a Predictive Panel of 220 Markers (PANEL 29)

The inventors have demonstrated a combination of 220 markers, linked to an SVM algorithm, based on the sequences SEQ ID Nos: 26; 52; 58; 75; 98; 103; 105; 114; 120; 163; 166; 171; 172; 277; 278; 300; 325; 354; 397; 398; 407; 419; 421; 424; 482; 511; 512; 518; 527; 539; 569; 570; 571; 591; 596; 597; 598; 614; 619; 629; 658; 662; 689; 691; 694; 719; 721; 872; 949; 1033; 1159; 1162; 1166; 1169; 1174; 1214; 1218; 1229; 1237; 1238; 1240; 1242; 1257; 1258; 1259; 1270; 1307; 1308; 1346; 1348; 1398; 1432; 1440; 1494; 1495; 1522; 1523; 1551; 1588; 1632; 1654; 1668; 1674; 1724; 1744; 1786; 1809; 1841; 1853; 1859; 1951; 1986; 2001; 2007; 2009; 2010; 2011; 2110; 2115; 2144; 2185; 2249; 2250; 2251; 2253; 2260; 2263; 2269; 2281; 2307; 2310; 2320; 2349; 2350; 2421; 2462; 2519; 2594; 2604; 2619; 2620; 2621; 2622; 2813; 2835; 2838; 2869; 2873; 2887; 2888; 2889; 2896; 2900; 2979; 3005; 3053; 3088; 3106; 3157; 3160; 3185; 3186; 3190; 3193; 3200; 3213; 3218; 3266; 3278; 3304; 3340; 3376; 3430; 3506; 3508; 3525; 3527; 3531; 3565; 3567; 3575; 3625; 3626; 3672; 3685; 3782; 3814; 3824; 3828; 3842; 3846; 3847; 3848; 3897; 3933; 3960; 3987; 3993; 4172; 4182; 4192; 4233; 4257; 4281; 4381; 4419; 4425; 4428; 4429; 4468; 4480; 4489; 4502; 4507; 4553; 4574; 4587; 4622; 4660; 4722; 4736; 4872; 4900; 4961; 5019; 5027; 5107; 5141; 5176; 5183; 5184; 5268; 5272; 5331; 5334; 5343; 5375; 5391; 5417; 5529 (see Table 1).

This combination permits correctly classifying 95.8% of the samples.

2.32. Identification of a Predictive Panel of 200 Markers (PANEL 30)

The inventors have demonstrated a combination of 200 markers, linked to an SVM algorithm, based on the sequences SEQ ID Nos: 26; 52; 58; 75; 103; 105; 120; 163; 166; 171; 172; 277; 278; 300; 325; 354; 397; 398; 419; 421; 424; 482; 512; 518; 527; 539; 569; 570; 571; 591; 596; 597; 598; 614; 619; 629; 658; 662; 689; 694; 719; 721; 872; 949; 1033; 1159; 1162; 1166; 1174; 1214; 1218; 1229; 1237; 1238; 1240; 1242; 1258; 1259; 1270; 1307; 1308; 1346; 1348; 1432; 1440; 1494; 1495; 1522; 1523; 1588; 1632; 1654; 1668; 1674; 1724; 1744; 1786; 1841; 1853; 1859; 1951; 1986; 2001; 2007; 2009; 2010; 2110; 2115; 2144; 2185; 2249; 2250; 2251; 2253; 2260; 2263; 2269; 2281; 2307; 2310; 2320; 2349; 2350; 2421; 2462; 2519; 2594; 2604; 2619; 2620; 2621; 2622; 2813; 2835; 2838; 2869; 2873; 2887; 2888; 2889; 2896; 2900; 2979; 3005; 3053; 3088; 3106; 3157; 3160; 3185; 3186; 3190; 3193; 3200; 3213; 3266; 3304; 3340; 3376; 3430; 3508; 3525; 3527; 3531; 3565; 3567; 3575; 3625; 3672; 3685; 3782; 3814; 3824; 3828; 3842; 3846; 3847; 3848; 3897; 3960; 3993; 4172; 4182; 4192; 4233; 4257; 4281; 4381; 4419; 4425; 4428; 4429; 4468; 4489; 4507; 4553; 4574; 4587; 4622; 4660; 4722; 4736; 4872; 4900; 4961; 5019; 5027; 5107; 5141; 5176; 5183; 5184; 5268; 5272; 5331; 5334; 5343; 5391; 5417; 5529 (see Table 1).

This combination permits correctly classifying 95.8% of the samples.

2.33. Identification of a Predictive Panel of 230 Markers (PANEL 31)

The inventors have demonstrated a combination of 230 markers, linked to an SVM algorithm, based on the sequences SEQ ID Nos: 26; 52; 58; 75; 98; 101; 103; 105; 114; 120; 163; 166; 171; 172; 277; 278; 300; 325; 354; 397; 398; 403; 407; 419; 421; 424; 482; 511; 512; 518; 527; 531; 539; 569; 570; 571; 591; 596; 597; 598; 614; 619; 629; 658; 662; 689; 690; 691; 694; 719; 721; 872; 949; 1033; 1159; 1162; 1166; 1169; 1174; 1214; 1218; 1229; 1237; 1238; 1240; 1242; 1257; 1258; 1259; 1270; 1307; 1308; 1346; 1348; 1398; 1432; 1440; 1494; 1495; 1522; 1523; 1551; 1561; 1588; 1632; 1654; 1668; 1674; 1724; 1744; 1786; 1809; 1841; 1853; 1859; 1951; 1986; 2001; 2007; 2009; 2010; 2011; 2110; 2111; 2115; 2144; 2148; 2158; 2185; 2249; 2250; 2251; 2253; 2260; 2263; 2269; 2281; 2307; 2310; 2320; 2349; 2350; 2421; 2462; 2519; 2594; 2604; 2619; 2620; 2621; 2622; 2813; 2835; 2838; 2869; 2873; 2887; 2888; 2889; 2896; 2900; 2979; 3005; 3053; 3088; 3106; 3157; 3160; 3185; 3186; 3190; 3193; 3200; 3213; 3218; 3266; 3278; 3296; 3304; 3340; 3376; 3430; 3506; 3508; 3525; 3527; 3531; 3565; 3567; 3575; 3625; 3626; 3672; 3685; 3782; 3814; 3824; 3828; 3842; 3846; 3847; 3848; 3897; 3933; 3960; 3987; 3993; 4172; 4182; 4183; 4192; 4233; 4257; 4281; 4381; 4419; 4425; 4428; 4429; 4468; 4480; 4489; 4502; 4507; 4553; 4574; 4587; 4622; 4660; 4722; 4736; 4872; 4900; 4961; 5019; 5027; 5107; 5141; 5176; 5183; 5184; 5268; 5272; 5331; 5334; 5343; 5375; 5391; 5417; 5529 (see Table 1).

This combination permits correctly classifying 95.8% of the samples.

2.34. Identification of a Predictive Panel of 230 Markers (PANEL 32)

The inventors have demonstrated a combination of 230 markers, linked to an SVM algorithm, based on the sequences SEQ ID Nos: 26; 52; 58; 75; 98; 101; 103; 105; 114; 120; 163; 166; 171; 172; 277; 278; 300; 325; 354; 397; 398; 403; 407; 419; 421; 424; 482; 511; 512; 518; 527; 531; 539; 569; 570; 571; 591; 596; 597; 598; 614; 619; 629; 658; 662; 689; 690; 691; 694; 719; 721; 872; 949; 1033; 1159; 1162; 1166; 1169; 1174; 1214; 1218; 1229; 1237; 1238; 1240; 1242; 1257; 1258; 1259; 1270; 1307; 1308; 1346; 1348; 1398; 1432; 1440; 1494; 1495; 1522; 1523; 1551; 1561; 1588; 1632; 1654; 1668; 1674; 1724; 1744; 1786; 1809; 1841; 1853; 1859; 1951; 1986; 2001; 2007; 2009; 2010; 2011; 2110; 2111; 2115; 2144; 2148; 2158; 2185; 2249; 2250; 2251; 2253; 2260; 2263; 2269; 2281; 2307; 2310; 2320; 2349; 2350; 2421; 2462; 2519; 2594; 2604; 2619; 2620; 2621; 2622; 2813; 2835; 2838; 2869; 2873; 2887; 2888; 2889; 2896; 2900; 2979; 3005; 3053; 3088; 3106; 3157; 3160; 3185; 3186; 3190; 3193; 3200; 3213; 3218; 3266; 3278; 3296; 3304; 3340; 3376; 3430; 3506; 3508; 3525; 3527; 3531; 3565; 3567; 3575; 3625; 3626; 3672; 3685; 3782; 3814; 3824; 3828; 3842; 3846; 3847; 3848; 3897; 3933; 3960; 3987; 3993; 4172; 4182; 4183; 4192; 4233; 4257; 4281; 4381; 4419; 4425; 4428; 4429; 4468; 4480; 4489;

4502; 4507; 4553; 4574; 4587; 4622; 4660; 4722; 4736; 4872; 4900; 4961; 5019; 5027; 5107; 5141; 5176; 5183; 5184; 5268; 5272; 5331; 5334; 5343; 5375; 5391; 5417; 5529 (see Table 1).

This combination permits correctly classifying 95.8% of the samples.

2.35. Identification of a Predictive Panel of 300 Markers (PANEL 33)

The inventors have demonstrated a combination of 300 markers, linked to an SVM algorithm, based on the sequences SEQ ID Nos: 26; 51; 52; 58; 63; 75; 98; 101; 103; 105; 114; 117; 120; 163; 166; 171; 172; 277; 278; 300; 325; 338; 354; 397; 398; 401; 403; 407; 419; 421; 424; 480; 482; 511; 512; 518; 527; 531; 539; 569; 570; 571; 591; 596; 597; 598; 614; 619; 629; 658; 662; 668; 689; 690; 691; 693; 694; 719; 721; 722; 789; 842; 871; 872; 921; 949; 958; 1032; 1033; 1159; 1162; 1166; 1169; 1174; 1185; 1214; 1218; 1220; 1229; 1237; 1238; 1240; 1242; 1253; 1257; 1258; 1259; 1270; 1307; 1308; 1346; 1348; 1398; 1421; 1432; 1440; 1494; 1495; 1522; 1523; 1551; 1561; 1588; 1624; 1632; 1654; 1668; 1674; 1701; 1724; 1744; 1767; 1786; 1809; 1811; 1841; 1853; 1859; 1951; 1986; 2001; 2003; 2007; 2009; 2010; 2011; 2085; 2106; 2107; 2110; 2111; 2112; 2114; 2115; 2144; 2148; 2158; 2185; 2249; 2250; 2251; 2252; 2253; 2260; 2263; 2266; 2269; 2281; 2307; 2310; 2320; 2333; 2349; 2350; 2400; 2421; 2442; 2462; 2519; 2594; 2596; 2599; 2604; 2619; 2620; 2621; 2622; 2679; 2703; 2813; 2835; 2838; 2869; 2873; 2887; 2888; 2889; 2891; 2896; 2900; 2979; 3005; 3053; 3088; 3106; 3157; 3160; 3185; 3186; 3190; 3193; 3200; 3213; 3218; 3266; 3276; 3278; 3296; 3304; 3340; 3376; 3430; 3506; 3508; 3520; 3525; 3527; 3531; 3565; 3566; 3567; 3573; 3574; 3575; 3624; 3625; 3626; 3672; 3685; 3782; 3814; 3816; 3824; 3826; 3828; 3842; 3843; 3844; 3845; 3846; 3847; 3848; 3897; 3912; 3933; 3960; 3987; 3993; 4065; 4172; 4182; 4183; 4192; 4199; 4233; 4257; 4281; 4370; 4381; 4419; 4425; 4428; 4429; 4468; 4480; 4489; 4502; 4507; 4553; 4574; 4575; 4587; 4622; 4660; 4665; 4700; 4711; 4712; 4721; 4722; 4736; 4857; 4872; 4900; 4961; 5019; 5027; 5049; 5107; 5123; 5141; 5161; 5162; 5176; 5183; 5184; 5185; 5268; 5272; 5273; 5330; 5331; 5334; 5343; 5375; 5391; 5417; 5470; 5513; 5529 (see Table 1).

This combination permits correctly classifying 95.8% of the samples.

2.36. Identification of a Predictive Panel of 160 Markers (PANEL 34)

The inventors have demonstrated a combination of 160 markers, linked to an SVM algorithm, based on the sequences SEQ ID Nos: 26; 58; 75; 103; 105; 120; 166; 171; 172; 278; 325; 354; 397; 398; 419; 421; 424; 482; 518; 527; 539; 570; 571; 591; 597; 598; 619; 629; 658; 662; 689; 721; 872; 1033; 1159; 1162; 1166; 1174; 1218; 1229; 1237; 1238; 1240; 1242; 1258; 1259; 1270; 1307; 1346; 1432; 1440; 1495; 1522; 1523; 1588; 1632; 1654; 1668; 1674; 1744; 1786; 1841; 1853; 1859; 1951; 1986; 2001; 2007; 2009; 2010; 2110; 2115; 2144; 2185; 2249; 2251; 2263; 2269; 2307; 2310; 2349; 2350; 2421; 2462; 2519; 2594; 2619; 2620; 2621; 2622; 2813; 2835; 2838; 2873; 2887; 2888; 2889; 2896; 2900; 2979; 3005; 3053; 3088; 3160; 3185; 3186; 3190; 3193; 3200; 3213; 3304; 3376; 3430; 3508; 3527; 3531; 3565; 3567; 3575; 3625; 3672; 3685; 3824; 3842; 3846; 3847; 3848; 3897; 3960; 3993; 4172; 4182; 4192; 4257; 4281; 4419; 4425; 4428; 4429; 4468; 4507; 4553; 4660; 4722; 4872; 4900; 4961; 5019; 5027; 5107; 5141; 5176; 5183; 5184; 5268; 5272; 5334; 5343; 5391; 5417 (see Table 1).

This combination permits correctly classifying 95.6% of the samples.

2.37. Identification of a Predictive Panel of 150 Markers (Panel 35)

The inventors have demonstrated a combination of 150 markers, linked to an SVM algorithm, based on the sequences SEQ ID Nos: 26; 58; 75; 103; 105; 120; 166; 171; 172; 278; 325; 354; 397; 398; 419; 421; 482; 518; 527; 539; 570; 571; 591; 597; 598; 619; 629; 658; 662; 689; 721; 872; 1033; 1159; 1162; 1174; 1218; 1229; 1237; 1238; 1240; 1258; 1259; 1270; 1307; 1346; 1432; 1440; 1495; 1522; 1523; 1588; 1632; 1654; 1668; 1674; 1744; 1786; 1841; 1853; 1859; 1951; 1986; 2001; 2007; 2009; 2010; 2110; 2115; 2249; 2251; 2263; 2269; 2307; 2310; 2349; 2350; 2421; 2462; 2519; 2594; 2619; 2620; 2621; 2622; 2813; 2835; 2838; 2873; 2887; 2888; 2889; 2896; 2900; 2979; 3005; 3053; 3088; 3160; 3185; 3186; 3190; 3193; 3200; 3304; 3376; 3430; 3508; 3527; 3531; 3565; 3567; 3575; 3672; 3685; 3824; 3842; 3846; 3847; 3848; 3897; 3960; 3993; 4172; 4182; 4192; 4257; 4419; 4425; 4428; 4429; 4468; 4507; 4553; 4660; 4722; 4872; 4961; 5019; 5027; 5107; 5176; 5183; 5184; 5268; 5272; 5334; 5343; 5391; 5417 (see Table 1).

This combination permits correctly classifying 95.6% of the samples.

2.38. Identification of a Predictive Panel of 170 Markers (PANEL 36)

The inventors have demonstrated a combination of 170 markers, linked to an SVM algorithm, based on the sequences SEQ ID Nos: 26; 58; 75; 103; 105; 120; 166; 171; 172; 278; 325; 354; 397; 398; 419; 421; 424; 482; 512; 518; 527; 539; 570; 571; 591; 597; 598; 619; 629; 658; 662; 689; 694; 721; 872; 1033; 1159; 1162; 1166; 1174; 1218; 1229; 1237; 1238; 1240; 1242; 1258; 1259; 1270; 1307; 1308; 1346; 1432; 1440; 1495; 1522; 1523; 1588; 1632; 1654; 1668; 1674; 1744; 1786; 1841; 1853; 1859; 1951; 1986; 2001; 2007; 2009; 2010; 2110; 2115; 2144; 2185; 2249; 2251; 2253; 2263; 2269; 2307; 2310; 2320; 2349; 2350; 2421; 2462; 2519; 2594; 2619; 2620; 2621; 2622; 2813; 2835; 2838; 2873; 2887; 2888; 2889; 2896; 2900; 2979; 3005; 3053; 3088; 3160; 3185; 3186; 3190; 3193; 3200; 3213; 3266; 3304; 3376; 3430; 3508; 3525; 3527; 3531; 3565; 3567; 3575; 3625; 3672; 3685; 3824; 3828; 3842; 3846; 3847; 3848; 3897; 3960; 3993; 4172; 4182; 4192; 4233; 4257; 4281; 4381; 4419; 4425; 4428; 4429; 4468; 4507; 4553; 4660; 4722; 4872; 4900; 4961; 5019; 5027; 5107; 5141; 5176; 5183; 5184; 5268; 5272; 5334; 5343; 5391; 5417 (see Table 1).

This combination permits correctly classifying 95.6% of the samples.

2.39. Identification of a Predictive Panel of 180 Markers (PANEL 37)

The inventors have demonstrated a combination of 180 markers, linked to an SVM algorithm, based on the sequences SEQ ID Nos: 26; 58; 75; 103; 105; 120; 166; 171; 172; 278; 300; 325; 354; 397; 398; 419; 421; 424; 482; 512; 518; 527; 539; 569; 570; 571; 591; 596; 597; 598; 619; 629; 658; 662; 689; 694; 721; 872; 949; 1033; 1159; 1162; 1166; 1174; 1218; 1229; 1237; 1238; 1240; 1242; 1258; 1259; 1270; 1307; 1308; 1346; 1348; 1432; 1440; 1495; 1522; 1523; 1588; 1632; 1654; 1668; 1674; 1744; 1786; 1841; 1853; 1859; 1951; 1986; 2001; 2007; 2009; 2010; 2110; 2115; 2144; 2185; 2249; 2251; 2253; 2263; 2269; 2307; 2310; 2320; 2349; 2350; 2421; 2462; 2519; 2594; 2619; 2620; 2621; 2622; 2813; 2835; 2838; 2873; 2887; 2888; 2889; 2896; 2900; 2979; 3005; 3053; 3088; 3106; 3160; 3185; 3186; 3190; 3193; 3200; 3213; 3266; 3304; 3340; 3376;

3430; 3508; 3525; 3527; 3531; 3565; 3567; 3575; 3625; 3672; 3685; 3814; 3824; 3828; 3842; 3846; 3847; 3848; 3897; 3960; 3993; 4172; 4182; 4192; 4233; 4257; 4281; 4381; 4419; 4425; 4428; 4429; 4468; 4507; 4553; 4622; 4660; 4722; 4736; 4872; 4900; 4961; 5019; 5027; 5107; 5141; 5176; 5183; 5184; 5268; 5272; 5334; 5343; 5391; 5417 (see Table 1).

This combination permits correctly classifying 95.6% of the samples.

2.40. Identification of a Predictive Panel of 190 Markers (PANEL 38)

The inventors have demonstrated a combination of 190 markers, linked to an SVM algorithm, based on the sequences SEQ ID Nos: 26; 52; 58; 75; 103; 105; 120; 163; 166; 171; 172; 277; 278; 300; 325; 354; 397; 398; 419; 421; 424; 482; 512; 518; 527; 539; 569; 570; 571; 591; 596; 597; 598; 614; 619; 629; 658; 662; 689; 694; 719; 721; 872; 949; 1033; 1159; 1162; 1166; 1174; 1218; 1229; 1237; 1238; 1240; 1242; 1258; 1259; 1270; 1307; 1308; 1346; 1348; 1432; 1440; 1495; 1522; 1523; 1588; 1632; 1654; 1668; 1674; 1744; 1786; 1841; 1853; 1859; 1951; 1986; 2001; 2007; 2009; 2010; 2110; 2115; 2144; 2185; 2249; 2251; 2253; 2263; 2269; 2307; 2310; 2320; 2349; 2350; 2421; 2462; 2519; 2594; 2619; 2620; 2621; 2622; 2813; 2835; 2838; 2869; 2873; 2887; 2888; 2889; 2896; 2900; 2979; 3005; 3053; 3088; 3106; 3157; 3160; 3185; 3186; 3190; 3193; 3200; 3213; 3266; 3304; 3340; 3376; 3430; 3508; 3525; 3527; 3531; 3565; 3567; 3575; 3625; 3672; 3685; 3814; 3824; 3828; 3842; 3846; 3847; 3848; 3897; 3960; 3993; 4172; 4182; 4192; 4233; 4257; 4281; 4381; 4419; 4425; 4428; 4429; 4468; 4507; 4553; 4574; 4587; 4622; 4660; 4722; 4736; 4872; 4900; 4961; 5019; 5027; 5107; 5141; 5176; 5183; 5184; 5268; 5272; 5331; 5334; 5343; 5391; 5417 (see Table 1).

This combination permits correctly classifying 95.6% of the samples.

2.41. Identification of a Predictive Panel of 150 Markers (PANEL 39)

The inventors have demonstrated a combination of 150 markers, linked to an SVM algorithm, based on the sequences SEQ ID Nos: 26; 58; 75; 103; 105; 120; 166; 171; 172; 278; 325; 354; 397; 398; 419; 421; 482; 518; 527; 539; 570; 571; 591; 597; 598; 619; 629; 658; 662; 689; 721; 872; 1033; 1159; 1162; 1174; 1218; 1229; 1237; 1238; 1240; 1258; 1259; 1270; 1307; 1346; 1432; 1440; 1495; 1522; 1523; 1588; 1632; 1654; 1668; 1674; 1744; 1786; 1841; 1853; 1859; 1951; 1986; 2001; 2007; 2009; 2010; 2110; 2115; 2249; 2251; 2263; 2269; 2307; 2310; 2349; 2350; 2421; 2462; 2519; 2594; 2619; 2620; 2621; 2622; 2813; 2835; 2838; 2873; 2887; 2888; 2889; 2896; 2900; 2979; 3005; 3053; 3088; 3160; 3185; 3186; 3190; 3193; 3200; 3304; 3376; 3430; 3508; 3527; 3531; 3565; 3567; 3575; 3672; 3685; 3824; 3842; 3846; 3847; 3848; 3897; 3960; 3993; 4172; 4182; 4192; 4257; 4419; 4425; 4428; 4429; 4468; 4507; 4553; 4660; 4722; 4872; 4961; 5019; 5027; 5107; 5176; 5183; 5184; 5268; 5272; 5334; 5343; 5391; 5417 (see Table 1).

This combination permits correctly classifying 95.6% of the samples.

2.42. Identification of a Predictive Panel of 150 Markers (PANEL 40)

The inventors have demonstrated a combination of 150 markers, linked to an SVM algorithm, based on the sequences SEQ ID Nos: 26; 58; 75; 103; 105; 120; 166; 171; 172; 278; 325; 354; 397; 398; 419; 421; 482; 518; 527; 539; 570; 571; 591; 597; 598; 619; 629; 658; 662; 689; 721; 872; 1033; 1159; 1162; 1174; 1218; 1229; 1237; 1238; 1240; 1258; 1259; 1270; 1307; 1346; 1432; 1440; 1495; 1522; 1523; 1588; 1632; 1654; 1668; 1674; 1744; 1786; 1841; 1853; 1859; 1951; 1986; 2001; 2007; 2009; 2010; 2110; 2115; 2249; 2251; 2263; 2269; 2307; 2310; 2349; 2350; 2421; 2462; 2519; 2594; 2619; 2620; 2621; 2622; 2813; 2835; 2838; 2873; 2887; 2888; 2889; 2896; 2900; 2979; 3005; 3053; 3088; 3160; 3185; 3186; 3190; 3193; 3200; 3304; 3376; 3430; 3508; 3527; 3531; 3565; 3567; 3575; 3672; 3685; 3824; 3842; 3846; 3847; 3848; 3897; 3960; 3993; 4172; 4182; 4192; 4257; 4419; 4425; 4428; 4429; 4468; 4507; 4553; 4660; 4722; 4872; 4961; 5019; 5027; 5107; 5176; 5183; 5184; 5268; 5272; 5334; 5343; 5391; 5417 (see Table 1).

This combination permits correctly classifying 95.6% of the samples.

2.43. Identification of a Predictive Panel of 210 Markers (PANEL 41)

The inventors have demonstrated a combination of 210 markers, linked to an SVM algorithm, based on the sequences SEQ ID Nos: 26; 52; 58; 75; 103; 105; 114; 120; 163; 166; 171; 172; 277; 278; 300; 325; 354; 397; 398; 407; 419; 421; 424; 482; 512; 518; 527; 539; 569; 570; 571; 591; 596; 597; 598; 614; 619; 629; 658; 662; 689; 694; 719; 721; 872; 949; 1033; 1159; 1162; 1166; 1169; 1174; 1214; 1218; 1229; 1237; 1238; 1240; 1242; 1258; 1259; 1270; 1307; 1308; 1346; 1348; 1432; 1440; 1494; 1495; 1522; 1523; 1551; 1588; 1632; 1654; 1668; 1674; 1724; 1744; 1786; 1841; 1853; 1859; 1951; 1986; 2001; 2007; 2009; 2010; 2110; 2115; 2144; 2185; 2249; 2250; 2251; 2253; 2260; 2263; 2269; 2281; 2307; 2310; 2320; 2349; 2350; 2421; 2462; 2519; 2594; 2604; 2619; 2620; 2621; 2622; 2813; 2835; 2838; 2869; 2873; 2887; 2888; 2889; 2896; 2900; 2979; 3005; 3053; 3088; 3106; 3157; 3160; 3185; 3186; 3190; 3193; 3200; 3213; 3218; 3266; 3278; 3304; 3340; 3376; 3430; 3506; 3508; 3525; 3527; 3531; 3565; 3567; 3575; 3625; 3626; 3672; 3685; 3782; 3814; 3824; 3828; 3842; 3846; 3847; 3848; 3897; 3960; 3993; 4172; 4182; 4192; 4233; 4257; 4281; 4381; 4419; 4425; 4428; 4429; 4468; 4480; 4489; 4507; 4553; 4574; 4587; 4622; 4660; 4722; 4736; 4872; 4900; 4961; 5019; 5027; 5107; 5141; 5176; 5183; 5184; 5268; 5272; 5331; 5334; 5343; 5375; 5391; 5417; 5529 (see Table 1).

This combination permits correctly classifying 95.6% of the samples.

2.44. Identification of a Predictive Panel of 170 Markers (PANEL 42)

The inventors have demonstrated a combination of 170 markers, linked to an SVM algorithm, based on the sequences SEQ ID Nos: 26; 58; 75; 103; 105; 120; 166; 171; 172; 278; 325; 354; 397; 398; 419; 421; 424; 482; 512; 518; 527; 539; 570; 571; 591; 597; 598; 619; 629; 658; 662; 689; 694; 721; 872; 1033; 1159; 1162; 1166; 1174; 1218; 1229; 1237; 1238; 1240; 1242; 1258; 1259; 1270; 1307; 1308; 1346; 1432; 1440; 1495; 1522; 1523; 1588; 1632; 1654; 1668; 1674; 1744; 1786; 1841; 1853; 1859; 1951; 1986; 2001; 2007; 2009; 2010; 2110; 2115; 2144; 2185; 2249; 2251; 2253; 2263; 2269; 2307; 2310; 2320; 2349; 2350; 2421; 2462; 2519; 2594; 2619; 2620; 2621; 2622; 2813; 2835; 2838; 2873; 2887; 2888; 2889; 2896; 2900; 2979; 3005; 3053; 3088; 3160; 3185; 3186; 3190; 3193; 3200; 3213; 3266; 3304; 3376; 3430; 3508; 3525; 3527; 3531; 3565; 3567; 3575; 3625; 3672; 3685; 3824; 3828; 3842; 3846; 3847; 3848; 3897; 3960; 3993; 4172; 4182; 4192; 4233; 4257; 4281; 4381; 4419; 4425; 4428; 4429; 4468; 4507; 4553; 4660; 4722; 4872; 4900; 4961; 5019; 5027; 5107; 5141; 5176; 5183; 5184; 5268; 5272; 5334; 5343; 5391; 5417 (see Table 1).

This combination permits correctly classifying 95.4% of the samples.

2.45. Identification of a Predictive Panel of 60 Markers (PANEL 43)

The inventors have demonstrated a combination of 60 markers, linked to an SVM algorithm, based on the sequences SEQ ID Nos: 26; 58; 105; 120; 166; 325; 354; 397; 398; 570; 571; 598; 619; 629; 721; 1033; 1218; 1229; 1237; 1238; 1258; 1259; 1270; 1346; 1432; 1440; 1495; 1588; 1632; 1668; 1853; 1859; 2009; 2269; 2594; 2620; 2622; 2838; 2887; 3200; 3304; 3430; 3508; 3527; 3575; 3960; 3993; 4192; 4419; 4428; 4429; 4660; 4722; 4961; 5107; 5176; 5183; 5184; 5391; 5417 (see Table 1).

This combination permits correctly classifying 95.2% of the samples.

2.46. Identification of a Predictive Panel of 190 Markers (PANEL 44)

The inventors have demonstrated a combination of 190 markers, linked to an SVM algorithm, based on the sequences SEQ ID Nos: 1; 6; 28; 73; 321; 323; 343; 350; 352; 397; 417; 418; 513; 538; 542; 612; 720; 788; 852; 990; 991; 1152; 1154; 1169; 1212; 1237; 1239; 1242; 1326; 1489; 1490; 1641; 1683; 1694; 1711; 1723; 1731; 1741; 1744; 1747; 1749; 1789; 1800; 1831; 1833; 1834; 1837; 1859; 1950; 1951; 1952; 1953; 1984; 1994; 1995; 2023; 2038; 2117; 2126; 2127; 2128; 2129; 2130; 2132; 2133; 2143; 2144; 2209; 2284; 2305; 2365; 2372; 2375; 2378; 2380; 2382; 2390; 2399; 2406; 2411; 2458; 2459; 2462; 2469; 2528; 2529; 2532; 2533; 2534; 2538; 2542; 2543; 2556; 2563; 2564; 2652; 2679; 2703; 2708; 2709; 2725; 2727; 2732; 2740; 2887; 2888; 2900; 2941; 2942; 2943; 2944; 3043; 3057; 3092; 3286; 3384; 3387; 3574; 3596; 3600; 3673; 3690; 3767; 3782; 3807; 3810; 3811; 3822; 3857; 3862; 3904; 3920; 3936; 3940; 3958; 4019; 4076; 4093; 4094; 4096; 4130; 4295; 4297; 4345; 4350; 4351; 4428; 4434; 4442; 4468; 4493; 4497; 4510; 4515; 4546; 4596; 4603; 4706; 4736; 4744; 4804; 4860; 4885; 4888; 4889; 4890; 4891; 4892; 4897; 4898; 4899; 4918; 4955; 4975; 4976; 4978; 4982; 5017; 5067; 5080; 5144; 5198; 5221; 5238; 5380; 5383; 5450; 5529; 5532; 5555 (see Table 1).

This combination permits correctly classifying 92.8% of the samples.

2.47. Identification of a Predictive Panel of 170 Markers (PANEL 45)

The inventors have demonstrated a combination of 170 markers, linked to an SVM algorithm, based on the sequences SEQ ID Nos: 1; 28; 73; 321; 323; 350; 397; 417; 418; 612; 720; 788; 852; 990; 991; 1152; 1154; 1169; 1212; 1237; 1239; 1242; 1326; 1489; 1490; 1641; 1683; 1694; 1711; 1723; 1731; 1741; 1744; 1747; 1749; 1789; 1800; 1831; 1833; 1834; 1837; 1950; 1951; 1952; 1953; 1984; 1994; 1995; 2023; 2038; 2117; 2126; 2127; 2128; 2129; 2130; 2133; 2144; 2284; 2305; 2365; 2372; 2375; 2378; 2380; 2382; 2399; 2406; 2411; 2458; 2459; 2462; 2528; 2529; 2532; 2533; 2534; 2538; 2542; 2543; 2556; 2563; 2564; 2652; 2679; 2703; 2708; 2709; 2725; 2727; 2732; 2740; 2887; 2888; 2900; 2941; 2942; 2943; 2944; 3043; 3057; 3092; 3286; 3384; 3387; 3596; 3600; 3690; 3782; 3807; 3810; 3811; 3822; 3857; 3862; 3904; 3920; 3940; 3958; 4019; 4076; 4093; 4094; 4096; 4130; 4295; 4297; 4345; 4351; 4428; 4434; 4442; 4468; 4493; 4510; 4515; 4546; 4596; 4603; 4706; 4736; 4744; 4804; 4860; 4885; 4888; 4889; 4890; 4891; 4892; 4897; 4898; 4899; 4918; 4955; 4975; 4976; 4978; 5067; 5080; 5144; 5198; 5221; 5238; 5380; 5383; 5450; 5532; 5555 (see Table 1).

This combination permits correctly classifying 92.5% of the samples.

2.48. Identification of a Predictive Panel of 180 Markers (PANEL 46)

The inventors have demonstrated a combination of 180 markers, linked to an SVM algorithm, based on the sequences SEQ ID Nos: 1; 28; 73; 321; 323; 350; 352; 397; 417; 418; 513; 538; 612; 720; 788; 852; 990; 991; 1152; 1154; 1169; 1212; 1237; 1239; 1242; 1326; 1489; 1490; 1641; 1683; 1694; 1711; 1723; 1731; 1741; 1744; 1747; 1749; 1789; 1800; 1831; 1833; 1834; 1837; 1859; 1950; 1951; 1952; 1953; 1984; 1994; 1995; 2023; 2038; 2117; 2126; 2127; 2128; 2129; 2130; 2133; 2143; 2144; 2284; 2305; 2365; 2372; 2375; 2378; 2380; 2382; 2390; 2399; 2406; 2411; 2458; 2459; 2462; 2528; 2529; 2532; 2533; 2534; 2538; 2542; 2543; 2556; 2563; 2564; 2652; 2679; 2703; 2708; 2709; 2725; 2727; 2732; 2740; 2887; 2888; 2900; 2941; 2942; 2943; 2944; 3043; 3057; 3092; 3286; 3384; 3387; 3574; 3596; 3600; 3673; 3690; 3782; 3807; 3810; 3811; 3822; 3857; 3862; 3904; 3920; 3936; 3940; 3958; 4019; 4076; 4093; 4094; 4096; 4130; 4295; 4297; 4345; 4351; 4428; 4434; 4442; 4468; 4493; 4497; 4510; 4515; 4546; 4596; 4603; 4706; 4736; 4744; 4804; 4860; 4885; 4888; 4889; 4890; 4891; 4892; 4897; 4898; 4899; 4918; 4955; 4975; 4976; 4978; 4982; 5067; 5080; 5144; 5198; 5221; 5238; 5380; 5383; 5450; 5532; 5555 (see Table 1).

This combination permits correctly classifying 92.5% of the samples.

2.49. Identification of a Predictive Panel of 35 Markers (PANEL 55)

The inventors have demonstrated a combination of 35 markers, linked to an LDA algorithm, based on the sequences SEQ ID Nos: 60; 1154; 1169; 1242; 1641; 1699; 1744; 1834; 1837; 2023; 2078; 2126; 2127; 2128; 2130; 2142; 2145; 2328; 2375; 2411; 2458; 2529; 2533; 2543; 2725; 2727; 2943; 2944; 3044; 3057; 3822; 4351; 4523; 5233; 5238 (see Table 1).

The performances obtained are: a sensitivity of 100% and a specificity of 80%.

2.50. Identification of a Predictive Panel of 35 Markers (PANEL 56)

The inventors have demonstrated a combination of 35 markers, linked to an LDA algorithm, based on the sequences SEQ ID Nos: 60; 1152; 1154; 1169; 1242; 1744; 1834; 2023; 2038; 2078; 2126; 2127; 2128; 2142; 2145; 2300; 2328; 2380; 2411; 2458; 2528; 2529; 2533; 2543; 2725; 2727; 2943; 2944; 3044; 3057; 3904; 4351; 4975; 5233; 5238 (see Table 1).

The performances obtained are: a sensitivity of 100% and a specificity of 80%.

2.51. Identification of a Predictive Panel of 16 Markers (PANEL 57)

The inventors have demonstrated a combination of 16 markers, linked to an LDA algorithm, based on the sequences SEQ ID Nos: 60; 1169; 1744; 1834; 2078; 2127; 2145; 2529; 2533; 2543; 2725; 2727; 2943; 2944; 3057; 5238 (see Table 1).

The performances obtained are: a sensitivity of 100% and a specificity of 80%.

2.52. Identification of a Predictive Panel of 13 Markers (PANEL 58)

The inventors have demonstrated a combination of 13 markers, linked to an LDA algorithm, based on the sequences SEQ ID Nos: 1169; 1834; 2038; 2078; 2127; 2145; 2533; 2543; 2725; 2727; 2943; 2944; 5238 (see Table 1).

The performances obtained are: a sensitivity of 100% and a specificity of 80%.

2.53. Identification of a Predictive Panel of 28 Markers (PANEL 59)

The inventors have demonstrated a combination of 28 markers, linked to an LDA algorithm, based on the sequences SEQ ID Nos: 26; 58; 527; 529; 629; 1169; 1259; 1270; 1588; 1632; 1668; 1841; 1854; 1912; 2622; 2623; 3187; 3527; 3625; 3672; 3994; 4428; 4429; 4961; 4988; 5087; 5107; 5113 (see Table 1).

The performances obtained are: a sensitivity of 100% and a specificity of 85%.

2.54. Identification of a Predictive Panel of 14 Markers (PANEL 60)

The inventors have demonstrated a combination of 14 markers, linked to an LDA algorithm, based on the sequences SEQ ID Nos: 58; 529; 1169; 1259; 1270; 1588; 1632; 1668; 1841; 1854; 3672; 4429; 5087; 5107 (see Table 1).

The performances obtained are: a sensitivity of 100% and a specificity of 80%.

These last signatures confirm that analysis of the expression of 13, 14 or 16 markers can be a good tool to discriminate patients with Alzheimer's disease. The use of the restricted gene panel can be particularly suited to obtain a diagnosis and prognosis tool In fact, analysis of the expression of around ten markers does not require fabricating a high-density DNA chip, and can be directly implemented by other nucleic acid detection techniques, such as PCR, or by a low-density chip, which could provide a significant economic benefit and a simplified implementation.

EXAMPLE 3

Demonstrating Expression Profiles for Diagnosing Alzheimer's Disease from Blood Samples by Relative Measurements of Probe Pairs Another possible approach to searching for expression biomarkers comprises considering, instead of the absolute expression of one or more probe sets, rather the relative expression of different intra- or inter-gene probe sets. A gene produces several transcripts that participate in the complexity of its expression and its transcriptome. The probe sets on the GWSA microarray cover the transcriptome of each gene at strategic positions (specific splice variants and the exon-intron structure of the gene). Any gene can thus give rise to a probe set that can be up-regulated in a group of AD patients, while a second probe set derived from the same gene could be down-regulated. The relative expression of these two probe sets could then represent a statistically more significant diagnostic power than the individual expression of each probe set. A simplified analysis of the relative expression comprises identifying the pairs of probe sets for which the relative expression is reversed between the AD patient group and the control group. Thus, a score comprised between +1 and −1 can be associated with any pair of probe sets (x, y) based on the frequency of AD patients and controls for which x>y. For example, if x>y in 100% of AD patients and 0% of control individuals, then the score is 1−0=1. For example, if x>y in 80% of AD patients and 20% of control individuals, then the score is 0.8−0.2=0.6.

This analysis was done from all the genes present on the GWSA chip, by comparing all the probe sets within a same gene (filtered above the expression threshold of 3.8 (log 2)), from a set of 150 samples (80 AD and 70 controls) This analysis was done first from normalized expression values. More than 90% of the pairs have a score whose absolute value is less than 0.2, indicating an equilibrated and equivalent distribution of pairs (x, y) for which x>y in the AD group and the control group. The highest score obtained is 0.75 and concerns the pair SEQ ID NO: 2677 and 2678, coming from the ATPase, Na+/K+ transporting, alpha 1 gene (ATP1A1, Gene ID: 476). 2007 pairs of probe sets have a score whose absolute value is greater than or equal to 0.5. This is the TSP N group (scores in column I of Table 2). Such scores are significant, as the following analysis performed on the three genes shows: Presenilin 1 (PSEN1), CD45 (PTPRC) and Sortilin-1 (SORL1). The best scores obtained for these three genes are respectively: 0.55; 0.57 and 0.69. This analysis was repeated on 1000 cases by creating two random groups of 80 and 70 individuals for each case out of the 150 individuals. The best scores obtained randomly are then 0.40, 0.39 and 0.45, all three lower than the scores of 0.55; 0.57 and 0.69 obtained from the AD and control group. These results demonstrate that the best scores associated with the probe set pairs of these three genes are statistically significant for the two groups compared. The definition of a score threshold at 0.5 is therefore significant. This TSP N group is represented by the probe pairs of the following sets (a pair being represented by x_y):

SEQ ID NO : 1_3; 1_5; 1_10; 1_11; 1_12; 1_13; 1_14; 2_3; 3_4; 4_10; 7_9; 8_9; 28_29; 29_31; 33_34; 33_35; 33_36; 33_37; 44_49; 53_54; 56_57; 68_72; 69_71; 69_73; 69_76; 69_77; 69_78; 69_81; 69_82; 69_83; 70_83; 74_79; 74_85; 92_93; 95_96; 95_97; 106_107; 1_11_112; 122_124; 123_124; 129_130; 133_134; 135_139; 135_142; 135_144; 135_145; 135_146; 136_140; 136_141; 136_148; 136_149; 151_152; 154_155; 168_169; 168_170; 176_177; 182_183; 188_189; 192_193; 194_201; 194_207; 195_199; 195_203; 195_210; 196_212; 197_210; 198_202; 200_205; 202_204; 204_211; 205_208; 205_209; 206_212; 217_222; 218_220; 219_220; 220_221; 223_224; 224_225; 224_227; 224_228; 224_229; 224_230; 224_232; 224_233; 224_235; 224_236; 224_237; 224_238; 224_239; 224_240; 224_242; 224_243; 224_244; 224_246; 224_247; 224_248; 224_249; 224_250; 224_251; 224_252; 224_253; 224_254; 224_255; 224_257; 224_258; 224_259; 231_224; 264_268; 265_272; 266_269; 267_269; 269_273; 270_272; 270_274; 270_275; 270_276; 280_281; 282_283; 286_288; 287_288; 289_290; 291_292; 296_297; 298_299; 302_303; 303_304; 307_309; 314_315; 316_317; 318_319; 320_323; 326_327; 328_331; 329_332; 330_331; 331_333; 331_334; 331_335; 331_336; 344_346; 358_361; 363_364; 367_368; 367_369; 373_375; 380_381; 385_386; 386_391; 386_392; 387_389; 388_390; 393_395; 411_412; 414_418; 415_418; 429_430; 433_434; 434_435; 434_438; 436_437; 439_440; 463_464; 477_478; 477_479; 481_483; 484_485; 486_487; 486_488; 486_489; 486_490; 486_494; 486_495; 486_496; 486_497; 486_499; 491_493; 504_505; 507_508; 533_534; 544_548; 545_547; 546_552; 547_550; 547_553; 547_554; 549_551; 549_555; 557_558; 559_561; 560_566; 562_564; 573_574; 575_578; 576_578; 577_578; 579_580; 584_585; 586_587; 588_589; 610_611; 621_629; 622_629; 623_629; 624_629; 625_629; 626_629; 627_629; 628_629; 629_630; 629_632; 639_640; 642_643; 644_645; 649_651; 652_653; 670_672; 671_672; 674_675; 680_681; 682_683; 684_685; 700_702; 701_702; 703_704; 714_715; 717_718; 727_728; 733_735; 734_736; 740_743; 741_743; 742_746; 742_748; 743_745; 750_753; 755_756; 761_763; 761_764; 765_766; 765_767; 771_772; 771_773; 772_774; 773_774; 779_780; 791_795; 791_799; 791_801; 791_803; 791_814;

792_811; 793_807; 793_811; 794_811; 796_824; 797_809; 797_811; 804_811; 805_811; 806_825; 808_816; 808_823; 809_813; 810_816; 810_823; 811_813; 811_815; 811_818; 811_819; 811_820; 811_821; 811_822; 812_821; 827_829; 827_831; 828_830; 832_835; 833_837; 834_836; 835_838; 835_841; 836_841; 838_840; 847_849; 848_851; 849_850; 852_854; 852_855; 856_863; 856_866; 858_860; 862_865; 869_870; 873_882; 874_878; 874_882; 875_882; 876_882; 877_882; 879_882; 882_885; 883_884; 895_899; 895_900; 897_898; 898_904; 899_901; 907_909; 908_911; 919_920; 929_930; 929_931; 937_938; 941_942; 943_945; 943_946; 943_947; 944_947; 955_959; 960_961; 961_962; 961_963; 961_964; 961_965; 961_966; 961_968; 961_969; 970_971; 970_972; 974_975; 993_1011; 994_996; 994_1013; 995_997; 995_1001; 995_1002; 995_1003; 996_999; 998_1004; 998_1009; 998_1012; 1000_1009; 1005_1011; 1006_1011; 1007_1011; 1008_1011; 1009_1010; 1018_1021; 1022_1025; 1023_1024; 1024_1026; 1027_1028; 1034_1037; 1035_1036; 1038_1039; 1047_1048; 1053_1055; 1056_1059; 1056_1063; 1057_1060; 1058_1062; 1059_1061; 1064_1072; 1065_1067; 1066_1067; 1067_1068; 1067_1069; 1067_1071; 1068_1072; 1073_1074; 1081_1083; 1081_1084; 1081_1085; 1082_1086; 1087_1088; 1088_1089; 1088_1090; 1088_1091; 1088_1092; 1093_1094; 1097_1099; 1098_1101; 1098_1105; 1102_1117; 1103_1110; 1104_1114; 1107_1111; 1110_1118; 1110_1119; 1123_1133; 1124_1133; 1125_1126; 1125_1127; 1125_1128; 1125_1129; 1125_1130; 1125_1131; 1125_1132; 1134_1139; 1135_1138; 1136_1137; 1141_1144; 1174_1176; 1180_1183; 1181_1182; 1189_1190; 1189_1191; 1193_1194; 1193_1195; 1196_1197; 1196_1198; 1201_1202; 1208_1209; 1208_1210; 1208_1211; 1212_1213; 1219_1239; 1221_1237; 1222_1239; 1223_1242; 1224_1239; 1226_1244; 1226_1261; 1229_1231; 1229_1233; 1229_1247; 1231_1237; 1232_1239; 1233_1260; 1234_1242; 1234_1258; 1234_1259; 1236_1242; 1237_1243; 1237_1245; 1237_1249; 1237_1251; 1237_1263; 1237_1265; 1237_1267; 1238_1245; 1238_1249; 1238_1251; 1239_1244; 1239_1262; 1239_1266; 1239_1269; 1241_1256; 1242_1248; 1242_1250; 1242_1252; 1242_1255; 1245_1254; 1247_1253; 1247_1254; 1248_1258; 1248_1259; 1249_1254; 1271_1273; 1272_1274; 1275_1276; 1279_1280; 1281_1285; 1282_1284; 1283_1284; 1289_1292; 1290_1291; 1291_1293; 1295_1296; 1295_1297; 1299_1306; 1300_1303; 1301_1302; 1310_1311; 1310_1319; 1310_1320; 1310_1325; 1312_1321; 1312_1324; 1313_1326; 1314_1324; 1315_1328; 1317_1326; 1318_1319; 1323_1329; 1323_1330; 1326_1331; 1334_1336; 1335_1336; 1339_1340; 1341_1342; 1344_1345; 1350_1352; 1351_1353; 1359_1360; 1363_1364; 1367_1382; 1367_1383; 1368_1372; 1370_1385; 1371_1374; 1373_1389; 1375_1383; 1376_1388; 1380_1383; 1382_1392; 1383_1392; 1384_1390; 1384_1393; 1386_1387; 1386_1391; 1399_1402; 1400_1402; 1402_1403; 1402_1405; 1402_1407; 1402_1409; 1408_1412; 1418_1419; 1423_1427; 1424_1427; 1429_1430; 1429_1431; 1433_1435; 1434_1435; 1435_1438; 1436_1437; 1441_1442; 1443_1444; 1444_1446; 1444_1447; 1448_1450; 1448_1452; 1448_1453; 1448_1456; 1448_1457; 1448_1458; 1448_1459; 1448_1460; 1448_1461; 1448_1462; 1448_1463; 1448_1465; 1451_1471; 1453_1470; 1454_1467; 1466_1469; 1475_1476; 1476_1481; 1476_1482; 1477_1478; 1478_1479; 1478_1483; 1485_1489; 1486_1490; 1488_1490; 1488_1499; 1490_1492; 1490_1497; 1490_1500; 1501_1502; 1501_1503; 1501_1504; 1507_1508; 1511_1514; 1511_1519; 1536_1539; 1537_1539; 1538_1539; 1539_1540; 1539_1542; 1539_1544; 1541_1543; 1543_1545; 1546_1548; 1546_1550; 1547_1549; 1553_1554; 1553_1555; 1556_1558; 1557_1558; 1564_1565; 1567_1572; 1568_1569; 1570_1571; 1572_1573; 1572_1574; 1586_1587; 1593_1595; 1594_1596; 1602_1601; 1603_1605; 1604_1606; 1607_1608; 1610_1615; 1611_1614; 1612_1615; 1613_1614; 1620_1625; 1625_1626; 1628_1631; 1637_1638; 1641_1642; 1641_1644; 1641_1645; 1641_1646; 1655_1657; 1658_1659; 1658_1660; 1658_1661; 1658_1662; 1658_1663; 1658_1664; 1658_1665; 1658_1666; 1676_1677; 1678_1679; 1680_1681; 1682_1685; 1683_1684; 1683_1686; 1687_1688; 1694_1698; 1703_1704; 1704_1707; 1706_1708; 1711_1712; 1715_1716; 1726_1727; 1727_1728; 1732_1738; 1733_1745; 1735_1751; 1736_1745; 1738_1745; 1739_1745; 1745_1746; 1745_1750; 1749_1752; 1754_1755; 1757_1758; 1760_1761; 1768_1769; 1777_1781; 1778_1781; 1781_1783; 1795_1797; 1796_1797; 1803_1804; 1817_1818; 1817_1819; 1820_1821; 1835_1837; 1842_1843; 1848_1850; 1848_1852; 1864_1866; 1865_1866; 1866_1867; 1866_1868; 1866_1869; 1866_1871; 1866_1872; 1866_1873; 1866_1874; 1866_1875; 1866_1877; 1866_1878; 1866_1879; 1866_1880; 1866_1881; 1866_1882; 1866_1883; 1866_1884; 1866_1885; 1866_1886; 1866_1887; 1866_1888; 1866_1889; 1866_1891; 1866_1892; 1866_1893; 1866_1894; 1866_1895; 1866_1896; 1866_1897; 1866_1898; 1866_1899; 1866_1900; 1866_1901; 1866_1902; 1866_1903; 1866_1904; 1866_1905; 1866_1906; 1866_1907; 1866_1908; 1866_1909; 1870_1866; 1921_1922; 1921_1923; 1921_1924; 1922_1927; 1922_1928; 1922_1929; 1922_1930; 1925_1931; 1925_1932; 1936_1937; 1939_1941; 1939_1943; 1939_1944; 1939_1945; 1949_1954; 1957_1958; 1962_1963; 1965_1967; 1974_1975; 1988_1992; 1991_1993; 1997_1998; 2004_2006; 2013_2016; 2014_2016; 2015_2016; 2018_2019; 2026_2027; 2028_2029; 2029_2031; 2029_2034; 2030_2033; 2035_2036; 2043_2044; 2046_2048; 2051_2058; 2051_2059; 2052_2057; 2053_2059; 2055_2059; 2056_2059; 2065_2067; 2065_2079; 2066_2069; 2067_2076; 2068_2074; 2070_2078; 2071_2078; 2071_2082; 2072_2073; 2072_2081; 2073_2075; 2075_2081; 2076_2080; 2077_2083; 2077_2084; 2089_2090; 2101_2102; 2102_2105; 2103_2105; 2126_2131; 2138_2146; 2149_2152; 2150_2155; 2151_2154; 2151_2156; 2162_2163; 2169_2170; 2169_2171; 2169_2173; 2169_2174; 2178_2179; 2178_2181; 2183_2184; 2189_2191; 2191_2193; 2191_2194; 2191_2198; 2192_2197; 2192_2199; 2194_2196; 2196_2198; 2205_2206; 2208_2213; 2209_2210; 2211_2212; 2219_2226; 2220_2223; 2222_2226; 2223_2231; 2224_2226; 2225_2226; 2226_2227; 2226_2229; 2226_2230; 2226_2232; 2226_2233; 2226_2234; 2236_2237; 2236_2238; 2239_2240; 2244_2245; 2248_2262; 2251_2262; 2253_2262;

2259_2261; 2262_2265; 2273_2276; 2274_2276;
2275_2276; 2276_2277; 2282_2283; 2285_2297;
2286_2287; 2286_2292; 2286_2297; 2288_2299;
2289_2299; 2291_2299; 2293_2299; 2294_2298;
2295_2296; 2302_2303; 2334_2338; 2338_2339;
2342_2343; 2351_2355; 2351_2357; 2353_2356;
2363_2364; 2366_2385; 2370_2386; 2375_2388;
2403_2404; 2422_2424; 2424_2427; 2424_2428;
2425_2427; 2426_2428; 2429_2430; 2432_2433;
2432_2434; 2448_2449; 2452_2453; 2455_2458;
2458_2466; 2459_2463; 2462_2463; 2464_2467;
2464_2468; 2472_2473; 2477_2478; 2477_2479;
2480_2481; 2482_2483; 2484_2485; 2487_2488;
2491_2492; 2495_2500; 2496_2505; 2496_2507;
2497_2499; 2497_2504; 2497_2505; 2497_2506;
2497_2508; 2497_2510; 2497_2512; 2497_2516;
2498_2504; 2498_2505; 2498_2509; 2498_2510;
2498_2511; 2498_2513; 2498_2514; 2500_2508;
2501_2511; 2502_2509; 2502_2511; 2502_2513;
2503_2506; 2503_2508; 2522_2523; 2528_2535;
2529_2537; 2532_2535; 2540_2563; 2541_2570;
2541_2572; 2542_2547; 2542_2550; 2542_2567;
2542_2568; 2543_2567; 2544_2572; 2549_2544;
2549_2545; 2549_2561; 2549_2576; 2551_2575;
2552_2575; 2553_2557; 2554_2558; 2561_2572;
2561_2573; 2562_2571; 2563_2565; 2563_2566;
2563_2569; 2564_2567; 2564_2568; 2572_2574;
2580_2581; 2608_2609; 2614_2615; 2624_2631;
2625_2626; 2626_2629; 2627_2630; 2637_2639;
2640_2642; 2641_2642; 2644_2645; 2646_2647;
2649_2650; 2652_2653; 2652_2656; 2652_2657;
2654_2655; 2661_2670; 2662_2664; 2662_2671;
2663_2669; 2664_2673; 2665_2667; 2666_2669;
2668_2670; 2668_2671; 2670_2673; 2671_2672;
2677_2678; 2677_2682; 2677_2688; 2677_2689;
2677_2694; 2678_2686; 2678_2690; 2682_2685;
2682_2686; 2682_2690; 2683_2692; 2686_2688;
2686_2689; 2687_2688; 2688_2690; 2689_2690;
2693_2694; 2704_2705; 2706_2708; 2707_2711;
2708_2712; 2713_2714; 2716_2718; 2716_2726;
2718_2722; 2719_2727; 2720_2723; 2722_2723;
2730_2745; 2731_2732; 2732_2733; 2732_2734;
2732_2736; 2732_2737; 2732_2738; 2734_2744;
2746_2748; 2748_2750; 2748_2757; 2748_2758;
2748_2759; 2749_2751; 2751_2756; 2752_2755;
2753_2754; 2760_2761; 2767_2768; 2773_2774;
2777_2779; 2778_2779; 2778_2780; 2778_2781;
2784_2786; 2785_2786; 2792_2794; 2797_2810;
2798_2799; 2800_2807; 2800_2808; 2801_2810;
2802_2806; 2803_2805; 2812_2814; 2812_2815;
2819_2827; 2820_2822; 2821_2822; 2822_2829;
2826_2832; 2830_2832; 2833_2834; 2839_2840;
2840_2842; 2845_2847; 2848_2849; 2854_2857;
2854_2864; 2854_2867; 2855_2858; 2855_2859;
2855_2868; 2856_2861; 2860_2861; 2861_2865;
2861_2866; 2875_2876; 2875_2877; 2875_2881;
2875_2884; 2878_2880; 2878_2883; 2878_2885;
2880_2882; 2911_2912; 2918_2923; 2926_2927;
2928_2929; 2948_2949; 2952_2953; 2952_2954;
2955_2959; 2956_2961; 2962_2965; 2963_2964;
2967_2973; 2968_2971; 2969_2972; 2970_2972;
2975_2977; 2980_2981; 2983_2984; 2986_2987;
2988_2989; 2988_2990; 2988_2992; 3001_3003;
3001_3004; 3008_3009; 3010_3011; 3011_3013;
3012_3013; 3015_3023; 3016_3027; 3017_3018;
3017_3023; 3017_3025; 3017_3026; 3017_3029;
3018_3030; 3018_3032; 3020_3023; 3023_3022;
3023_3030; 3023_3031; 3023_3032; 3027_3034;
3047_3049; 3051_3052; 3054_3056; 3057_3058;
3062_3063; 3064_3065; 3071_3073; 3072_3073;
3077_3078; 3077_3084; 3078_3080; 3078_3082;
3079_3084; 3090_3092; 3091_3092; 3092_3093;
3092_3094; 3092_3095; 3092_3099; 3100_3101;
3111_3112; 3111_3114; 3111_3115; 3116_3117;
3119_3137; 3120_3122; 3121_3123; 3121_3144;
3122_3125; 3122_3131; 3122_3133; 3122_3138;
3122_3139; 3122_3146; 3122_3147; 3123_3135;
3123_3140; 3126_3128; 3126_3130; 3127_3144;
3129_3145; 3132_3149; 3136_3144; 3140_3144;
3141_3146; 3141_3147; 3151_3152; 3154_3155;
3162_3163; 3168_3169; 3168_3170; 3176_3181;
3177_3182; 3178_3180; 3180_3183; 3197_3198;
3198_3199; 3201_3202; 3203_3204; 3227_3230;
3228_3231; 3236_3238; 3236_3239; 3236_3240;
3237_3238; 3242_3248; 3243_3244; 3243_3245;
3243_3246; 3243_3247; 3247_3249; 3251_3254;
3251_3256; 3258_3259; 3261_3263; 3262_3265;
3269_3271; 3274_3275; 3283_3284; 3287_3293;
3288_3289; 3289_3292; 3290_3293; 3290_3294;
3299_3300; 3316_3318; 3317_3321; 3318_3319;
3328_3329; 3331_3332; 3333_3334; 3336_3337;
3339_3344; 3343_3348; 3351_3352; 3351_3353;
3354_3357; 3357_3364; 3359_3363; 3367_3368;
3368_3369; 3370_3371; 3382_3383; 3385_3396;
3387_3395; 3387_3396; 3388_3398; 3388_3399;
3388_3401; 3390_3391; 3390_3392; 3390_3400;
3391_3397; 3393_3396; 3394_3404; 3395_3404;
3395_3405; 3396_3403; 3396_3404; 3396_3405;
3397_3398; 3397_3399; 3406_3407; 3407_3408;
3414_3415; 3415_3416; 3418_3419; 3421_3422;
3423_3424; 3431_3436; 3432_3437; 3433_3441;
3434_3439; 3435_3436; 3438_3440; 3438_3441;
3444_3463; 3444_3471; 3445_3446; 3447_3454;
3447_3460; 3449_3473; 3451_3464; 3451_3467;
3451_3468; 3453_3467; 3454_3464; 3454_3470;
3455_3465; 3456_3465; 3456_3467; 3475_3477;
3475_3479; 3476_3477; 3477_3482; 3478_3481;
3483_3484; 3485_3486; 3487_3488; 3492_3493;
3493_3495; 3494_3496; 3498_3499; 3501_3503;
3501_3504; 3510_3511; 3511_3513; 3512_3513;
3513_3514; 3528_3529; 3543_3544; 3544_3545;
3546_3549; 3547_3548; 3554_3555; 3556_3557;
3560_3561; 3570_3571; 3584_3585; 3589_3591;
3591_3592; 3591_3593; 3591_3594; 3603_3604;
3605_3606; 3610_3611; 3610_3612; 3610_3614;
3610_3616; 3610_3618; 3610_3619; 3610_3621;
3611_3622; 3612_3613; 3613_3618; 3613_3620;
3617_3618; 3630_3635; 3631_3633; 3631_3643;
3632_3634; 3632_3637; 3632_3641; 3638_3642;
3644_3645; 3647_3648; 3651_3653; 3652_3653;
3653_3655; 3653_3656; 3653_3658; 3653_3659;
3653_3662; 3653_3664; 3653_3668; 3675_3676;
3677_3680; 3678_3695; 3679_3690; 3681_3682;
3682_3687; 3682_3693; 3682_3694; 3682_3697;
3683_3689; 3683_3691; 3683_3696; 3684_3693;
3700_3701; 3703_3704; 3710_3720; 3711_3719;
3712_3715; 3714_3718; 3722_3725; 3723_3724;
3724_3726; 3724_3727; 3724_3728; 3724_3729;
3730_3731; 3735_3736; 3737_3741; 3738_3741;
3739_3741; 3740_3741; 3740_3742; 3744_3750;
3746_3747; 3754_3756; 3755_3757; 3760_3763;
3764_3765; 3766_3767; 3767_3768; 3767_3770;
3780_3781; 3784_3785; 3787_3788; 3791_3792;
3794_3795; 3797_3798; 3800_3803; 3801_3802;

3817_3818; 3831_3832; 3833_3834; 3834_3836; 3834_3839; 3834_3840; 3835_3838; 3837_3839; 3850_3857; 3852_3859; 3854_3861; 3857_3858; 3857_3860; 3865_3866; 3868_3869; 3873_3875; 3874_3877; 3874_3878; 3874_3879; 3874_3880; 3874_3881; 3874_3882; 3874_3883; 3885_3886; 3885_3888; 3891_3892; 3893_3894; 3899_3900; 3904_3905; 3908_3909; 3909_3910; 3909_3911; 3914_3919; 3916_3917; 3920_3923; 3924_3928; 3925_3926; 3925_3927; 3945_3947; 3946_3948; 3946_3949; 3958_3959; 3970_3971; 3980_3981; 3981_3982; 3981_3983; 3985_3986; 3988_3989; 3997_3998; 4000_4002; 4016_4017; 4017_4020; 4018_4021; 4022_4027; 4023_4037; 4024_4027; 4025_4029; 4025_4030; 4027_4034; 4027_4035; 4027_4036; 4027_4038; 4042_4044; 4043_4044; 4044_4047; 4046_4048; 4049_4050; 4050_4052; 4055_4060; 4056_4057; 4056_4059; 4058_4059; 4061_4062; 4066_4091; 4067_4076; 4067_4096; 4068_4093; 4069_4096; 4071_4076; 4072_4096; 4073_4093; 4074_4096; 4075_4093; 4075_4096; 4076_4080; 4076_4081; 4076_4082; 4076_4083; 4076_4103; 4076_4106; 4077_4093; 4077_4096; 4079_4093; 4079_4094; 4080_4091; 4084_4096; 4085_4096; 4086_4096; 4087_4096; 4088_4096; 4089_4096; 4090_4096; 4093_4098; 4093_4105; 4093_4107; 4093_4108; 4093_4109; 4096_4099; 4096_4100; 4096_4102; 4096_4103; 4096_4104; 4096_4105; 4096_4107; 4096_4108; 4096_4109; 4113_4114; 4116_4117; 4125_4127; 4126_4128; 4127_4129; 4130_4131; 4133_4136; 4134_4140; 4134_4145; 4134_4146; 4135_4140; 4135_4142; 4135_4152; 4136_4139; 4137_4141; 4137_4151; 4140_4148; 4140_4153; 4142_4150; 4143_4149; 4147_4149; 4150_4152; 4155_4160; 4156_4157; 4156_4158; 4156_4159; 4161_4168; 4165_4167; 4166_4169; 4173_4179; 4174_4180; 4175_4176; 4176_4181; 4177_4180; 4186_4189; 4187_4188; 4190_4191; 4195_4197; 4196_4197; 4210_4211; 4211_4214; 4212_4213; 4217_4218; 4224_4225; 4225_4226; 4236_4248; 4237_4239; 4238_4249; 4240_4246; 4241_4247; 4241_4248; 4241_4249; 4242_4248; 4243_4248; 4245_4250; 4258_4259; 4261_4264; 4262_4261; 4267_4268; 4270_4273; 4271_4277; 4272_4275; 4275_4279; 4276_4279; 4283_4291; 4284_4285; 4287_4290; 4288_4290; 4294_4295; 4297_4302; 4297_4303; 4297_4304; 4297_4305; 4309_4313; 4310_4312; 4311_4315; 4312_4313; 4312_4314; 4315_4316; 4317_4322; 4318_4324; 4319_4323; 4321_4325; 4324_4325; 4326_4329; 4328_4333; 4328_4334; 4332_4335; 4353_4354; 4355_4356; 4361_4363; 4366_4367; 4366_4368; 4372_4373; 4374_4377; 4382_4383; 4383_4384; 4387_4390; 4387_4391; 4387_4392; 4387_4393; 4389_4392; 4392_4394; 4392_4395; 4396_4398; 4397_4398; 4401_4408; 4402_4403; 4402_4405; 4404_4407; 4404_4413; 4406_4408; 4408_4409; 4408_4410; 4408_4412; 4416_4417; 4417_4418; 4420_4421; 4422_4423; 4422_4424; 4436_4437; 4439_4442; 4440_4442; 4441_4442; 4442_4444; 4442_4445; 4442_4446; 4442_4447; 4442_4448; 4442_4449; 4442_4450; 4442_4451; 4442_4453; 4442_4454; 4442_4455; 4442_4456; 4442_4457; 4442_4458; 4442_4459; 4442_4460; 4442_4461; 4442_4463; 4464_4465; 4464_4466; 4465_4467; 4473_4474; 4476_4477; 4484_4487; 4493_4496; 4494_4496; 4498_4500; 4503_4504; 4510_4513; 4511_4527; 4512_4527; 4514_4519; 4517_4528; 4518_4526; 4519_4528; 4520_4527; 4522_4531; 4523_4527; 4523_4531; 4524_4527; 4533_4534; 4535_4537; 4538_4539; 4538_4540; 4538_4542; 4538_4544; 4538_4545; 4546_4557; 4561_4562; 4563_4564; 4563_4565; 4563_4566; 4563_4567; 4563_4568; 4563_4570; 4563_4571; 4563_4572; 4563_4573; 4569_4571; 4576_4577; 4578_4579; 4579_4580; 4585_4586; 4589_4590; 4598_4601; 4602_4607; 4603_4604; 4603_4605; 4603_4606; 4604_4607; 4607_4608; 4614_4615; 4625_4655; 4626_4629; 4627_4649; 4628_4639; 4629_4631; 4629_4634; 4629_4635; 4629_4638; 4629_4639; 4629_4640; 4629_4643; 4629_4644; 4629_4645; 4629_4648; 4629_4650; 4630_4654; 4631_4651; 4631_4654; 4631_4655; 4632_4652; 4635_4651; 4635_4654; 4635_4655; 4636_4654; 4636_4655; 4637_4654; 4637_4655; 4639_4651; 4640_4651; 4640_4654; 4640_4655; 4642_4654; 4645_4651; 4645_4655; 4646_4654; 4647_4654; 4650_4654; 4657_4667; 4668_4670; 4673_4674; 4680_4683; 4684_4687; 4689_4690; 4689_4696; 4691_4696; 4695_4697; 4699_4701; 4702_4703; 4704_4710; 4705_4710; 4706_4707; 4707_4708; 4719_4720; 4723_4733; 4724_4733; 4724_4735; 4724_4736; 4725_4733; 4726_4733; 4726_4736; 4727_4733; 4728_4733; 4728_4735; 4729_4731; 4730_4733; 4740_4749; 4740_4754; 4741_4752; 4741_4765; 4741_4769; 4742_4744; 4742_4765; 4742_4768; 4742_4771; 4744_4746; 4744_4747; 4744_4755; 4744_4757; 4744_4758; 4744_4762; 4744_4766; 4744_4772; 4744_4773; 4745_4764; 4746_4771; 4748_4765; 4749_4756; 4749_4759; 4749_4761; 4754_4759; 4754_4763; 4760_4767; 4775_4776; 4777_4778; 4785_4786; 4786_4787; 4786_4788; 4793_4795; 4793_4796; 4794_4795; 4800_4801; 4802_4803; 4814_4815; 4817_4818; 4819_4821; 4820_4822; 4823_4825; 4823_4829; 4834_4850; 4835_4839; 4836_4843; 4836_4846; 4836_4849; 4837_4844; 4838_4845; 4840_4846; 4841_4843; 4841_4846; 4841_4847; 4841_4849; 4842_4846; 4852_4854; 4855_4860; 4858_4860; 4864_4866; 4864_4871; 4877_4879; 4878_4881; 4880_4881; 4888_4894; 4889_4893; 4889_4894; 4890_4894; 4902_4903; 4905_4906; 4911_4913; 4912_4913; 4930_4931; 4939_4942; 4940_4941; 4945_4955; 4947_4951; 4950_4951; 4950_4956; 4971_4972; 4983_4984; 4989_4994; 4989_5000; 4990_4994; 4990_5000; 4990_5001; 4991_4994; 4991_5000; 4992_5006; 4992_5008; 4993_5001; 4995_5003; 4995_5007; 4995_5010; 4996_5009; 4997_5002; 5000_5002; 5000_5005; 5001_5008; 5013_5014; 5033_5034; 5035_5036; 5054_5055; 5054_5056; 5054_5058; 5062_5063; 5064_5067; 5067_5068; 5070_5080; 5071_5080; 5072_5080; 5074_5079; 5075_5080; 5077_5080; 5080_5081; 5080_5082; 5080_5083; 5085_5089; 5086_5087; 5087_5088; 5091_5096; 5091_5097; 5092_5095; 5093_5094; 5102_5103; 5105_5106; 5117_5118; 5120_5121; 5124_5126; 5127_5128; 5131_5132; 5142_5143; 5148_5151; 5149_5150; 5152_5153; 5168_5169; 5171_5172; 5178_5179; 5192_5197; 5193_5197; 5194_5197; 5207_5208; 5213_5221; 5215_5221; 5216_5221; 5217_5221; 5218_5229; 5220_5221; 5221_5222; 5221_5223; 5221_5224; 5221_5225; 5221_5226; 5221_5230; 5221_5232; 5227_5229; 5228_5234; 5235_5239;

5236_5239; 5239_5243; 5240_5247; 5242_5247; 5250_5251; 5253_5255; 5254_5256; 5258_5261; 5259_5260; 5262_5264; 5263_5264; 5266_5267; 5276_5285; 5277_5285; 5279_5285; 5280_5285; 5281_5285; 5283_5285; 5284_5287; 5285_5286; 5285_5287; 5291_5292; 5293_5294; 5293_5295; 5296_5297; 5296_5298; 5296_5299; 5296_5302; 5300_5301; 5308_5311; 5309_5311; 5309_5312; 5310_5311; 5314_5324; 5315_5316; 5315_5323; 5318_5320; 5319_5322; 5320_5321; 5320_5323; 5326_5327; 5339_5340; 5341_5344; 5342_5348; 5345_5347; 5346_5349; 5351_5352; 5351_5354; 5359_5360; 5364_5369; 5366_5367; 5367_5368; 5377_5379; 5378_5379; 5379_5382; 5380_5381; 5385_5386; 5385_5388; 5386_5387; 5389_5390; 5392_5394; 5392_5395; 5397_5398; 5398_5399; 5398_5400; 5398_5401; 5398_5402; 5398_5404; 5398_5405; 5398_5406; 5423_5424; 5430_5432; 5431_5433; 5437_5438; 5442_5444; 5445_5447; 5446_5449; 5448_5449; 5451_5452; 5451_5454; 5451_5455; 5451_5457; 5452_5459; 5452_5460; 5453_5458; 5454_5460; 5461_5464; 5462_5464; 5463_5464; 5471_5473; 5472_5474; 5476_5477; 5478_5480; 5478_5482; 5479_5487; 5481_5485; 5481_5486; 5481_5487; 5481_5488; 5483_5484; 5484_5489; 5491_5492; 5496_5497; 5501_5502; 5501_5503; 5501_5506; 5501_5509; 5504_5508; 5505_5507; 5507_5509; 5508_5510; 5511_5512; 5515_5519; 5.516_5519; 5517_5519; 5526_5527; 5532_5536; 5541_5542; 5543_5545; 5550_5551; 5551_5552; 5554_5556; 5555_5560; 5557_5558; 5558_5559; 5558_5563; 5567_5568; 5570_5573; 5571_5570; 5572_5574

The inventors then demonstrated that it is possible to define classification functions from such pairs of significant probe sets, as illustrated in the example below where a classification function is constructed from 51 probe set pairs identified for the three genes PSEN1, PTPRC and SORL1.

A score of 0 or +1 can then be associated with each probe set pair for each patient. A global score per patient is then obtained by adding the individual scores. Per individual, the minimum score is thus 0 and the maximum score is 51 (for these 51 pairs). The following rule can be applied: An individual will be classified as AD if his or her score is greater than 51/2=25.5 and an individual will be classified as control if his or her score is less than 51/2 =25.5. FIG. 3 indicates the scores obtained for the 80 AD and 70 controls. 83% of AD patients are properly classified and 93% of controls are properly classified.

Effective classification functions can thus be characterized from these significant probe pairs.

The advantage of an analysis dependent on the relative expression of probe sets is that this type of analysis should be insensitive or only slightly sensitive to the normalization process. It is thus possible to perform the same type of analysis from crude, non-normalized expression values. This analysis allows defining the TSP NN group represented by the following 1865 pair sequences according to scores above 0.5 (column H of Table 2):

SEQ ID Nos : 1_3; 1_9; 1_10; 1_11; 1_12; 1_13; 1_14; 3_4; 4_10; 7_9; 8_9; 23_24; 27_30; 32_33; 33_34; 33_35; 33_37; 44_49; 56_57; 64_65; 68_72; 69_73; 69_77; 69_78; 69_81; 69_82; 69_83; 70_83; 92_93; 95_96; 95_97; 106_107; 111_112; 122_124; 123_124; 129_130; 131_132; 135_139; 135_142; 135_144; 135_145; 135_147; 136_137; 136_138; 136_140; 136_141; 136_148; 151_152; 154_155; 158_159; 160_161; 161_162; 168_169; 168_170; 176_177; 185_186; 188_189; 194_198; 195_203; 195_210; 197_210; 200_205; 204_211; 205_208; 206_212; 214_215; 220_221; 223_224; 224_226; 224_227; 224_228; 224_230; 224_232; 224_233; 224_234; 224_235; 224_236; 224_237; 224_238; 224_239; 224_240; 224_241; 224_242; 224_243; 224_245; 224_246; 224_247; 224_248; 224_249; 224_250; 224_251; 224_252; 224_253; 224_254; 224_255; 224_256; 224_257; 224_258; 224_259; 231_224; 266_269; 267_269; 269_273; 270_272; 270_275; 279_281; 282_283; 287_288; 289_290; 296_297; 302_303; 303_305; 314_315; 318_319; 323_324; 326_327; 328_331; 329_332; 330_331; 331_333; 331_334; 331_335; 331_336; 344_346; 358_361; 359_360; 380_381; 383_384; 385_386; 386_391; 387_389; 393_395; 411_412; 415_418; 428_429; 429_430; 429_431; 433_434; 434_438; 447_453; 460_461; 463_464; 477_478; 477_479; 481_483; 484_485; 486_488; 486_489; 486_490; 486_492; 486_494; 486_495; 486_496; 486_497; 486_498; 486_500; 491_493; 525_526; 533_534; 545_547; 546_552; 547_553; 547_554; 549_551; 549_552; 562_563; 562_564; 575_578; 576_578; 577_578; 579_580; 584_585; 586_587; 588_589; 604_605; 610_611; 615_616; 621_629; 622_629; 623_629; 624_629; 627_629; 628_629; 629_630; 629_631; 629_632; 629_633; 639_640; 642_643; 644_645; 670_672; 674_675; 678_679; 680_681; 697_698; 699_702; 701_702; 717_718; 727_728; 729_730; 733_735; 742_744; 742_746; 742_747; 742_748; 742_749; 750_753; 755_756; 761_763; 765_767; 773_774; 779_781; 791_795; 791_798; 791_799; 791_800; 791_803; 791_814; 792_811; 793_811; 794_811; 796_800; 796_817; 796_824; 797_809; 797_811; 802_808; 804_811; 805_811; 806_825; 808_816; 808_823; 809_813; 809_820; 810_823; 811_813; 811_815; 811_818; 811_819; 811_820; 811_821; 811_822; 812_821; 827_829; 828_830; 832_835; 834_836; 835_837; 835_838; 835_841; 836_841; 838_840; 843_844; 848_851; 849_850; 852_853; 852_854; 856_863; 859_865; 861_864; 862_865; 869_870; 873_882; 874_882; 875_882; 876_882; 877_882; 879_882; 880_884; 881_884; 882_885; 886_889; 887_890; 888_890; 895_899; 895_900; 897_898; 899_901; 899_903; 900_902; 906_910; 908_911; 917_918; 937_938; 943_945; 943_946; 943_947; 944_947; 953_954; 960_961; 961_962; 961_964; 961_965; 961_967; 961_969; 970_971; 974_975; 993_1011; 994_1013; 995_1001; 995_1002; 995_1003; 996_999; 997_1000; 998_1009; 1000_1009; 1005_1011; 1006_1011; 1007_1011; 1008_1011; 1009_1010; 1018_1021; 1022_1025; 1035_1036; 1038_1039; 1047_1048; 1051_1052; 1054_1055; 1056_1063; 1057_1060; 1059_1061; 1065_1067; 1066_1067; 1067_1068; 1067_1069; 1067_1071; 1073_1074; 1081_1083; 1081_1084; 1087_1088; 1088_1089; 1088_1090; 1088_1092; 1097_1099; 1098_1101; 1098_1105; 1098_1106; 1098_1110; 1102_1117; 1103_1110; 1107_1111; 1107_1120; 1110_1118; 1110_1119; 1123_1133; 1124_1133; 1125_1126; 1125_1129; 1125_1130; 1125_1131; 1125_1132; 1135_1138; 1141_1144; 1143_1144; 1174_1177; 1180_1183; 1181_1182; 1182_1184; 1188_1192; 1189_1190; 1193_1194; 1196_1197; 1196_1198; 1199_1200; 1204_1205; 1208_1209; 1208_1210; 1212_1213; 1217_1237; 1219_

1239; 1221_1237; 1222_1239; 1223_1242; 1224_
1239; 1226_1244; 1226_1246; 1226_1261; 1227_
1245; 1228_1233; 1229_1233; 1229_1235; 1229_
1247; 1231_1237; 1233_1260; 1234_1242; 1234_
1259; 1236_1242; 1237_1243; 1237_1245; 1237_
1249; 1237_1251; 1237_1263; 1237_1264; 1237_
1265; 1237_1267; 1238_1245; 1238_1249; 1239_
1262; 1239_1266; 1239_1269; 1242_1248; 1242_
1250; 1242_1252; 1242_1255; 1245_1254; 1247_
1253; 1247_1254; 1248_1258; 1248_1259; 1249_
1254; 1275_1276; 1281_1285; 1282_1284; 1283_
1284; 1295_1296; 1295_1297; 1295_1298; 1299_
1305; 1299_1306; 1300_1303; 1301_1302; 1310_
1311; 1310_1316; 1310_1319; 1310_1320; 1310_
1325; 1312_1324; 1312_1327; 1313_1326; 1315_
1328; 1317_1326; 1318_1319; 1323_1329; 1323_
1330; 1326_1331; 1334_1337; 1335_1336; 1338_
1343; 1350_1352; 1351_1353; 1359_1360; 1368_
1372; 1369_1383; 1371_1374; 1376_1388; 1377_
1379; 1377_1381; 1378_1383; 1381_1391; 1383_
1392; 1384_1393; 1400_1402; 1402_1403; 1402_
1405; 1402_1407; 1402_1409; 1402_1410; 1402_
1411; 1403_1404; 1406_1408; 1408_1412; 1418_
1419; 1423_1427; 1424_1427; 1425_1427; 1426_
1427; 1429_1430; 1429_1431; 1433_1435; 1434_
1435; 1436_1437; 1443_1444; 1444_1446; 1448_
1450; 1448_1452; 1448_1453; 1448_1456; 1448_
1457; 1448_1458; 1448_1459; 1448_1460; 1448_
1464; 1448_1465; 1448_1468; 1449_1455; 1451_
1471; 1466_1469; 1475_1476; 1476_1480; 1476_
1481; 1476_1482; 1477_1478; 1478_1483; 1485_
1489; 1486_1490; 1488_1490; 1488_1499; 1490_
1492; 1490_1497; 1490_1500; 1501_1503; 1501_
1504; 1506_1505; 1511_1514; 1536_1539; 1537_
1539; 1538_1539; 1539_1544; 1541_1543; 1543_
1545; 1546_1548; 1546_1550; 1547_1549; 1553_
1554; 1553_1555; 1556_1558; 1557_1558; 1564_
1565; 1567_1572; 1568_1569; 1570_1571; 1570_
1574; 1572_1573; 1572_1574; 1586_1587; 1594_
1596; 1602_1601; 1603_1605; 1604_1606; 1610_
1615; 1611_1614; 1612_1615; 1613_1614; 1620_
1625; 1625_1626; 1636_1637; 1641_1642; 1641_
1643; 1641_1644; 1641_1645; 1641_1646; 1647_
1648; 1655_1657; 1656_1657; 1658_1659; 1658_
1660; 1658_1661; 1658_1662; 1658_1664; 1658_
1665; 1658_1666; 1680_1681; 1682_1685; 1683_
1684; 1683_1686; 1690_1693; 1703_1704; 1704_
1707; 1705_1707; 1706_1708; 1707_1708; 1711_
1712; 1715_1716; 1719_1720; 1726_1727; 1727_
1728; 1732_1738; 1733_1745; 1736_1745; 1737_
1741; 1738_1745; 1739_1745; 1745_1750; 1749_
1752; 1754_1755; 1754_1759; 1757_1758; 1760_
1761; 1768_1769; 1778_1781; 1780_1782; 1781_
1783; 1799_1800; 1803_1804; 1817_1818; 1817_
1819; 1822_1823; 1835_1837; 1842_1843; 1848_
1850; 1863_1866; 1865_1866; 1866_1867; 1866_
1868; 1866_1869; 1866_1872; 1866_1873; 1866_
1874; 1866_1875; 1866_1876; 1866_1877; 1866_
1878; 1866_1879; 1866_1880; 1866_1881; 1866_
1882; 1866_1883; 1866_1886; 1866_1887; 1866_
1888; 1866_1889; 1866_1890; 1866_1891; 1866_
1893; 1866_1895; 1866_1897; 1866_1900; 1866_
1902; 1866_1903; 1866_1904; 1866_1906; 1866_
1907; 1866_1908; 1866_1909; 1870_1866; 1921_
1922; 1921_1923; 1922_1927; 1922_1928; 1922_
1929; 1925_1932; 1925_1933; 1926_1934; 1936_
1937; 1939_1940; 1939_1941; 1939_1943; 1939_
1944; 1939_1945; 1949_1954; 1949_1955; 1957_
1958; 1957_1959; 1957_1960; 1965_1967; 1968_
1970; 1968_1973; 1974_1975; 1979_1980; 1981_
1982; 1988_1992; 1989_1990; 1991_1993; 1997_
1998; 2004_2005; 2013_2016; 2014_2016; 2018_
2019; 2026_2027; 2028_2029; 2029_2031; 2029_
2034; 2030_2032; 2030_2033; 2035_2036; 2035_
2037; 2039_2040; 2046_2048; 2051_2059; 2052_
2057; 2054_2058; 2055_2059; 2056_2059; 2065_
2067; 2065_2079; 2066_2069; 2067_2076; 2068_
2074; 2068_2077; 2070_2078; 2071_2082; 2072_
2073; 2072_2081; 2073_2075; 2075_2081; 2076_
2080; 2077_2083; 2077_2084; 2089_2090; 2091_
2092; 2094_2095; 2100_2104; 2101_2102; 2102_
2105; 2103_2105; 2138_2146; 2149_2152; 2149_
2153; 2150_2155; 2151_2155; 2151_2156; 2162_
2163; 2169_2171; 2169_2172; 2175_2176; 2178_
2179; 2178_2180; 2178_2181; 2183_2184; 2189_
2191; 2191_2193; 2191_2198; 2191_2200; 2192_
2199; 2196_2198; 2201_2202; 2205_2206; 2209_
2210; 2220_2223; 2221_2226; 2222_2226; 2224_
2226; 2226_2227; 2226_2228; 2226_2230; 2226_
2233; 2226_2234; 2236_2237; 2236_2238; 2239_
2240; 2244_2245; 2248_2262; 2251_2262; 2253_
2262; 2262_2265; 2273_2276; 2274_2276; 2275_
2276; 2282_2283; 2286_2287; 2286_2292; 2286_
2297; 2288_2299; 2289_2299; 2290_2299; 2291_
2299; 2291_2301; 2294_2298; 2295_2296; 2302_
2304; 2308_2309; 2335_2337; 2351_2355; 2351_
2357; 2353_2356; 2354_2359; 2363_2364; 2372_
2387; 2375_2388; 2403_2404; 2419_2420; 2422_
2424; 2423_2424; 2424_2427; 2424_2428; 2425_
2427; 2429_2430; 2431_2432; 2432_2433; 2432_
2434; 2437_2439; 2438_2440; 2455_2457; 2455_
2458; 2458_2466; 2459_2463; 2462_2463; 2464_
2467; 2470_2471; 2472_2473; 2472_2474; 2475_
2476; 2477_2478; 2477_2479; 2480_2481; 2482_
2483; 2487_2488; 2491_2492; 2496_2505; 2496_
2507; 2496_2509; 2497_2499; 2497_2504; 2497_
2505; 2497_2506; 2497_2508; 2497_2510; 2497_
2512; 2497_2516; 2498_2504; 2498_2505; 2498_
2509; 2498_2510; 2498_2511; 2498_2513; 2498_
2514; 2498_2515; 2501_2511; 2502_2509; 2502_
2511; 2502_2515; 2503_2508; 2525_2526; 2528_
2535; 2529_2537; 2532_2535; 2541_2570; 2541_
2572; 2542_2547; 2542_2550; 2542_2567; 2542_
2568; 2543_2567; 2544_2572; 2549_2544; 2549_
2545; 2549_2561; 2549_2576; 2551_2575; 2552_
2575; 2553_2557; 2554_2558; 2561_2572; 2561_
2573; 2562_2571; 2563_2566; 2563_2569; 2564_
2567; 2564_2568; 2572_2574; 2597_2598; 2608_
2609; 2609_2611; 2610_2611; 2614_2615; 2624_
2631; 2625_2626; 2626_2628; 2626_2629; 2627_
2630; 2634_2635; 2637_2639; 2640_2642; 2641_
2642; 2642_2643; 2644_2645; 2651_2655; 2652_
2653; 2652_2656; 2652_2657; 2654_2655; 2661_
2670; 2661_2671; 2662_2664; 2662_2671; 2663_
2669; 2664_2673; 2665_2667; 2666_2669; 2670_
2673; 2674_2675; 2677_2678; 2677_2688; 2677_
2689; 2677_2694; 2678_2686; 2678_2690; 2681_
2694; 2682_2685; 2682_2686; 2682_2687; 2682_
2690; 2683_2692; 2686_2688; 2686_2689; 2687_
2688; 2688_2690; 2689_2690; 2693_2694; 2704_
2705; 2706_2708; 2707_2711; 2715_2721; 2715_
2722; 2716_2718; 2716_2726; 2717_2726; 2718_
2722; 2719_2725; 2719_2727; 2722_2723; 2730_
2745; 2731_2732; 2732_2733; 2732_2734; 2732_

2735; 2732_2736; 2732_2737; 2732_2738; 2732_2739; 2746_2748; 2747_2748; 2748_2750; 2748_2757; 2748_2758; 2748_2759; 2749_2751; 2751_2756; 2753_2754; 2760_2761; 2764_2766; 2777_2779; 2778_2780; 2784_2786; 2785_2786; 2792_2794; 2797_2800; 2797_2810; 2798_2799; 2800_2807; 2800_2808; 2801_2810; 2802_2806; 2808_2810; 2812_2814; 2812_2815; 2819_2827; 2820_2822; 2821_2822; 2822_2829; 2826_2832; 2830_2832; 2836_2837; 2839_2840; 2840_2841; 2840_2842; 2846_2847; 2848_2849; 2854_2857; 2854_2864; 2854_2867; 2855_2858; 2855_2859; 2855_2861; 2856_2861; 2861_2865; 2875_2881; 2875_2884; 2878_2880; 2878_2883; 2878_2885; 2880_2882; 2911_2912; 2926_2927; 2928_2929; 2930_2931; 2948_2949; 2952_2953; 2952_2954; 2955_2959; 2955_2960; 2956_2961; 2957_2958; 2962_2965; 2963_2966; 2968_2971; 2969_2972; 2970_2972; 2974_2975; 2975_2977; 2995_2996; 2998_2999; 3001_3002; 3001_3003; 3006_3007; 3015_3023; 3016_3023; 3017_3018; 3017_3023; 3017_3026; 3018_3030; 3018_3032; 3019_3024; 3020_3023; 3021_3023; 3023_3022; 3023_3030; 3023_3032; 3023_3033; 3023_3034; 3027_3032; 3038_3039; 3039_3040; 3046_3048; 3047_3049; 3054_3056; 3057_3058; 3059_3060; 3062_3063; 3069_3070; 3077_3078; 3077_3083; 3077_3084; 3078_3080; 3078_3081; 3078_3082; 3079_3084; 3090_3092; 3091_3092; 3092_3094; 3092_3095; 3092_3096; 3092_3097; 3092_3098; 3100_3101; 3111_3112; 3111_3113; 3111_3114; 3111_3115; 3116_3117; 3120_3122; 3120_3142; 3121_3123; 3122_3125; 3122_3131; 3122_3133; 3122_3138; 3122_3139; 3122_3146; 3122_3147; 3123_3134; 3123_3135; 3123_3140; 3124_3143; 3124_3144; 3126_3130; 3127_3144; 3129_3145; 3132_3149; 3136_3144; 3136_3145; 3139_3142; 3141_3147; 3144_3148; 3150_3151; 3154_3155; 3174_3176; 3176_3181; 3177_3182; 3178_3180; 3179_3184; 3180_3183; 3198_3199; 3201_3202; 3209_3210; 3212_3214; 3227_3230; 3228_3231; 3229_3232; 3236_3238; 3236_3239; 3236_3240; 3236_3241; 3251_3256; 3253_3255; 3254_3255; 3257_3258; 3261_3263; 3264_3265; 3267_3271; 3269_3271; 3274_3275; 3287_3293; 3288_3289; 3290_3293; 3290_3294; 3290_3295; 3291_3293; 3316_3318; 3317_3321; 3318_3319; 3339_3344; 3342_3347; 3343_3348; 3351_3352; 3351_3353; 3354_3357; 3355_3363; 3357_3364; 3359_3363; 3367_3368; 3368_3369; 3382_3383; 3385_3396; 3386_3402; 3387_3395; 3387_3396; 3388_3398; 3388_3401; 3390_3391; 3390_3392; 3390_3400; 3391_3397; 3395_3405; 3396_3403; 3396_3404; 3396_3405; 3397_3399; 3406_3407; 3414_3415; 3418_3419; 3423_3424; 3425_3426; 3431_3436; 3433_3441; 3434_3439; 3435_3436; 3438_3440; 3444_3448; 3444_3465; 3444_3471; 3444_3472; 3445_3446; 3447_3454; 3447_3459; 3447_3460; 3449_3450; 3451_3472; 3454_3469; 3454_3470; 3456_3464; 3456_3465; 3457_3468; 3458_3466; 3458_3467; 3475_3477; 3475_3479; 3476_3477; 3478_3481; 3483_3484; 3492_3493; 3493_3495; 3494_3496; 3495_3497; 3498_3499; 3501_3504; 3511_3513; 3512_3513; 3513_3514; 3543_3544; 3544_3545; 3546_3549; 3550_3551; 3556_3557; 3568_3569; 3570_3571; 3584_3585; 3591_3592; 3591_3593; 3591_3594; 3605_3606; 3610_3611; 3610_3612; 3610_3614; 3610_3618; 3610_3619; 3610_3621; 3611_3622; 3613_3618; 3613_3619; 3613_3620; 3615_3618; 3630_3635; 3632_3634; 3632_3637; 3632_3641; 3633_3640; 3634_3636; 3638_3642; 3647_3648; 3651_3653; 3653_3654; 3653_3655; 3653_3656; 3653_3660; 3653_3661; 3653_3662; 3653_3663; 3653_3665; 3653_3666; 3653_3667; 3653_3669; 3677_3680; 3678_3695; 3679_3690; 3681_3682; 3682_3687; 3682_3693; 3682_3694; 3682_3697; 3683_3689; 3683_3696; 3684_3693; 3701_3702; 3710_3720; 3711_3719; 3716_3717; 3721_3724; 3723_3724; 3724_3726; 3724_3727; 3724_3728; 3724_3729; 3730_3731; 3735_3736; 3737_3741; 3738_3741; 3739_3741; 3740_3741; 3744_3745; 3744_3749; 3744_3750; 3746_3747; 3754_3756; 3755_3757; 3760_3763; 3764_3765; 3766_3767; 3767_3768; 3767_3769; 3767_3770; 3774_3775; 3779_3780; 3780_3781; 3784_3785; 3787_3788; 3800_3803; 3801_3802; 3817_3818; 3825_3827; 3831_3832; 3833_3834; 3834_3839; 3834_3840; 3837_3839; 3850_3857; 3852_3857; 3852_3859; 3857_3858; 3857_3860; 3865_3866; 3868_3869; 3873_3875; 3874_3876; 3874_3877; 3874_3881; 3874_3883; 3885_3887; 3891_3892; 3893_3894; 3901_3902; 3903_3904; 3904_3905; 3906_3907; 3908_3909; 3909_3910; 3909_3911; 3918_3922; 3920_3923; 3924_3928; 3925_3926; 3925_3927; 3941_3942; 3945_3947; 3946_3948; 3946_3949; 3980_3981; 3980_3984; 3985_3986; 3988_3989; 3997_3998; 3999_4003; 4000_4002; 4023_4037; 4024_4027; 4025_4029; 4026_4027; 4027_4033; 4027_4035; 4027_4036; 4028_4032; 4031_4036; 4041_4045; 4042_4044; 4043_4044; 4044_4047; 4046_4048; 4049_4050; 4050_4052; 4055_4060; 4056_4059; 4057_4058; 4061_4062; 4067_4076; 4067_4096; 4068_4093; 4069_4093; 4069_4096; 4071_4076; 4073_4093; 4075_4093; 4075_4096; 4076_4101; 4077_4093; 4077_4096; 4079_4093; 4079_4094; 4079_4096; 4085_4096; 4086_4096; 4087_4096; 4088_4096; 4089_4096; 4090_4096; 4093_4098; 4093_4105; 4093_4107; 4093_4108; 4093_4109; 4093_4110; 4096_4099; 4096_4100; 4096_4103; 4096_4104; 4096_4105; 4096_4107; 4096_4109; 4113_4114; 4116_4117; 4118_4120; 4122_4123; 4125_4127; 4127_4129; 4130_4131; 4132_4136; 4133_4136; 4134_4140; 4135_4138; 4135_4140; 4135_4142; 4135_4152; 4136_4139; 4136_4144; 4137_4141; 4137_4151; 4140_4148; 4140_4153; 4142_4150; 4143_4149; 4147_4149; 4150_4152; 4155_4160; 4156_4157; 4156_4158; 4156_4159; 4162_4163; 4165_4167; 4166_4169; 4175_4176; 4176_4181; 4177_4180; 4178_4180; 4190_4191; 4195_4197; 4196_4197; 4203_4204; 4205_4208; 4210_4211; 4211_4214; 4215_4216; 4217_4218; 4224_4225; 4236_4248; 4237_4239; 4238_4249; 4240_4246; 4241_4249; 4243_4248; 4244_4246; 4251_4252; 4253_4254; 4258_4259; 4261_4263; 4262_4261; 4270_4273; 4271_4277; 4272_4275; 4274_4278; 4283_4291; 4284_4285; 4286_4289; 4287_4290; 4288_4290; 4294_4295; 4297_4303; 4297_4305; 4301_4304; 4309_4313; 4310_4312; 4311_4315; 4312_4313; 4312_4314; 4315_4316; 4317_4322; 4318_4324; 4319_4320; 4319_4323; 4321_4325; 4324_4325; 4328_4333; 4328_4334; 4332_4335; 4338_4339; 4355_4356; 4360_4362; 4361_4363; 4366_4369; 4385_4392; 4387_4390; 4387_4391; 4387_4392;

4387_4393; 4396_4398; 4404_4407; 4404_4413; 4406_4408; 4408_4409; 4408_4411; 4408_4412; 4414_4415; 4416_4417; 4417_4418; 4420_4421; 4422_4424; 4436_4437; 4440_4442; 4441_4442; 4442_4443; 4442_4444; 4442_4446; 4442_4449; 4442_4450; 4442_4452; 4442_4453; 4442_4454; 4442_4455; 4442_4456; 4442_4457; 4442_4458; 4442_4459; 4442_4462; 4464_4465; 4464_4466; 4465_4467; 4473_4474; 4476_4477; 4477_4478; 4484_4487; 4485_4486; 4490_4491; 4493_4496; 4494_4496; 4498_4500; 4503_4504; 4510_4513; 4510_4530; 4511_4527; 4512_4527; 4514_4519; 4514_4521; 4516_4526; 4516_4529; 4520_4527; 4520_4531; 4523_4527; 4524_4527; 4533_4534; 4535_4536; 4535_4537; 4538_4539; 4538_4540; 4538_4543; 4538_4545; 4539_4541; 4550_4557; 4561_4562; 4563_4564; 4563_4565; 4563_4566; 4563_4567; 4563_4568; 4563_4570; 4563_4571; 4563_4572; 4563_4573; 4569_4571; 4576_4577; 4579_4580; 4585_4586; 4588_4589; 4589_4590; 4597_4600; 4598_4599; 4603_4604; 4603_4605; 4603_4606; 4604_4607; 4606_4607; 4607_4608; 4614_4615; 4614_4616; 4625_4629; 4625_4651; 4625_4655; 4626_4629; 4627_4649; 4629_4631; 4629_4634; 4629_4635; 4629_4638; 4629_4639; 4629_4640; 4629_4643; 4629_4644; 4629_4645; 4629_4648; 4629_4650; 4629_4653; 4630_4654; 4631_4651; 4631_4654; 4631_4655; 4632_4652; 4633_4652; 4635_4651; 4635_4654; 4635_4655; 4636_4654; 4636_4655; 4637_4651; 4637_4654; 4637_4655; 4639_4651; 4640_4651; 4640_4654; 4640_4655; 4641_4655; 4642_4654; 4645_4651; 4645_4655; 4647_4654; 4648_4654; 4657_4667; 4668_4670; 4669_4670; 4673_4674; 4681_4682; 4684_4685; 4684_4686; 4684_4687; 4689_4690; 4695_4697; 4702_4703; 4704_4710; 4705_4710; 4706_4707; 4707_4708; 4709_4710; 4719_4720; 4723_4733; 4724_4733; 4724_4735; 4724_4736; 4726_4733; 4726_4736; 4728_4733; 4729_4731; 4739_4763; 4740_4749; 4740_4754; 4741_4743; 4741_4753; 4741_4765; 4741_4769; 4742_4744; 4742_4765; 4742_4768; 4742_4770; 4744_4746; 4744_4747; 4744_4755; 4744_4757; 4744_4758; 4744_4762; 4744_4766; 4744_4772; 4745_4764; 4746_4771; 4749_4761; 4750_4768; 4751_4763; 4754_4759; 4760_4765; 4760_4767; 4768_4774; 4771_4772; 4775_4776; 4784_4786; 4785_4786; 4786_4787; 4786_4788; 4793_4795; 4793_4796; 4794_4795; 4814_4815; 4817_4818; 4819_4821; 4820_4822; 4830_4832; 4834_4850; 4836_4843; 4836_4848; 4838_4845; 4840_4846; 4841_4843; 4841_4846; 4841_4847; 4841_4849; 4842_4846; 4852_4853; 4852_4854; 4855_4860; 4858_4860; 4863_4870; 4864_4866; 4864_4871; 4877_4879; 4878_4881; 4880_4881; 4881_4882; 4888_4894; 4889_4893; 4889_4894; 4890_4894; 4902_4903; 4902_4904; 4911_4913; 4914_4915; 4916_4919; 4930_4931; 4936_4937; 4939_4942; 4940_4941; 4947_4951; 4950_4951; 4971_4972; 4983_4984; 4989_4994; 4989_5000; 4990_5000; 4990_5001; 4991_5000; 4992_5006; 4992_5008; 4993_5001; 4995_5003; 4995_5007; 4995_5010; 4996_5009; 5000_5002; 5000_5005; 5001_5008; 5013_5014; 5031_5032; 5033_5034; 5040_5042; 5054_5055; 5054_5056; 5054_5058; 5064_5067; 5067_5068; 5070_5080; 5071_5080; 5072_5080; 5073_5080; 5074_5079; 5075_5080; 5076_5078; 5077_5080; 5080_5081; 5080_5082; 5080_5083; 5086_5087; 5087_5088; 5091_5096; 5092_5095; 5093_5094; 5102_5103; 5105_5106; 5114_5115; 5127_5128; 5129_5130; 5149_5150; 5152_5153; 5176_5177; 5178_5179; 5192_5197; 5193_5197; 5194_5197; 5214_5221; 5215_5221; 5216_5221; 5217_5221; 5219_5221; 5220_5221; 5221_5222; 5221_5223; 5221_5224; 5221_5225; 5221_5230; 5221_5232; 5227_5229; 5235_5239; 5236_5237; 5236_5239; 5239_5243; 5240_5247; 5242_5247; 5246_5248; 5250_5251; 5252_5254; 5258_5261; 5259_5260; 5263_5264; 5275_5278; 5276_5285; 5277_5285; 5279_5282; 5279_5285; 5280_5285; 5281_5285; 5283_5285; 5284_5287; 5285_5286; 5285_5287; 5291_5292; 5293_5294; 5293_5295; 5296_5297; 5296_5302; 5300_5301; 5303_5304; 5306_5307; 5308_5311; 5309_5311; 5309_5312; 5310_5311; 5311_5313; 5315_5316; 5319_5322; 5319_5323; 5320_5321; 5320_5323; 5339_5340; 5345_5347; 5346_5349; 5351_5352; 5351_5354; 5356_5360; 5357_5358; 5359_5360; 5361_5362; 5364_5369; 5366_5367; 5367_5368; 5377_5379; 5378_5379; 5379_5382; 5385_5386; 5385_5388; 5386_5387; 5389_5390; 5392_5393; 5392_5394; 5392_5395; 5397_5398; 5398_5399; 5398_5400; 5398_5403; 5418_5420; 5422_5424; 5423_5424; 5424_5426; 5424_5427; 5431_5433; 5445_5447; 5446_5449; 5448_5449; 5451_5452; 5451_5454; 5451_5455; 5451_5457; 5452_5459; 5453_5458; 5454_5456; 5461_5464; 5462_5464; 5463_5464; 5471_5473; 5471_5475; 5476_5477; 5478_5480; 5478_5482; 5479_5487; 5481_5486; 5481_5487; 5481_5488; 5484_5489; 5490_5493; 5496_5497; 5501_5502; 5501_5503; 5501_5506; 5504_5508; 5508_5510; 5514_5519; 5515_5519; 5516_5519; 5517_5519; 5543_5545; 5544_5546; 5547_5548; 5550_5551; 5551_5552; 5554_5556; 5555_5560; 5557_5558; 5558_5559; 5558_5563; 5565_5566; 5567_5568; 5570_5573; 5571_5570; 5572_5574

78% of the pairs of this group are present in the TSP N group established from normalized values.

Finally, such an analysis is also possible by comparing probe sets coming from different genes. We performed this analysis from 1300 of the most significant probe sets resulting from ANOVA analysis. A threshold set at 0.6 allows characterizing 406 pairs forming the TSP 1300 SS group (column G of Table 2), associated with the following pair sequences:

SEQ ID NO: 118_5254; 153_2416; 153_2732; 153_4779; 184_4493; 293_1731; 301_2727; 306_455; 306_614; 306_770; 306_1422; 306_1585; 306_1694; 306_1971; 306_2343; 306_2732; 306_2913; 306_3000; 306_3957; 306_4076; 306_4091; 306_4096; 306_4097; 306_4194; 306_4550; 306_4620; 306_4779; 306_5201; 306_5206; 306_5254; 306_5419; 354_5555; 374_1767; 382_1641; 382_2017; 382_2188; 382_3043; 382_3533; 382_3576; 382_3724; 382_3855; 382_4093; 382_4094; 382_4552; 382_4905; 382_5067; 382_5198; 382_5257; 382_5386; 397_2023; 397_3685; 422_3043; 427_5467; 432_4093; 439_1767; 444_3590; 444_5555; 448_3590; 448_5555; 449_4963; 455_3211; 473_2725; 473_2727; 473_5238; 506_1641; 506_4093; 510_3043; 510_4905; 510_5257; 530_1767; 594_3043; 598_2023; 629_673; 648_1749; 648_4493; 650_5196; 664_759; 665_4493; 708_1242; 712_1641; 712_4096; 716_1239; 751_1834; 751_2128; 751_2144; 751_2543; 751_2725; 751_2727; 751_5238; 752_2727; 757_3250; 758_

2900; 758_3935; 758_5555; 842_3552; 846_1641; 846_4096; 892_1161; 892_5257; 893_2944; 921_3211; 973_1834; 973_2543; 973_2727; 981_1641; 981_4093; 992_1767; 1122_4093; 1142_1834; 1142_2543; 1142_2727; 1159_2943; 1170_2900; 1170_3540; 1170_5555; 1174_1270; 1174_3211; 1185_2023; 1185_3685; 1216_5221; 1237_2900; 1237_4220; 1237_5555; 1239_1767; 1239_5090; 1239_5549; 1240_2943; 1242_1860; 1242_2941; 1242_2944; 1242_3312; 1242_3537; 1242_3540; 1242_4716; 1258_2941; 1258_2944; 1259_2941; 1259_2944; 1287_1767; 1288_1971; 1422_1766; 1422_3211; 1489_2900; 1489_2941; 1489_3540; 1489_5555; 1534_3043; 1564_2462; 1591_2725; 1591_2727; 1629_4493; 1633_2401; 1641_2157; 1641_4875; 1641_4963; 1641_5173; 1654_3211; 1675_4811; 1694_1766; 1694_4383; 1694_4875; 1731_2900; 1731_5555; 1731_5561; 1744_2900; 1744_2941; 1744_3312; 1744_3540; 1744_3590; 1744_4714; 1744_5555; 1747_2900; 1747_2941; 1747_3312; 1747_3540; 1747_4220; 1747_4714; 1747_5555; 1749_3372; 1749_5090; 1749_5332; 1749_5555; 1766_2732; 1766_4096; 1767_2226; 1767_4469; 1767_4736; 1767_4925; 1767_4955; 1767_5196; 1767_5198; 1834_2073; 1834_3068; 1834_4560; 1834_5205; 1846_2941; 1849_3312; 1853_2941; 1853_2944; 1853_3540; 1859_2023; 1859_3685; 1860_1951; 1860_2406; 1860_2695; 1860_3222; 1911_2732; 1911_4076; 1911_4096; 1911_4779; 1911_5206; 1911_5419; 1920_3043; 1920_4905; 1920_5198; 1951_2943; 1951_2944; 1972_2049; 1972_3189; 1972_3211; 1987_3043; 2023_2889; 2023_3506; 2023_3979; 2023_4425; 2023_4872; 2049_2732; 2049_4091; 2049_5206; 2073_2128; 2073_2141; 2073_2143; 2073_2144; 2073_2312; 2073_2325; 2073_2332; 2073_2543; 2073_2679; 2073_2725; 2073_2727; 2073_5238; 2115_2943; 2128_2330; 2128_4587; 2139_2941; 2139_2944; 2143_2943; 2157_4093; 2157_4094; 2158_2329; 2186_4905; 2226_3272; 2226_3306; 2250_3590; 2250_5555; 2250_5561; 2255_3590; 2257_3590; 2261_3590; 2263_4714; 2310_2941; 2312_3538; 2313_2943; 2313_3538; 2324_2943; 2324_2944; 2326_2943; 2326_2944; 2329_4388; 2330_2725; 2330_2727; 2330_5238; 2332_3538; 2384_2943; 2384_2944; 2398_5555; 2401_3782; 2406_2943; 2406_2944; 2411_2900; 2411_2941; 2411_3312; 2411_3540; 2411_4220; 2411_4714; 2411_5555; 2412_2941; 2412_3537; 2412_3540; 2412_4220; 2416_3211; 2462_3067; 2543_4560; 2590_2943; 2590_2944; 2590_3538; 2593_2941; 2595_3043; 2595_4905; 2605_3043; 2607_2725; 2607_2727; 2678_3590; 2679_2943; 2679_3538; 2692_2900; 2692_2941; 2692_3540; 2695_2941; 2695_2944; 2695_3312; 2714_4383; 2714_4875; 2725_2943; 2725_3208; 2725_3538; 2725_4587; 2725_4715; 2727_3538; 2727_3816; 2727_4560; 2727_4587; 2732_3211; 2732_4508; 2769_4096; 2782_4096; 2787_3043; 2787_4094; 2787_4905; 2787_5257; 2870_3043; 2891_2943; 2900_4495; 2900_4592; 2900_5051; 2901_3043; 2941_3220; 2941_3531; 2941_4592; 2941_4660; 2941_5355; 2941_5529; 2943_3222; 2943_4235; 2943_5050; 2943_5238; 2944_3222; 2944_3320; 2944_3531; 2944_4502; 2944_5355; 2944_5529; 2983_4963; 3043_3327; 3043_3674; 3043_4231; 3043_4959; 3043_5328; 3189_5254; 3211_4076; 3211_4091; 3211_4097; 3211_4751; 3211_4779; 3211_5206; 3211_5419; 3312_4592; 3317_5555; 3372_4493; 3372_4736; 3417_4096; 3538_3575; 3538_5238; 3540_4592; 3575_4587; 3674_4905; 4093_4875; 4093_4963; 4093_5173; 4093_5435; 4094_4963; 4094_5328; 4096_4383; 4096_4717; 4096_4875; 4096_5173; 4096_5274; 4096_5436; 4185_4493; 4231_4905; 4256_5238; 4376_5221; 4398_4963; 4470_5555; 4493_4901; 4493_5090; 4493_5555; 4495_5555; 4508_4779; 4587_5238; 4592_4714; 4736_5090; 4736_5549; 4865_5555; 4905_4959; 4905 5328

EXAMPLE 4

Identification of New Isoforms of PTPRC, SORL1 and PSEN1

The analysis of the relative expressions of probe sets associated with the PTPRC, SORL1 and PSEN1 genes (see section 9) identified intron-exon or exon-intron junction probes revealing the potential presence of new isoforms. These isoforms are described below.

PTPRC: The sequence SEQ ID NO: 3679 corresponds to the junction between intron 5 and exon 6 of the PTPRC gene. The expression values associated with this probe suggest that a splicing event exists at the 5' end of exon 6. In order to characterize this event, RT-PCR tests were performed on pools of AD patients or controls by means of a primer situated in the 3' end of intron 5 combined with a primer corresponding to exons 2 or 4. Amplicons are visualized by electrophoresis (FIG. 4A). Sequencing these amplicons shows the use of a new alternative consensus acceptor site situated 37 nucleotides upstream from the usual site for exon 6. The messenger RNA including this event could encode a protein of 208 amino acids (the first 144 corresponding to the N-terminal part of CD45 (PTPRC). The other amplicons correspond to the same splicing event associated with deletions of exon 4 or exon 4 and exon 5. The RT-PCR tests suggest that this new splicing event is specifically down-regulated in the AD population. The sequence SEQ ID NO: 3698 corresponds to the extension of 37 nucleotides specific for this event. The sequence SEQ ID NO: 3699 corresponds to the new junction between exon 5 and the new 5'-extended exon 6.

SORL1: The sequence SEQ ID NO: 4027 corresponds to the junction between exon 41 and intron 41 of the SORL1 gene. The expression values associated with this probe suggest that a splicing event exists at the 3' end of exon 41. In order to characterize this event, RT-PCR tests were performed on pools of AD patients or controls by means of a primer situated in the 5' end of intron 41 combined with a primer corresponding to exon 42. Amplicons are visualized by electrophoresis (FIG. 4B). Sequencing these amplicons shows the use of a new alternative consensus donor site situated 28 nucleotides downstream from the usual site for exon 41. A STOP codon is situated in this extension, suggesting that an associated messenger RNA would code for a truncated protein of 1870 amino acids not containing the transmembrane domain and the cytoplasmic tail. The sequence SEQ ID NO: 4039 corresponds to the extension of 28 nucleotides specific for this event. The sequence SEQ ID NO: 4040 corresponds to the new junction between new 3'-extended exon 41 and exon 42.

PSEN1: RT-PCR tests were performed on pools of AD patients or controls by means of a primer situated in a known alternative exon situated between exon 3 and 4 of PSEN1 (represented by EST AK122722.1), combined with a primer corresponding to exon 4. Amplicons are visualized by electrophoresis (Figure C). Sequencing these amplicons shows the use of a new alternative donor site located in the alternative exon 935 nucleotides upstream of the usual site for this alternative exon (position 72704987-88 of chromosome 14). The RT-PCR tests suggest that this new splicing event is specifically expressed in the AD population. The sequence SEQ ID NO: 3515 corresponds to the truncated alternative exon. The sequence SEQ ID NO: 3516 corresponds to the new junction between the new truncated alternative exon and exon 4.

EXAMPLE 5

Discrimination Between AD Patients, MCI Patients and Controls

Groups of probes were selected from among SEQ ID NO: 1-5578, which allow discriminating between patients with AD and control subjects, or between MCI patients and control subjects or between MCI subjects and AD patients.

The possibility of distinguishing MCI and AD patients is particularly important. In fact, 30-40% of subjects with MCI will progress to AD. The possibility of identifying these subjects from the MCI stage allows initiating effective treatment protocols for AD without waiting for the disease to progress.

The RNA of 9 patients with MCI, 11 patients with AD and 11 control subjects was extracted from venous blood, reverse-transcribed and labeled with biotin, and then hybridized on GWSA arrays. These arrays were next washed, visualized, and then scanned (Affymetrix scanner). The .CEL files were then imported into Partek statistical analysis software. All these steps were performed as described previously (see pages 28 to 32).

After normalization of the data, 5562 groups of probes from among the 5578 were filtered from the list of 1,455,615 of groups of probes composing the file. The corresponding graphs are given in FIG. 5.

A 1-way ANOVA test then allows identifying the statistically-significant groups of probes for the AD vs. MCI, AD vs. C and C vs. MCI conditions. Three files were then generated from the ANOVA test results, containing the 84, 366 and 969 first statistically-significant sets of probe groups for the AD vs. MCI, AD vs. C and MCI vs. C conditions, respectively. Groups of probes specific for the AD vs. MCI, AD vs. C and MCI vs. C conditions were then identified; these data permitted generating the Venn diagram. The groups of probes specific for each of these conditions are particularly pertinent to discriminate these different clinical statuses of the patients.

5.1. Sub-Sets of Probe Groups Specific for AD Vs. MCI.

| p-value cut-off | Anova test | AD vs. MCI specific probe sets |
| --- | --- | --- |
| 0.01 | 84 | 27 |
| 0.001 | 10 | 6 |

The names of the groups of probe sub-sets 6PS and 27PS are given in the table below.

| Set 1: 6 PS AD vs. MCI | SEQ ID | Set 2: 27 PS AD vs. MCI | SEQ ID |
| --- | --- | --- | --- |
| 399.009.1-B | 2363 | 1019.005.1-T | 53 |
| 399.010.1-B | 2364 | 151888.002.1-B | 613 |
| 9467.009.1-E | 5307 | 1729.004.4-T | 697 |
| 9730.027.1-T | 5426 | 1803.025.1-B | 709 |
| 6934.032.1-B | 4218 | 23161.034.1-T | 1200 |
| 8603.000.5-X | 5063 | 23178.025.1-B | 1205 |
|  |  | 23312.005.1-F | 1339 |
|  |  | 284701.000.14-X | 1846 |
|  |  | 3486.024.1-C | 2157 |
|  |  | 3837.009.1-T | 2289 |
|  |  | 399.009.1-B | 2363 |
|  |  | 4054.000.26-Z | 2429 |
|  |  | 442065.001.1-T | 2600 |
|  |  | 4670.020.1-B | 2639 |
|  |  | 4678.001.3-B | 2642 |
|  |  | 4820.026.1-B | 2712 |
|  |  | 56261.011.1-B | 3503 |
|  |  | 57680.013.1-B | 3636 |
|  |  | 57680.028.1-B | 3641 |
|  |  | 7919.040.1-B | 4529 |
|  |  | 80024.005.1-T | 4671 |
|  |  | 8556.016.1-T | 5055 |
|  |  | 8603.000.5-X | 5063 |
|  |  | 9282.000.20-X | 5219 |
|  |  | 9467.009.1-E | 5307 |
|  |  | 9611.052.1-F | 5354 |
|  |  | 9730.027.1-T | 5426 |

Set 1 thus contains:

from 1 to 3 probes, overlapping or not, each comprising all or part of SEQ ID NO: 2363 or its complementary sequence;

from 1 to 3 probes, overlapping or not, each comprising all or part of SEQ ID NO: 2364 or its complementary sequence;

from 1 to 3 probes, overlapping or not, each comprising all or part of SEQ ID NO: 5307 or its complementary sequence;

from 1 to 3 probes, overlapping or not, each comprising all or part of SEQ ID NO: 5426 or its complementary sequence;

from 1 to 3 probes, overlapping or not, each comprising all or part of SEQ ID NO: 4218 or its complementary sequence; and from 1 to 3 probes, overlapping or not, each comprising all or part of SEQ ID NO: 5063 or its complementary sequence.

In a similar manner, set 2 contains 1-3 probes comprising all or part of each sequence identified above or its complementary strand.

In one specific example, set 1 and set 2 respectively contain the probes identified in Table 3.

The signal intensity ratio after subtracting background noise between the patient groups for each probe group is given below.

|  | Variation factor (AD vs. MCI) |
| --- | --- |
| Set 1 |  |
| 9730.027.1-T | 1.65331 |
| 399.009.1-B | −1.92241 |
| 399.010.1-B | −1.95279 |
| 9467.009.1-E | 1.46337 |
| 8603.000.5-X | 1.76215 |
| 6934.032.1-B | 2.01881 |

-continued

| | Variation factor (AD vs. MCI) |
|---|---|
| Set 2 | |
| 9730.027.1-T | 1.65331 |
| 399.009.1-B | −1.92241 |
| 9467.009.1-E | 1.46337 |
| 8603.000.5-X | 1.76215 |
| 56261.011.1-B | −1.47064 |
| 442065.001.1-T | 1.31817 |
| 9611.052.1-F | 1.55709 |
| 80024.005.1-T | −1.3923 |
| 23161.034.1-T | −1.73865 |
| 57680.013.1-B | 1.36043 |
| 8556.016.1-T | −1.414 |
| 4054.000.26-Z | 1.36387 |
| 23312.005.1-F | 1.4399 |
| 1019.005.1-T | −1.39817 |
| 151888.002.1-B | −1.8663 |
| 284701.000.14-X | −1.27164 |
| 1803.025.1-B | −1.50387 |
| 7919.040.1-B | −1.32556 |
| 4820.026.1-B | −1.44063 |
| 4678.001.3-B | −2.01683 |
| 23178.025.1-B | −2.34804 |
| 57680.028.1-B | 1.3464 |
| 4670.020.1-B | 1.76039 |
| 1729.004.4-T | 1.56877 |
| 3486.024.1-C | −1.30762 |
| 9282.000.20-X | 1.27867 |
| 3837.009.1-T | 1.2558 |

5.2. Sub-Sets of Probe Groups Specific for AD Vs. Controls.

| p-value cut-off | Anova test | AD vs. C specific probe sets |
|---|---|---|
| 0.01 | 366 | 75 |
| 0.001 | 54 | 18 |

The names of the probes of sub-set 18 PS are given in the table below.

| Set 3: 18 PS ADvsC | SEQ ID |
|---|---|
| 55652.007.1-D | 3325 |
| 140564.002.2-B | 568 |
| 10250.000.13-X | 67 |
| 55833.001.2-B | 3408 |
| 402483.005.1-B | 2406 |
| 55700.021.1-T | 3337 |
| 55636.003.1-T | 3323 |
| 2690.003.1-B | 1724 |
| 143.000.1-X | 573 |
| 54882.014.1-B | 3180 |
| 6813.005.1-T | 4178 |
| 23067.007.1-T | 1096 |
| 5527.004.1-F | 3288 |
| 9883.024.1-T | 5523 |
| 441124.002.1-T | 2590 |
| 79623.000.12-Y | 4558 |
| 5930.016.1-F | 3757 |
| 808.038.1-C | 4735 |

Set 3 thus contains:
from 1 to 3 probes, overlapping or not, each comprising all or part of SEQ ID NO: 3325 or its complementary sequence;
from 1 to 3 probes, overlapping or not, each comprising all or part of SEQ ID NO: 568 or its complementary sequence;
from 1 to 3 probes, overlapping or not, each comprising all or part of SEQ ID NO: 67 or its complementary sequence;
from 1 to 3 probes, overlapping or not, each comprising all or part of SEQ ID NO: 3408 or its complementary sequence;
from 1 to 3 probes, overlapping or not, each comprising all or part of SEQ ID NO: 2406 or its complementary sequence;
from 1 to 3 probes, overlapping or not, each comprising all or part of SEQ ID NO: 3337 or its complementary sequence;
from 1 to 3 probes, overlapping or not, each comprising all or part of SEQ ID NO: 3323 or its complementary sequence;
from 1 to 3 probes, overlapping or not, each comprising all or part of SEQ ID NO: 1724 or its complementary sequence;
from 1 to 3 probes, overlapping or not, each comprising all or part of SEQ ID NO: 573 or its complementary sequence;
from 1 to 3 probes, overlapping or not, each comprising all or part of SEQ ID NO: 3180 or its complementary sequence;
from 1 to 3 probes, overlapping or not, each comprising all or part of SEQ ID NO: 4178 or its complementary sequence;
from 1 to 3 probes, overlapping or not, each comprising all or part of SEQ ID NO: 1096 or its complementary sequence;
from 1 to 3 probes, overlapping or not, each comprising all or part of SEQ ID NO: 3288 or its complementary sequence;
from 1 to 3 probes, overlapping or not, each comprising all or part of SEQ ID NO: 5523 or its complementary sequence;
from 1 to 3 probes, overlapping or not, each comprising all or part of SEQ ID NO: 2590 or its complementary sequence;
from 1 to 3 probes, overlapping or not, each comprising all or part of SEQ ID NO: 4558 or its complementary sequence;
from 1 to 3 probes, overlapping or not, each comprising all or part of SEQ ID NO: 3757 or its complementary sequence; and
from 1 to 3 probes, overlapping or not, each comprising all or part of SEQ ID NO: 4735 or its complementary sequence.

In one specific example, set 3 contains the probe groups identified in Table 3.

The signal intensity ratio after subtracting background noise between the patient groups for each probe group is given below.

| Set 3 | Variation factor (AD vs. C) |
|---|---|
| 55652.007.1-D | −1.17521 |
| 143.000.1-X | 2.06971 |
| 55833.001.2-B | −1.75477 |
| 6813.005.1-T | −1.46021 |
| 23067.007.1-T | −1.92904 |
| 441124.002.1-T | −1.28295 |
| 402483.005.1-B | −1.2913 |
| 9883.024.1-T | −1.48769 |
| 55700.021.1-T | −1.51693 |

-continued

| Set 3 | Variation factor (AD vs. C) |
|---|---|
| 10250.000.13-X | −1.93485 |
| 79623.000.12-Y | −1.49027 |
| 140564.002.2-B | −1.7224 |
| 5930.016.1-F | 1.53811 |
| 55636.003.1-T | −1.54333 |
| 5527.004.1-F | 1.47689 |
| 54882.014.1-B | −1.33383 |
| 808.038.1-C | −1.62719 |
| 2690.003.1-B | −1.0767 |

5.3. Sub-Sets of Probe Groups Specific for MCI Vs. Controls.

| p-value cut-off | Anova test | MCI vs. C specific probe sets |
|---|---|---|
| 0.01 | 969 | 635 |
| 0.001 | 413 | 373 |
| 0.0001 | 149 | |
| 0.0000 | 133 | |

The names of the probes of sub-set 33PS are given in the table below.

| Set 4: 33PS | SEQ ID |
|---|---|
| 10163.000.7-X | 42 |
| 10163.008.1-T | 45 |
| 10250.022.1-T | 79 |
| 10847.027.1-B | 275 |
| 11100.032.1-D | 349 |
| 2035.016.1-B | 830 |
| 2039.032.1-F | 841 |
| 2186.001.2-F | 894 |
| 2186.009.1-T | 895 |
| 2186.036.1-F | 902 |
| 23039.000.5-X | 1043 |
| 23327.025.4-B | 1356 |
| 23476.017.1-T | 1445 |
| 26057.008.1-B | 1668 |
| 27102.014.1-T | 1782 |
| 27350.004.1-B | 1800 |
| 283846.001.1-B | 1833 |
| 440345.006.14-B | 2542 |
| 4784.014.1-T | 2698 |
| 54856.007.1-F | 3156 |
| 54856.029.1-T | 3158 |
| 54856.033.1-F | 3160 |
| 55249.001.3-T | 3278 |
| 57610.000.6-X | 3606 |
| 6229.003.1-C | 3826 |
| 65125.000.20-X | 3967 |
| 65125.010.1-F | 3972 |
| 65125.025.1-T | 3976 |
| 81608.009.1-F | 4810 |
| 8289.000.2-X | 4864 |
| 8289.004.1-T | 4865 |
| 8289.008.1-B | 4867 |
| 8289.009.1-F | 4869 |

Set 4 thus contains, for each identified sequence, 1 to 3 probes, overlapping or not, each comprising all or part of the sequence or its complementary sequence.

Distribution studies are shown in FIG. 6. They particularly show that set 1 composed of 6 probe groups (6 PS) such as defined above allows discriminating MCI and AD patients (FIG. 6B). They also show that all the 18 probe groups such as defined above can discriminate AD patients and controls, i.e., can identify those who have AD in a population of subjects (FIG. 6A).

EXAMPLE 6

Detection Protocol

The steps for the diagnostic test are the following:
The sample is prepared from an RNA extraction step from blood samples collected in Paxgene blood sample tubes. These tubes contain an additive that stabilizes the transcription profile for genes in vivo by reducing RNA degradation in vitro and by minimizing gene induction. When they are used with a Paxgene™ Blood RNA Kit, the samples taken allow detection and exact quantification of the gene transcription level. After extraction, a qualitative and quantitative RNA control step is performed.

The RNA is retrotranscribed, linearly amplified and then fragmented, labeled with biotin and finally hybridized on biochips containing the probes of the invention. The arrays are then washed and the hybridization is visualized and scanned to measure the hybridization level on each probe. The hybridization results are then imported into Partek analysis software.

The application of the signature gives a binary response that allows placing the patient tested in the AD or control category.

TABLE 3

| Collection of probe sets | Reference sequence (target sequence (SEQ ID)) | Specific probe (SEQ ID) |
|---|---|---|
| Set 3 | 67 | 5770 |
| | 67 | 5771 |
| | 67 | 5772 |
| | 568 | 7210 |
| | 568 | 7211 |
| | 568 | 7212 |
| | 573 | 7225 |
| | 573 | 7226 |
| | 573 | 7227 |
| | 1096 | 8726 |
| | 1096 | 8727 |
| | 1096 | 8728 |
| | 1724 | 10549 |
| | 1724 | 10550 |
| | 1724 | 10551 |
| | 2406 | 12505 |
| | 2406 | 12506 |
| | 2406 | 12507 |
| | 2590 | 13021 |
| | 2590 | 13022 |
| | 2590 | 13023 |
| | 3180 | 14704 |
| | 3180 | 14705 |
| | 3180 | 14706 |
| | 3288 | 15011 |
| | 3288 | 15012 |
| | 3288 | 15013 |
| | 3323 | 15113 |
| | 3323 | 15114 |
| | 3323 | 15115 |
| | 3325 | 15119 |
| | 3325 | 15120 |
| | 3325 | 15121 |
| | 3337 | 15153 |
| | 3337 | 15154 |
| | 3337 | 15155 |
| | 3408 | 15355 |
| | 3408 | 15356 |
| | 3408 | 15357 |
| | 3757 | 16359 |

TABLE 3-continued

| Collection of probe sets | Reference sequence (target sequence (SEQ ID)) | Specific probe (SEQ ID) |
|---|---|---|
| | 3757 | 16360 |
| | 3757 | 16361 |
| | 4178 | 17560 |
| | 4178 | 17561 |
| | 4178 | 17562 |
| | 4558 | 18636 |
| | 4558 | 18637 |
| | 4558 | 18638 |
| | 4735 | 19146 |
| | 4735 | 19147 |
| | 4735 | 19148 |
| | 5523 | 21401 |
| | 5523 | 21402 |
| | 5523 | 21403 |
| Set 2 | 53 | 5728 |
| | 53 | 5729 |
| | 53 | 5730 |
| | 613 | 7337 |
| | 613 | 7338 |
| | 613 | 7339 |
| | 697 | 7571 |
| | 697 | 7572 |
| | 697 | 7573 |
| | 709 | 7606 |
| | 709 | 7607 |
| | 1200 | 9033 |
| | 1200 | 9034 |
| | 1200 | 9035 |
| | 1205 | 9046 |
| | 1205 | 9047 |
| | 1205 | 9048 |
| | 1339 | 9433 |
| | 1339 | 9434 |
| | 1339 | 9435 |
| | 1846 | 10897 |
| | 1846 | 10898 |
| | 1846 | 10899 |
| | 2157 | 11798 |
| | 2157 | 11799 |
| | 2157 | 11800 |
| | 2289 | 12184 |
| | 2289 | 12185 |
| | 2289 | 12186 |
| | 2429 | 12573 |
| | 2429 | 12574 |
| | 2429 | 12575 |
| | 2600 | 13049 |
| | 2600 | 13050 |
| | 2600 | 13051 |
| | 2639 | 13160 |
| | 2642 | 13167 |
| | 2712 | 13369 |
| | 2712 | 13370 |
| | 2712 | 13371 |
| | 3503 | 15630 |
| | 3503 | 15631 |
| | 3636 | 16007 |
| | 3636 | 16008 |
| | 3636 | 16009 |
| | 3641 | 16022 |
| | 3641 | 16023 |
| | 3641 | 16024 |
| | 4529 | 18553 |
| | 4529 | 18554 |
| | 4671 | 18961 |
| | 4671 | 18962 |
| | 4671 | 18963 |
| | 5055 | 20051 |
| | 5055 | 20052 |
| | 5055 | 20053 |
| | 5219 | 20522 |
| | 5219 | 20523 |
| | 5219 | 20524 |
| | 5354 | 20912 |
| | 5354 | 20913 |
| | 5354 | 20914 |
| Set 4 | 42 | 5695 |
| | 42 | 5696 |
| | 42 | 5697 |
| | 45 | 5704 |
| | 45 | 5705 |
| | 45 | 5706 |
| | 79 | 5806 |
| | 79 | 5807 |
| | 79 | 5808 |
| | 275 | 6379 |
| | 275 | 6380 |
| | 275 | 6381 |
| | 349 | 6590 |
| | 349 | 6591 |
| | 349 | 6592 |
| | 830 | 7951 |
| | 830 | 7952 |
| | 830 | 7953 |
| | 841 | 7984 |
| | 841 | 7985 |
| | 841 | 7986 |
| | 894 | 8131 |
| | 894 | 8132 |
| | 894 | 8133 |
| | 895 | 8134 |
| | 895 | 8135 |
| | 895 | 8136 |
| | 902 | 8153 |
| | 902 | 8154 |
| | 902 | 8155 |
| | 1043 | 8568 |
| | 1043 | 8569 |
| | 1043 | 8570 |
| | 1356 | 9484 |
| | 1356 | 9485 |
| | 1356 | 9486 |
| | 1445 | 9746 |
| | 1445 | 9747 |
| | 1445 | 9748 |
| | 1668 | 10392 |
| | 1668 | 10393 |
| | 1668 | 10394 |
| | 1782 | 10714 |
| | 1782 | 10715 |
| | 1782 | 10716 |
| | 1800 | 10765 |
| | 1800 | 10766 |
| | 1800 | 10767 |
| | 1833 | 10859 |
| | 1833 | 10860 |
| | 2542 | 12889 |
| | 2542 | 12890 |
| | 2542 | 12891 |
| | 2698 | 13327 |
| | 2698 | 13328 |
| | 2698 | 13329 |
| | 3156 | 14634 |
| | 3156 | 14635 |
| | 3156 | 14636 |
| | 3158 | 14640 |
| | 3158 | 14641 |
| | 3158 | 14642 |
| | 3160 | 14646 |
| | 3160 | 14647 |
| | 3160 | 14648 |
| | 3278 | 14983 |
| | 3278 | 14984 |
| | 3278 | 14985 |
| | 3606 | 15919 |
| | 3606 | 15920 |
| | 3606 | 15921 |
| | 3826 | 16550 |
| | 3826 | 16551 |
| | 3826 | 16552 |
| | 3967 | 16956 |
| | 3967 | 16957 |

TABLE 3-continued

| Collection of probe sets | Reference sequence (target sequence (SEQ ID)) | Specific probe (SEQ ID) |
|---|---|---|
| | 3967 | 16958 |
| | 3972 | 16971 |
| | 3972 | 16972 |
| | 3972 | 16973 |
| | 3976 | 16983 |
| | 3976 | 16984 |
| | 3976 | 16985 |
| | 4810 | 19364 |
| | 4810 | 19365 |
| | 4810 | 19366 |
| | 4864 | 19519 |
| | 4864 | 19520 |
| | 4864 | 19521 |
| | 4865 | 19522 |
| | 4865 | 19523 |
| | 4865 | 19524 |
| | 4867 | 19528 |
| | 4867 | 19529 |
| | 4867 | 19530 |

TABLE 3-continued

| Collection of probe sets | Reference sequence (target sequence (SEQ ID)) | Specific probe (SEQ ID) |
|---|---|---|
| | 4869 | 19534 |
| | 4869 | 19535 |
| | 4869 | 19536 |
| Set 1 | 2363 | 12390 |
| | 2363 | 12391 |
| | 2363 | 12392 |
| | 2364 | 12393 |
| | 4218 | 17670 |
| | 5063 | 20074 |
| | 5063 | 20075 |
| | 5063 | 20076 |
| | 5307 | 20777 |
| | 5307 | 20778 |
| | 5307 | 20779 |
| | 5426 | 21121 |
| | 5426 | 21122 |
| | 5426 | 21123 |

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US08481701B2). An electronic copy of the "Sequence Listing" will also be available from the USPTO upon request and payment of the fee set forth in 37 CFR 1.19(b)(3).

The invention claimed is:

1. A product comprising a support on which is immobilized a plurality of probes, the probes consisting of at least 15 consecutive nucleotides of each of SEQ ID NO: 2363, 2364, 5307, 5426, 4218 and 5063, or the complements thereof.

2. A kit comprising the product according to claim 1 and reagents for a hybridization reaction.

3. The product of claim 1, wherein the support is solid or semi-solid.

4. The product of claim 3, wherein the support is selected from a slide, a bead, a membrane, a filter, a column, and a plate.

* * * * *